US012661193B2

(12) United States Patent

Hutter et al.

(10) Patent No.: US 12,661,193 B2

(45) Date of Patent: Jun. 23, 2026

(54) METHOD FOR USING A TELESCOPING DRIVE TABLE

(71) Applicant: Imperative Care, Inc., Campbell, CA (US)

(72) Inventors: Matthew Hutter, Los Angeles, CA (US); Craig Mar, Fremont, CA (US)

(73) Assignee: Imperative Care, Inc., Campbell, CA (US)

( * ) Notice: Subject to any disclaimer, the term of this patent is extended or adjusted under 35 U.S.C. 154(b) by 150 days.

(21) Appl. No.: 18/525,446

(22) Filed: Nov. 30, 2023

(65) Prior Publication Data

US 2024/0181214 A1 Jun. 6, 2024

Related U.S. Application Data

(60) Provisional application No. 63/385,761, filed on Dec. 1, 2022.

(51) Int. Cl.
*A61B 34/30* (2016.01)
*A61B 17/00* (2006.01)
(Continued)

(52) U.S. Cl.
CPC .............. *A61B 34/30* (2016.02); *A61B 17/00* (2013.01); *A61B 34/71* (2016.02); *A61G 13/10* (2013.01);
(Continued)

(58) Field of Classification Search
CPC ......... A61B 34/30; A61B 17/00; A61B 34/71;

A61B 2017/00477; A61B 2034/301; A61B 2034/304; A61G 13/10; A61G 13/101; A61G 2210/50; A61M 25/0014; A61M 25/0043; A61M 25/0097; A61M 25/0113; A61M 25/0127; A61M 25/0147;
(Continued)

(56) References Cited

U.S. PATENT DOCUMENTS

| | | | |
|---|---|---|---|
| 1,286,033 A | 11/1918 | Lambeth | |
| 4,819,653 A | 4/1989 | Marks | |

(Continued)

FOREIGN PATENT DOCUMENTS

| | | |
|---|---|---|
| AU | 2006268156 | 4/2012 |
| CN | 102462533 | 5/2012 |

(Continued)

OTHER PUBLICATIONS

US 12,076,032 B1, 09/2024, Teigen et al. (withdrawn)
(Continued)

*Primary Examiner* — Richard G Louis
(74) *Attorney, Agent, or Firm* — Knobbe, Martens, Olson & Bear, LLP

(57) ABSTRACT

A method for driving an interventional device assembly along a drive table. The method includes axially advancing an extendable member from an end of a main body of a drive table and axially advancing a hub adapter from a first axial position within the main body to a second axial position within the extendable member beyond the end of the main body. The hub adapter is configured to couple to a corresponding hub so that axial movement of the hub adapter drives axial movement of the corresponding hub.

17 Claims, 49 Drawing Sheets

(51) Int. Cl.

| | |
|---|---|
| *A61B 34/00* | (2016.01) |
| *A61G 13/10* | (2006.01) |
| *A61M 25/00* | (2006.01) |
| *A61M 25/01* | (2006.01) |
| *A61M 25/09* | (2006.01) |

(52) U.S. Cl.
CPC .... *A61M 25/0014* (2013.01); *A61M 25/0043* (2013.01); *A61M 25/0097* (2013.01); *A61M 25/0113* (2013.01); *A61M 25/0127* (2013.01); *A61M 25/0147* (2013.01); *A61M 25/09041* (2013.01); *A61B 2017/00477* (2013.01); *A61B 2034/301* (2016.02); *A61B 2034/304* (2016.02); *A61M 2025/0059* (2013.01); *A61M 2025/0062* (2013.01)

(58) Field of Classification Search
CPC .... A61M 25/09041; A61M 2025/0059; A61M 2025/0062
See application file for complete search history.

(56) References Cited

U.S. PATENT DOCUMENTS

| | | | |
|---|---|---|---|
| 4,925,444 A | 5/1990 | Orkin |
| 5,037,404 A | 8/1991 | Gold et al. |
| 5,131,391 A | 7/1992 | Sakai et al. |
| 5,380,268 A | 1/1995 | Wheeler |
| 5,638,818 A | 6/1997 | Diab et al. |
| 5,882,333 A | 3/1999 | Schaer et al. |
| 5,989,208 A | 11/1999 | Nita |
| 6,096,004 A | 8/2000 | Meglan et al. |
| 6,375,471 B1 | 4/2002 | Wendlandt et al. |
| 6,400,971 B1 | 6/2002 | Firanov et al. |
| 6,726,675 B1 | 4/2004 | Beyar |
| 6,821,287 B1 | 11/2004 | Jang |
| 7,192,433 B2 | 3/2007 | Osypka et al. |
| 7,214,230 B2 | 5/2007 | Brock et al. |
| 7,331,967 B2 | 2/2008 | Lee et al. |
| 7,379,790 B2 | 5/2008 | Toth et al. |
| 7,556,611 B2 | 7/2009 | Kolenbrander et al. |
| 7,567,233 B2 | 7/2009 | Garibaldi et al. |
| 7,608,083 B2 | 10/2009 | Lee et al. |
| 7,615,042 B2 | 11/2009 | Beyar et al. |
| 7,727,185 B2 | 6/2010 | Weitzner |
| 7,747,960 B2 | 6/2010 | Garibaldi et al. |
| 7,756,308 B2 | 7/2010 | Viswanathan |
| 7,761,133 B2 | 7/2010 | Viswanathan et al. |
| 7,766,894 B2 | 8/2010 | Weitzner et al. |
| 7,789,874 B2 | 9/2010 | Yu et al. |
| D626,250 S | 10/2010 | Wenderow et al. |
| 7,818,076 B2 | 10/2010 | Viswanathan |
| 7,831,294 B2 | 11/2010 | Viswanathan |
| 7,850,640 B2 | 12/2010 | Williams et al. |
| 7,850,642 B2 | 12/2010 | Moll et al. |
| 7,853,306 B2 | 12/2010 | Viswanathan et al. |
| 7,884,727 B2 | 2/2011 | Tran |
| 7,886,743 B2 | 2/2011 | Cooper et al. |
| 7,887,549 B2 | 2/2011 | Wenderow et al. |
| 7,909,798 B2 | 3/2011 | Osypka |
| 7,951,243 B2 | 5/2011 | Boyle, Jr. et al. |
| 7,955,316 B2 | 6/2011 | Weitzner et al. |
| 7,963,288 B2 | 6/2011 | Rosenberg et al. |
| 8,004,229 B2 | 8/2011 | Nowlin et al. |
| 8,021,326 B2 | 9/2011 | Moll et al. |
| RE42,804 E | 10/2011 | Dedig et al. |
| 8,052,636 B2 | 11/2011 | Moll et al. |
| 8,083,753 B2 | 12/2011 | Solar et al. |
| 8,108,069 B2 | 1/2012 | Stahler et al. |
| 8,114,032 B2 | 2/2012 | Ferry et al. |
| 8,123,726 B2 | 2/2012 | Searfoss et al. |
| 8,131,379 B2 | 3/2012 | Hauck |
| 8,137,317 B2 | 3/2012 | Osypka |
| 8,146,874 B2 | 4/2012 | Yu |
| 8,165,684 B2 | 4/2012 | Putz et al. |

| | | | |
|---|---|---|---|
| 8,190,238 B2 | 5/2012 | Moll et al. |
| 8,220,468 B2 | 7/2012 | Cooper et al. |
| 8,242,972 B2 | 8/2012 | Garibaldi et al. |
| 8,244,824 B2 | 8/2012 | Garibaldi et al. |
| 8,257,302 B2 | 9/2012 | Beyar et al. |
| 8,262,671 B2 | 9/2012 | Osypka |
| 8,281,807 B2 | 10/2012 | Trombley et al. |
| 8,307,693 B2 | 11/2012 | Uram et al. |
| D674,484 S | 1/2013 | Murphy et al. |
| 8,343,096 B2 | 1/2013 | Kirschenman et al. |
| 8,343,098 B2 | 1/2013 | Nystrom et al. |
| 8,377,077 B2 | 2/2013 | Reis |
| 8,390,438 B2 | 3/2013 | Olson et al. |
| 8,399,871 B2 | 3/2013 | Beyar et al. |
| 8,403,909 B2 | 3/2013 | Spohn et al. |
| D680,645 S | 4/2013 | Murphy et al. |
| 8,409,172 B2 | 4/2013 | Moll et al. |
| 8,467,853 B2 | 6/2013 | Hunter et al. |
| D685,468 S | 7/2013 | Murphy et al. |
| 8,480,618 B2 | 7/2013 | Wenderow et al. |
| 8,498,691 B2 | 7/2013 | Moll et al. |
| 8,506,555 B2 | 8/2013 | Morales |
| 8,521,331 B2 | 8/2013 | Itkowitz |
| 8,529,582 B2 | 9/2013 | Devengenzo et al. |
| 8,540,698 B2 | 9/2013 | Spohn et al. |
| 8,551,084 B2 | 10/2013 | Hauck et al. |
| 8,603,068 B2 | 12/2013 | Weitzner et al. |
| 8,613,730 B2 | 12/2013 | Hieb et al. |
| 8,617,102 B2 | 12/2013 | Moll et al. |
| 8,620,473 B2 | 12/2013 | Diolaiti et al. |
| 8,671,817 B1 | 3/2014 | Bogusky |
| 8,672,880 B2 | 3/2014 | Cohen et al. |
| 8,679,150 B1 | 3/2014 | Janardhan |
| 8,684,953 B2 | 4/2014 | Cabiri |
| 8,684,962 B2 | 4/2014 | Kirschenman et al. |
| 8,694,157 B2 | 4/2014 | Wenderow et al. |
| 8,740,840 B2 | 6/2014 | Foley et al. |
| 8,747,358 B2 | 6/2014 | Trombley et al. |
| 8,790,297 B2 | 7/2014 | Bromander et al. |
| 8,799,792 B2 | 8/2014 | Garibaldi et al. |
| 8,800,881 B2 | 8/2014 | Biset et al. |
| 8,801,661 B2 | 8/2014 | Moll et al. |
| 8,806,359 B2 | 8/2014 | Garibaldi et al. |
| 8,827,948 B2 | 9/2014 | Romo |
| 8,828,021 B2 | 9/2014 | Wenderow et al. |
| 8,833,293 B2 | 9/2014 | Horn |
| 8,840,628 B2 | 9/2014 | Green et al. |
| 8,852,162 B2 | 10/2014 | Williams et al. |
| 8,852,167 B2 | 10/2014 | Trombley et al. |
| 8,852,184 B2 | 10/2014 | Kucklick |
| 8,876,726 B2 | 11/2014 | Amit et al. |
| 8,894,610 B2 | 11/2014 | Macnamara et al. |
| 8,905,969 B2 | 12/2014 | Nystrom et al. |
| 8,939,963 B2 | 1/2015 | Rogers et al. |
| 8,961,491 B2 | 2/2015 | Uber et al. |
| 8,968,333 B2 | 3/2015 | Yu et al. |
| 8,974,408 B2 | 3/2015 | Wallace et al. |
| 8,974,420 B2 | 3/2015 | Searfoss et al. |
| 8,979,871 B2 | 3/2015 | Tye |
| 8,986,246 B2 | 3/2015 | Foley et al. |
| 9,005,271 B2 | 4/2015 | Ivancev |
| 9,056,200 B2 | 6/2015 | Uber et al. |
| 9,066,740 B2 | 6/2015 | Carlson et al. |
| 9,070,486 B2 | 6/2015 | Guerrera et al. |
| 9,095,681 B2 | 8/2015 | Wenderow et al. |
| 9,101,379 B2 | 8/2015 | Au et al. |
| 9,111,016 B2 | 8/2015 | Besson et al. |
| 9,132,949 B2 | 9/2015 | Bidet et al. |
| 9,138,566 B2 | 9/2015 | Cabiri |
| 9,168,356 B2 | 10/2015 | Wenderow et al. |
| 9,186,046 B2 | 11/2015 | Ramamurthy et al. |
| 9,199,033 B1 | 12/2015 | Cowan et al. |
| 9,205,227 B2 | 12/2015 | Cohen et al. |
| 9,206,309 B2 | 12/2015 | Appleby |
| 9,220,568 B2 | 12/2015 | Bromander et al. |
| 9,233,225 B2 | 1/2016 | Hebert |
| 9,241,768 B2 | 1/2016 | Sandhu et al. |
| 9,242,252 B2 | 1/2016 | Eberle et al. |
| 9,259,526 B2 | 2/2016 | Barron et al. |

(56) References Cited

U.S. PATENT DOCUMENTS

| | | | |
|---|---|---|---|
| 9,295,527 | B2 | 3/2016 | Kirschenman et al. |
| 9,314,306 | B2 | 4/2016 | Yu |
| 9,314,307 | B2 | 4/2016 | Richmond et al. |
| 9,314,310 | B2 | 4/2016 | Kirschenman et al. |
| 9,314,311 | B2 | 4/2016 | Wenderow et al. |
| 9,314,594 | B2 | 4/2016 | Kirschenman |
| 9,315,663 | B2 | 4/2016 | Appleby |
| 9,320,479 | B2 | 4/2016 | Wenderow et al. |
| 9,320,573 | B2 | 4/2016 | Sandhu et al. |
| 9,333,324 | B2 | 5/2016 | Cohen et al. |
| 9,345,859 | B2 | 5/2016 | Blacker |
| 9,351,735 | B2 | 5/2016 | Nagano et al. |
| 9,375,729 | B2 | 6/2016 | Eberle et al. |
| 9,402,977 | B2 | 8/2016 | Wenderow et al. |
| 9,408,669 | B2 | 8/2016 | Kokish et al. |
| 9,427,515 | B1 | 8/2016 | Nystrom |
| 9,427,562 | B2 | 8/2016 | Blacker |
| 9,439,736 | B2 | 9/2016 | Olson |
| 9,447,890 | B2 | 9/2016 | Jennings et al. |
| 9,452,276 | B2 | 9/2016 | Duindam et al. |
| 9,452,277 | B2 | 9/2016 | Blacker |
| 9,474,857 | B2 | 10/2016 | Riley et al. |
| 9,480,797 | B1 | 11/2016 | Swantner et al. |
| 9,488,971 | B2 | 11/2016 | Yip et al. |
| 9,498,291 | B2 | 11/2016 | Gilbert et al. |
| 9,510,912 | B2 | 12/2016 | Bencteux et al. |
| 9,517,305 | B2 | 12/2016 | Uram et al. |
| 9,532,840 | B2 | 1/2017 | Wong et al. |
| 9,533,121 | B2 | 1/2017 | Pacheco et al. |
| 9,545,497 | B2 | 1/2017 | Wenderow et al. |
| 9,549,783 | B2 | 1/2017 | Zirps |
| 9,566,201 | B2 | 2/2017 | Yu |
| 9,566,414 | B2 | 2/2017 | Wong et al. |
| 9,572,481 | B2 | 2/2017 | Duindam et al. |
| 9,585,806 | B2 | 3/2017 | Herrig |
| 9,586,029 | B2 | 3/2017 | Shekalim et al. |
| 9,603,573 | B2 | 3/2017 | Leininger et al. |
| 9,623,209 | B2 | 4/2017 | Wenderow et al. |
| 9,629,595 | B2 | 4/2017 | Walker et al. |
| 9,636,479 | B2 | 5/2017 | Bencteux et al. |
| 9,687,304 | B2 | 6/2017 | Bencteux et al. |
| 9,700,698 | B2 | 7/2017 | Pacheco et al. |
| 9,707,377 | B2 | 7/2017 | Cohen et al. |
| 9,717,552 | B2 | 8/2017 | Cosman |
| 9,744,305 | B2 | 8/2017 | Cowan et al. |
| 9,750,576 | B2 | 9/2017 | Murphy et al. |
| 9,750,953 | B2 | 9/2017 | Kalafut |
| 9,764,114 | B2 | 9/2017 | Murphy et al. |
| 9,770,301 | B2 | 9/2017 | Bencteux et al. |
| 9,782,130 | B2 | 10/2017 | Hauck et al. |
| 9,782,564 | B2 | 10/2017 | Zirps et al. |
| 9,789,285 | B1 | 10/2017 | Blacker |
| 9,814,534 | B2 | 11/2017 | Wenderow et al. |
| 9,825,455 | B2 | 11/2017 | Sandhu et al. |
| 9,827,410 | B2 | 11/2017 | Cowan et al. |
| 9,828,157 | B2 | 11/2017 | Roesler |
| 9,833,293 | B2 | 12/2017 | Wenderow et al. |
| 9,839,481 | B2 | 12/2017 | Blumenkranz et al. |
| 9,855,101 | B2 | 1/2018 | Wenderow et al. |
| 9,943,321 | B2 | 4/2018 | Nita |
| 9,943,958 | B2 | 4/2018 | Blacker et al. |
| 9,949,799 | B2 | 4/2018 | Hingwe et al. |
| 9,962,229 | B2 | 5/2018 | Blacker et al. |
| 9,981,109 | B2 | 5/2018 | Blacker et al. |
| 9,993,614 | B2 | 6/2018 | Pacheco et al. |
| 9,993,615 | B2 | 6/2018 | Blacker |
| 9,999,751 | B2 | 6/2018 | Pacheco et al. |
| 10,010,699 | B2 | 7/2018 | Cohen et al. |
| 10,029,072 | B2 | 7/2018 | Hebert |
| 10,046,140 | B2 | 8/2018 | Kokish et al. |
| 10,052,761 | B2 | 8/2018 | Langenfeld et al. |
| 10,071,224 | B2 | 9/2018 | Hebert |
| 10,071,225 | B2 | 9/2018 | Hebert |
| 10,085,805 | B1 | 10/2018 | Blacker |
| 10,086,167 | B2 | 10/2018 | Hebert |
| 10,105,486 | B2 | 10/2018 | Trombley et al. |
| 10,111,703 | B2 | 10/2018 | Cosman, Jr |
| 10,123,843 | B2 | 11/2018 | Wong et al. |
| 10,123,844 | B2 | 11/2018 | Nowlin et al. |
| 10,124,149 | B2 | 11/2018 | Hebert |
| 10,130,427 | B2 | 11/2018 | Tanner et al. |
| 10,138,025 | B2 | 11/2018 | Nakamura |
| 10,145,747 | B1 | 12/2018 | Lin et al. |
| 10,149,698 | B2 | 12/2018 | Wulfman et al. |
| 10,178,995 | B2 | 1/2019 | Cragg |
| 10,183,147 | B2 | 1/2019 | Yang et al. |
| 10,201,314 | B2 | 2/2019 | Frederick et al. |
| 10,207,315 | B2 | 2/2019 | Appleby |
| 10,231,788 | B2 | 3/2019 | Olson et al. |
| 10,238,456 | B2 | 3/2019 | Murphy et al. |
| 10,245,112 | B2 | 4/2019 | Kottenstette et al. |
| 10,258,285 | B2 | 4/2019 | Hauck et al. |
| 10,271,910 | B2 | 4/2019 | Wenderow et al. |
| 10,299,867 | B2 | 5/2019 | Wenderow et al. |
| 10,307,061 | B2 | 6/2019 | Cohen |
| 10,307,570 | B2 | 6/2019 | Blacker |
| 10,322,277 | B2 | 6/2019 | Nystrom |
| 10,342,606 | B2 | 7/2019 | Cosman |
| 10,342,953 | B2 | 7/2019 | Wenderow et al. |
| 10,363,062 | B2 | 7/2019 | Spencer et al. |
| 10,363,109 | B2 | 7/2019 | Dachs, II et al. |
| 10,368,951 | B2 | 8/2019 | Moll et al. |
| 10,391,234 | B2 | 8/2019 | Sams et al. |
| 10,420,537 | B2 | 9/2019 | Salahieh et al. |
| 10,426,557 | B2 | 10/2019 | Amiri et al. |
| 10,426,559 | B2 | 10/2019 | Graetzel et al. |
| 10,426,926 | B2 | 10/2019 | Blacker et al. |
| 10,449,007 | B2 | 10/2019 | Deboeuf et al. |
| 10,456,556 | B2 | 10/2019 | Cabiri |
| 10,512,514 | B2 | 12/2019 | Nowlin et al. |
| 10,522,250 | B2 | 12/2019 | Spohn et al. |
| 10,531,883 | B1 | 1/2020 | Deville et al. |
| 10,531,929 | B2 | 1/2020 | Widenhouse et al. |
| 10,537,400 | B2 | 1/2020 | Dachs et al. |
| 10,539,478 | B2 | 1/2020 | Lin et al. |
| 10,549,071 | B2 | 2/2020 | Falb et al. |
| 10,549,084 | B2 | 2/2020 | Sokolov et al. |
| 10,555,780 | B2 | 2/2020 | Tanner et al. |
| 10,556,092 | B2 | 2/2020 | Yu et al. |
| 10,561,821 | B2 | 2/2020 | Wenderow et al. |
| 10,568,539 | B2 | 2/2020 | Kowshik et al. |
| 10,568,700 | B2 | 2/2020 | Donhowe et al. |
| 10,583,276 | B2 | 3/2020 | Zirps |
| 10,588,656 | B2 | 3/2020 | Trosper et al. |
| 10,589,018 | B2 | 3/2020 | Uber et al. |
| D881,234 | S | 4/2020 | Capela |
| 10,611,391 | B1 | 4/2020 | Klem et al. |
| 10,639,098 | B2 | 5/2020 | Cosman |
| 10,647,007 | B2 | 5/2020 | Cordoba et al. |
| 10,653,863 | B1 | 5/2020 | Blacker et al. |
| 10,660,814 | B2 | 5/2020 | Soundararajan et al. |
| 10,661,453 | B2 | 5/2020 | Koenig et al. |
| 10,687,903 | B2 | 6/2020 | Lewis et al. |
| 10,695,140 | B2 | 6/2020 | Overmyer et al. |
| 10,695,533 | B2 | 6/2020 | Deboeuf et al. |
| 10,695,536 | B2 | 6/2020 | Weitzner et al. |
| 10,709,510 | B2 | 7/2020 | Kottenstette |
| 10,709,512 | B2 | 7/2020 | Bajo et al. |
| 10,716,726 | B2 | 7/2020 | Bergman et al. |
| 10,722,253 | B2 | 7/2020 | Deville et al. |
| 10,729,825 | B2 | 8/2020 | Boyle, Jr. et al. |
| 10,736,706 | B2 | 8/2020 | Scheib |
| 10,737,061 | B2 | 8/2020 | Parmar |
| 10,744,302 | B2 | 8/2020 | Pacheco et al. |
| 10,765,303 | B2 | 9/2020 | Graetzel et al. |
| 10,765,486 | B2 | 9/2020 | Bajo et al. |
| 10,779,775 | B2 | 9/2020 | Bergman et al. |
| 10,779,895 | B2 | 9/2020 | Wenderow et al. |
| 10,783,993 | B2 | 9/2020 | Spohn et al. |
| 10,799,305 | B2 | 10/2020 | Murphy et al. |
| 10,806,905 | B2 | 10/2020 | Asmus |
| 10,813,713 | B2 | 10/2020 | Koch et al. |
| 10,814,102 | B2 | 10/2020 | Laby et al. |
| 10,820,951 | B2 | 11/2020 | Soundararajan et al. |

(56) References Cited

U.S. PATENT DOCUMENTS

| | | |
|---|---|---|
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafii-Tari et al. |
| 10,835,329 B2 | 11/2020 | Wenderow et al. |
| 10,835,668 B2 | 11/2020 | Novickoff et al. |
| 10,849,702 B2 | 12/2020 | Hsu et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,898,082 B2 | 1/2021 | Sandgaard |
| 10,898,288 B2 | 1/2021 | Dachs et al. |
| 10,900,771 B2 | 1/2021 | Kottenstette et al. |
| 10,912,624 B2 | 2/2021 | Prentakis et al. |
| 10,912,924 B2 | 2/2021 | Park et al. |
| 10,945,904 B2 | 3/2021 | De Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,040,147 B2 | 6/2021 | Wagner |
| 11,045,274 B2 | 6/2021 | Dachs, II et al. |
| 11,052,226 B2 | 7/2021 | Salahieh et al. |
| 11,058,508 B2 | 7/2021 | Scheib et al. |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |
| 11,096,712 B2 | 8/2021 | Teigen et al. |
| 11,104,012 B2 | 8/2021 | Cordoba et al. |
| 11,109,919 B2 | 9/2021 | Murphy et al. |
| 11,109,920 B2 | 9/2021 | Al-Jadda et al. |
| 11,109,921 B2 | 9/2021 | Kottenstette et al. |
| 11,110,217 B2 | 9/2021 | O'Brien et al. |
| 11,114,918 B2 | 9/2021 | Zirps |
| 11,129,602 B2 | 9/2021 | Wong et al. |
| 11,141,566 B2 | 10/2021 | Cabiri |
| 11,147,950 B2 | 10/2021 | Destrebecq et al. |
| 11,179,213 B2 | 11/2021 | Huang et al. |
| 11,179,546 B2 | 11/2021 | Martin |
| 11,185,455 B2 | 11/2021 | Cagle et al. |
| 11,191,893 B2 | 12/2021 | Capone et al. |
| 11,197,683 B1 | 12/2021 | Teigen et al. |
| 11,207,147 B2 | 12/2021 | Diamond et al. |
| 11,209,300 B2 | 12/2021 | Johnson |
| 11,213,356 B2 | 1/2022 | Tanner et al. |
| 11,213,362 B2 | 1/2022 | Sharon et al. |
| 11,213,654 B2 | 1/2022 | Murphy et al. |
| 11,234,779 B2 | 2/2022 | Fuerst et al. |
| 11,234,781 B2 | 2/2022 | Penny et al. |
| 11,234,784 B2 | 2/2022 | Alden |
| 11,241,291 B2 | 2/2022 | Sharon et al. |
| 11,259,881 B2 | 3/2022 | Garcia Kilroy et al. |
| 11,266,424 B2 | 3/2022 | Hofmann et al. |
| 11,291,515 B2 | 4/2022 | Sharon et al. |
| 11,298,198 B2 | 4/2022 | Fournier et al. |
| 11,304,668 B2 | 4/2022 | Wenderow et al. |
| 11,318,618 B2 | 5/2022 | Desai |
| 11,331,157 B2 | 5/2022 | Russell et al. |
| 11,337,712 B2 | 5/2022 | Teigen et al. |
| 11,337,764 B2 | 5/2022 | Deboeuf et al. |
| 11,357,586 B2 | 6/2022 | Huang et al. |
| 11,357,597 B2 | 6/2022 | Jhaveri et al. |
| 11,359,156 B2 | 6/2022 | Long et al. |
| 11,376,086 B2 | 7/2022 | McGrogan et al. |
| 11,389,360 B2 | 7/2022 | Koenig et al. |
| 11,395,665 B2 | 7/2022 | Yang et al. |
| 11,400,214 B2 | 8/2022 | Porter |
| 11,406,402 B2 | 8/2022 | Deville et al. |
| 11,413,101 B2 | 8/2022 | Sen et al. |
| 11,413,431 B2 | 8/2022 | Blacker |
| 11,419,977 B2 | 8/2022 | Cowan et al. |
| 11,426,246 B2 | 8/2022 | Asadian et al. |
| 11,432,835 B2 | 9/2022 | Shaffer et al. |
| 11,432,840 B2 | 9/2022 | Grothe et al. |
| 11,448,327 B2 | 9/2022 | Heffner et al. |
| 11,464,587 B2 | 10/2022 | Yu et al. |
| 11,464,589 B1 | 10/2022 | Roh et al. |
| 11,472,030 B2 | 10/2022 | Ho et al. |
| 11,478,329 B2 | 10/2022 | Gee et al. |
| 11,490,911 B2 | 11/2022 | Panian |
| 11,491,313 B2 | 11/2022 | Fischel |
| 11,497,481 B2 | 11/2022 | Penny et al. |
| 11,497,523 B2 | 11/2022 | Trosper et al. |
| 11,497,568 B2 | 11/2022 | Ho et al. |
| 11,510,736 B2 | 11/2022 | Rafii-Tari et al. |
| D976,399 S | 1/2023 | Carmi |
| 11,547,426 B2 | 1/2023 | Deville et al. |
| 11,547,511 B2 | 1/2023 | Asadian et al. |
| 11,564,649 B2 | 1/2023 | Kedmi-Shahar et al. |
| 11,571,267 B2 | 2/2023 | Gonenc et al. |
| 11,576,743 B2 | 2/2023 | Venkataraman et al. |
| 11,577,382 B2 | 2/2023 | Cagle et al. |
| 11,589,931 B2 | 2/2023 | Desai et al. |
| 11,607,108 B2 | 3/2023 | Yu et al. |
| 11,628,024 B2 | 4/2023 | Kapadia |
| 11,633,247 B2 | 4/2023 | Johnson et al. |
| 11,642,181 B2 | 5/2023 | Nobles et al. |
| 11,653,905 B2 | 5/2023 | Wong et al. |
| 11,660,151 B2 | 5/2023 | Schena |
| 11,660,437 B2 | 5/2023 | Verma |
| 11,672,602 B2 | 6/2023 | Monteverde et al. |
| 11,678,943 B2 | 6/2023 | Zhou et al. |
| 11,678,948 B2 | 6/2023 | Vargas et al. |
| 11,684,759 B2 | 6/2023 | Hayzelden |
| 11,690,985 B2 | 7/2023 | Calhoun et al. |
| 11,696,808 B2 | 7/2023 | Blacker et al. |
| 11,696,810 B2 | 7/2023 | Asadian et al. |
| 11,701,196 B2 | 7/2023 | Scheib et al. |
| 11,703,604 B2 | 7/2023 | Dissertori et al. |
| 11,712,805 B2 | 8/2023 | Zhou et al. |
| 11,713,376 B2 | 8/2023 | Leroux et al. |
| 11,717,356 B2 | 8/2023 | Amiri et al. |
| 11,717,640 B2 | 8/2023 | Fantuzzi et al. |
| 11,723,739 B2 | 8/2023 | Asadian et al. |
| 11,723,744 B2 | 8/2023 | Ergueta Tejerina et al. |
| 11,737,821 B2 | 8/2023 | Algawi et al. |
| 11,744,989 B2 | 9/2023 | Blacker |
| 11,759,269 B2 | 9/2023 | Zhou et al. |
| 11,764,873 B2 | 9/2023 | Burla et al. |
| 11,765,360 B2 | 9/2023 | Schroers et al. |
| 11,766,786 B2 | 9/2023 | Cordoba et al. |
| 11,780,092 B2 | 10/2023 | Desai et al. |
| 11,785,938 B2 | 10/2023 | Clavien et al. |
| 11,786,329 B2 | 10/2023 | Fuerst et al. |
| 11,789,315 B1 | 10/2023 | Yu et al. |
| 11,793,500 B2 | 10/2023 | Vargas |
| 11,793,597 B2 | 10/2023 | Vargas et al. |
| 11,801,365 B2 | 10/2023 | Blacker et al. |
| 11,813,203 B2 | 11/2023 | Timm et al. |
| 11,819,295 B2 | 11/2023 | Wenderow et al. |
| 11,832,904 B2 | 12/2023 | Wenderow et al. |
| 11,844,580 B2 | 12/2023 | Sen et al. |
| 11,844,732 B2 | 12/2023 | Klem et al. |
| 11,883,119 B2 | 1/2024 | Sen et al. |
| 11,883,245 B2 | 1/2024 | Fathollahi Ghezelghieh et al. |
| 11,890,024 B2 | 2/2024 | Panian |
| 11,890,432 B2 | 2/2024 | Awad et al. |
| 11,896,325 B2 | 2/2024 | Clark et al. |
| 11,903,669 B2 | 2/2024 | Cope et al. |
| 11,906,009 B2 | 2/2024 | Klem |
| 11,910,997 B2 | 2/2024 | Fuerst et al. |
| 11,911,120 B2 | 2/2024 | Freiin Von Kapri et al. |
| 11,911,910 B2 | 2/2024 | Gonenc et al. |
| 11,918,240 B2 | 3/2024 | Deville et al. |
| 11,918,312 B2 | 3/2024 | Yu |
| 11,918,423 B2 | 3/2024 | Kottenstette et al. |

(56)  References Cited

U.S. PATENT DOCUMENTS

| | | | |
|---|---|---|---|
| 11,931,901 | B2 | 3/2024 | Murphy et al. |
| 11,998,290 | B2 | 6/2024 | Murphy et al. |
| 12,004,829 | B2 | 6/2024 | Searfoss et al. |
| 12,005,589 | B2 | 6/2024 | Rea et al. |
| 12,035,989 | B2 | 7/2024 | Clark et al. |
| 12,046,363 | B2 | 7/2024 | Shrivastava et al. |
| D1,038,990 | S | 8/2024 | Inwood |
| 12,059,161 | B2 | 8/2024 | Deville et al. |
| 12,059,225 | B2 | 8/2024 | Zhou et al. |
| D1,043,739 | S | 9/2024 | Hernandez |
| 12,076,036 | B2 | 9/2024 | Baron et al. |
| 12,076,099 | B2 | 9/2024 | Shrivastava et al. |
| 12,076,497 | B2 | 9/2024 | Fantuzzi et al. |
| 12,076,505 | B2 | 9/2024 | Haubert |
| 12,082,982 | B2 | 9/2024 | Jhaveri et al. |
| 12,087,024 | B2 | 9/2024 | Djelouah et al. |
| 12,102,290 | B2 | 10/2024 | Sharon et al. |
| 12,114,940 | B2 | 10/2024 | Garcia Kilroy et al. |
| 12,117,624 | B2 | 10/2024 | Fuerst et al. |
| 12,133,700 | B2 | 11/2024 | Miller et al. |
| 12,133,702 | B2 | 11/2024 | Nowlin et al. |
| 12,133,965 | B2 | 11/2024 | Chassot et al. |
| 12,137,990 | B2 | 11/2024 | Walker et al. |
| 12,138,004 | B2 | 11/2024 | Cone et al. |
| 12,138,130 | B2 | 11/2024 | Garbus et al. |
| 12,144,564 | B2 | 11/2024 | Barbagli et al. |
| 12,144,569 | B2 | 11/2024 | Cone et al. |
| 12,144,575 | B2 | 11/2024 | Torabi |
| 12,150,660 | B1 | 11/2024 | Teigen et al. |
| 12,150,796 | B2 | 11/2024 | Wenderow et al. |
| 12,156,666 | B2 | 12/2024 | Trosper et al. |
| 12,156,667 | B2 | 12/2024 | Trosper et al. |
| 12,156,711 | B2 | 12/2024 | Liao et al. |
| 12,157,238 | B2 | 12/2024 | Fredrickson et al. |
| 12,161,419 | B2 | 12/2024 | Fuerst et al. |
| 12,171,505 | B2 | 12/2024 | Barbagli et al. |
| 12,171,543 | B2 | 12/2024 | Duindam et al. |
| 12,177,411 | B2 | 12/2024 | Culman |
| 12,178,387 | B2 | 12/2024 | McDowall et al. |
| 12,178,399 | B2 | 12/2024 | Itkowitz et al. |
| 12,178,526 | B2 | 12/2024 | McKenney et al. |
| 12,178,534 | B2 | 12/2024 | Asadian et al. |
| 12,185,947 | B2 | 1/2025 | Hart |
| 12,191,031 | B2 | 1/2025 | Azizian et al. |
| 12,201,484 | B2 | 1/2025 | Itkowitz et al. |
| 12,201,485 | B2 | 1/2025 | McDowall et al. |
| 12,212,240 | B2 | 1/2025 | Schulz |
| 12,232,838 | B2 | 2/2025 | Lau et al. |
| 12,329,397 | B2 | 6/2025 | Bartholomew |
| 12,350,415 | B2 | 7/2025 | Kumar et al. |
| 12,376,928 | B2 | 8/2025 | Lau et al. |
| 12,377,206 | B2 | 8/2025 | Bartholomew et al. |
| 12,383,668 | B2 | 8/2025 | Batarilo et al. |
| 12,396,741 | B2 | 8/2025 | Blacker |
| 12,397,099 | B2 | 8/2025 | Aaron et al. |
| 12,419,501 | B2 | 9/2025 | Canale et al. |
| 12,419,703 | B2 | 9/2025 | Yang et al. |
| 12,433,702 | B2 | 10/2025 | Lau et al. |
| 12,440,289 | B2 | 10/2025 | Lau et al. |
| 12,446,979 | B2 | 10/2025 | Yang et al. |
| 12,447,317 | B2 | 10/2025 | Lau et al. |
| D1,102,447 | S | 11/2025 | Bartholomew et al. |
| 12,508,093 | B2 | 12/2025 | Lee et al. |
| 2002/0091372 | A1 | 7/2002 | Cragg et al. |
| 2002/0113501 | A1 | 8/2002 | Doi |
| 2002/0192113 | A1 | 12/2002 | Uffenheimer et al. |
| 2003/0071285 | A1 | 4/2003 | Tsukernik |
| 2003/0100849 | A1 | 5/2003 | Jang |
| 2003/0105451 | A1 | 6/2003 | Westlund et al. |
| 2003/0114739 | A1 | 6/2003 | Fuimaono et al. |
| 2003/0125673 | A1 | 7/2003 | Houde et al. |
| 2004/0068248 | A1 | 4/2004 | Mooney et al. |
| 2004/0097805 | A1 | 5/2004 | Verard et al. |
| 2004/0143225 | A1 | 7/2004 | Callan |
| 2005/0077225 | A1 | 4/2005 | Usher et al. |
| 2005/0107667 | A1 | 5/2005 | Danitz |
| 2005/0165276 | A1 | 7/2005 | Belson et al. |
| 2005/0277912 | A1 | 12/2005 | John |
| 2006/0011501 | A1 | 1/2006 | Itou et al. |
| 2006/0095022 | A1 | 5/2006 | Moll et al. |
| 2006/0146010 | A1 | 7/2006 | Schneider |
| 2006/0200026 | A1 | 9/2006 | Wallace et al. |
| 2006/0200191 | A1 | 9/2006 | Zadno-Azizi |
| 2007/0060879 | A1 | 3/2007 | Weitzner |
| 2007/0060915 | A1 | 3/2007 | Kucklick |
| 2007/0106208 | A1 | 5/2007 | Uber et al. |
| 2007/0142824 | A1 | 6/2007 | Devengenzo |
| 2007/0179473 | A1 | 8/2007 | Masters et al. |
| 2007/0270639 | A1 | 11/2007 | Long |
| 2008/0027464 | A1 | 1/2008 | Moll et al. |
| 2008/0086051 | A1 | 4/2008 | Voegele |
| 2008/0234631 | A1 | 9/2008 | Reis |
| 2008/0255505 | A1 | 10/2008 | Carlson et al. |
| 2008/0262513 | A1 | 10/2008 | Stahler et al. |
| 2008/0319387 | A1 | 12/2008 | Amisar et al. |
| 2009/0012464 | A1 | 1/2009 | Martin |
| 2009/0076445 | A1 | 3/2009 | Furnish |
| 2009/0082722 | A1 | 3/2009 | Munger et al. |
| 2009/0131955 | A1 | 5/2009 | Wenderow et al. |
| 2009/0153374 | A1 | 6/2009 | Maw et al. |
| 2009/0171332 | A1 | 7/2009 | Bonneau |
| 2009/0204078 | A1 | 8/2009 | Mitchell et al. |
| 2009/0247943 | A1 | 10/2009 | Kirschenman et al. |
| 2009/0247993 | A1 | 10/2009 | Kirschenman et al. |
| 2009/0254083 | A1 | 10/2009 | Wallace et al. |
| 2009/0259200 | A1 | 10/2009 | Lampropoulos |
| 2009/0264785 | A1 | 10/2009 | Causevic et al. |
| 2010/0069833 | A1 | 3/2010 | Wenderow et al. |
| 2010/0175701 | A1 | 7/2010 | Reis et al. |
| 2010/0204712 | A1 | 8/2010 | Mallaby |
| 2010/0204713 | A1 | 8/2010 | Ruiz Morales |
| 2010/0280363 | A1 | 11/2010 | Skarda et al. |
| 2010/0286756 | A1 | 11/2010 | Dorn |
| 2010/0305502 | A1 | 12/2010 | Ferry et al. |
| 2011/0004223 | A1 | 1/2011 | Leeflang |
| 2011/0015484 | A1 | 1/2011 | Alvarez et al. |
| 2011/0028894 | A1 | 2/2011 | Foley et al. |
| 2011/0144658 | A1 | 6/2011 | Wenderow et al. |
| 2011/0166447 | A1 | 7/2011 | Windolf |
| 2011/0238010 | A1 | 9/2011 | Kirschenman |
| 2011/0288544 | A1 | 11/2011 | Verin et al. |
| 2011/0313318 | A1 | 12/2011 | Rule et al. |
| 2012/0071822 | A1 | 3/2012 | Romo |
| 2012/0071895 | A1 | 3/2012 | Stahler et al. |
| 2012/0154431 | A1 | 6/2012 | Fram |
| 2012/0172798 | A1 | 7/2012 | Miller et al. |
| 2012/0179032 | A1 | 7/2012 | Bromander et al. |
| 2012/0245595 | A1 | 9/2012 | Kesavadas et al. |
| 2012/0316458 | A1 | 12/2012 | Rahman |
| 2013/0030408 | A1 | 1/2013 | Piferi |
| 2013/0035537 | A1 | 2/2013 | Wallace |
| 2013/0053704 | A1 | 2/2013 | Bernak et al. |
| 2013/0096551 | A1 | 4/2013 | Govari et al. |
| 2013/0131499 | A1 | 5/2013 | Chan et al. |
| 2013/0214912 | A1 | 8/2013 | Beyar et al. |
| 2013/0231678 | A1 | 9/2013 | Wenderow |
| 2014/0058321 | A1 | 2/2014 | Wenderow et al. |
| 2014/0066900 | A1 | 3/2014 | Blacker |
| 2014/0150782 | A1 | 6/2014 | Vazales |
| 2014/0163364 | A1 | 6/2014 | Perers |
| 2014/0216250 | A1 | 8/2014 | Meyer |
| 2014/0228762 | A1 | 8/2014 | Capone |
| 2014/0243742 | A1 | 8/2014 | Pacheco et al. |
| 2014/0276016 | A1 | 9/2014 | Stigall |
| 2014/0276233 | A1 | 9/2014 | Murphy |
| 2014/0276389 | A1 | 9/2014 | Walker |
| 2014/0276948 | A1 | 9/2014 | Zirps |
| 2014/0318702 | A1 | 10/2014 | Tegg |
| 2015/0005738 | A1 | 1/2015 | Blacker |
| 2015/0005745 | A1 | 1/2015 | Bergman et al. |
| 2015/0073391 | A1 | 3/2015 | Hutchins et al. |
| 2015/0088002 | A1 | 3/2015 | Podhajsky |
| 2015/0157252 | A1 | 6/2015 | Sabesan |
| 2015/0272683 | A1 | 10/2015 | Yang et al. |

(56) References Cited

U.S. PATENT DOCUMENTS

| | | |
|---|---|---|
| 2015/0314105 A1 | 11/2015 | Gasparyan |
| 2015/0320478 A1 | 11/2015 | Cosman, Jr. |
| 2015/0320479 A1 | 11/2015 | Cosman, Jr. |
| 2015/0320480 A1 | 11/2015 | Cosman, Jr. |
| 2015/0320481 A1 | 11/2015 | Cosman, Jr. |
| 2015/0327875 A1 | 11/2015 | Look |
| 2015/0374483 A1 | 12/2015 | Janardhan |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0082502 A1 | 3/2016 | Appleby |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |
| 2017/0027653 A1 | 2/2017 | Kirschenman |
| 2017/0135773 A1 | 5/2017 | Lohmeier et al. |
| 2017/0143416 A1 | 5/2017 | Guler et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0281288 A1 | 10/2017 | Au |
| 2017/0311908 A1 | 11/2017 | Kariv et al. |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1* | 6/2018 | Yi ..................... A61M 25/0116 |
| 2018/0185104 A1 | 7/2018 | Olson et al. |
| 2018/0199916 A1 | 7/2018 | Sugihara et al. |
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0008591 A1 | 1/2019 | Desai |
| 2019/0030324 A1 | 1/2019 | Grace et al. |
| 2019/0076640 A1 | 3/2019 | Bhatnagar et al. |
| 2019/0111237 A1 | 4/2019 | Cabiri et al. |
| 2019/0133666 A1 | 5/2019 | Johnson |
| 2019/0167367 A1 | 6/2019 | Walker et al. |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0254754 A1 | 8/2019 | Johnson |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0336674 A1 | 11/2019 | Schermeier |
| 2019/0365485 A1 | 12/2019 | Kottenstette et al. |
| 2019/0380825 A1 | 12/2019 | Perkins et al. |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0028181 A1 | 1/2020 | Arugula et al. |
| 2020/0054399 A1 | 2/2020 | Duindam |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170630 A1 | 6/2020 | Wong et al. |
| 2020/0242767 A1 | 7/2020 | Zhao et al. |
| 2020/0282186 A1 | 9/2020 | Blacker et al. |
| 2020/0289219 A1 | 9/2020 | Denlinger et al. |
| 2020/0297444 A1 | 9/2020 | Camarillo et al. |
| 2020/0297973 A1 | 9/2020 | Blacker et al. |
| 2020/0306064 A1 | 10/2020 | Perkins et al. |
| 2020/0316340 A1 | 10/2020 | Wenderow et al. |
| 2020/0324084 A1 | 10/2020 | Falb et al. |
| 2020/0338308 A1 | 10/2020 | Saber et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0376249 A1 | 12/2020 | Lockhart |
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2020/0405950 A1 | 12/2020 | Burren |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0046284 A1 | 2/2021 | Mauch |
| 2021/0060767 A1 | 3/2021 | Guerrera et al. |
| 2021/0068852 A1 | 3/2021 | Spence |
| 2021/0077211 A1 | 3/2021 | Blacker et al. |
| 2021/0093406 A1 | 4/2021 | Blacker et al. |
| 2021/0100980 A1 | 4/2021 | Blacker |
| 2021/0106393 A1 | 4/2021 | Simi et al. |
| 2021/0145532 A1 | 5/2021 | Tucker et al. |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0192759 A1 | 6/2021 | Lang |
| 2021/0196242 A1 | 7/2021 | Perez |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0244434 A1 | 8/2021 | Popa et al. |
| 2021/0247396 A9 | 8/2021 | Penny |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0290327 A1 | 9/2021 | Yates et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0315596 A1 | 10/2021 | Buck et al. |
| 2021/0353129 A1 | 11/2021 | Roelle et al. |
| 2021/0361366 A1 | 11/2021 | Murphy et al. |
| 2021/0369370 A1 | 12/2021 | Malanoski |
| 2021/0378696 A1 | 12/2021 | Yang et al. |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0047344 A1 | 2/2022 | Stepanauskas |
| 2022/0047849 A1 | 2/2022 | Yee et al. |
| 2022/0096120 A1 | 3/2022 | Bajo et al. |
| 2022/0125533 A1 | 4/2022 | Falb |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168049 A1 | 6/2022 | Tanner et al. |
| 2022/0211452 A1 | 7/2022 | Clark et al. |
| 2022/0233263 A1 | 7/2022 | Canale et al. |
| 2022/0233264 A1 | 7/2022 | Klem |
| 2022/0233820 A1 | 7/2022 | Clark et al. |
| 2022/0241490 A1 | 8/2022 | Marass |
| 2022/0313375 A1 | 10/2022 | Zhang et al. |
| 2022/0323096 A1 | 10/2022 | Naglretter et al. |
| 2022/0331509 A1 | 10/2022 | Buck et al. |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |

(56) References Cited

U.S. PATENT DOCUMENTS

| | | |
|---|---|---|
| 2023/0035508 A1 | 2/2023 | Clark et al. |
| 2023/0035946 A1 | 2/2023 | Kapadia |
| 2023/0043432 A1 | 2/2023 | Kapadia |
| 2023/0048388 A1 | 2/2023 | Lau et al. |
| 2023/0052862 A1 | 2/2023 | Lau et al. |
| 2023/0061728 A1 | 3/2023 | Davis et al. |
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0209018 A1 | 6/2023 | Alexanderson et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2023/0355299 A1 | 11/2023 | Cosman |
| 2023/0380914 A1 | 11/2023 | Meglan et al. |
| 2023/0380915 A1 | 11/2023 | Hundertmark |
| 2024/0001101 A1 | 1/2024 | Wallin et al. |
| 2024/0016557 A1 | 1/2024 | Hung et al. |
| 2024/0016560 A1 | 1/2024 | Canale et al. |
| 2024/0019042 A1 | 1/2024 | Lim |
| 2024/0032949 A1 | 2/2024 | Yang et al. |
| 2024/0033017 A1 | 2/2024 | Yang et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0130809 A1 | 4/2024 | Scheunert et al. |
| 2024/0138862 A1 | 5/2024 | Beach |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180650 A1 | 6/2024 | Lau et al. |
| 2024/0180651 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181224 A1 | 6/2024 | Lau et al. |
| 2024/0181298 A1 | 6/2024 | Lau et al. |
| 2024/0183382 A1 | 6/2024 | Lau et al. |
| 2024/0197416 A1 | 6/2024 | Gonzalez |
| 2024/0197418 A1 | 6/2024 | Jourdan |
| 2024/0198051 A1 | 6/2024 | Jourdan |
| 2024/0207570 A1 | 6/2024 | Mar |
| 2025/0032201 A1 | 1/2025 | Bartholomew et al. |
| 2025/0177692 A1 | 6/2025 | Yee et al. |
| 2025/0195835 A1 | 6/2025 | Totten |
| 2025/0261956 A1 | 8/2025 | Ray et al. |
| 2025/0319243 A1 | 10/2025 | Mar |
| 2025/0352717 A1 | 11/2025 | Bartholomew |
| 2025/0375256 A1 | 12/2025 | Berry |
| 2025/0375592 A1 | 12/2025 | Dan |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |

(56) References Cited

FOREIGN PATENT DOCUMENTS

| WO | WO 2021/127426 | 6/2021 |
| WO | WO 2021/183444 | 9/2021 |
| WO | WO 2021/184444 | 9/2021 |
| WO | WO 2022/048984 | 3/2022 |
| WO | WO 2022/115717 | 6/2022 |
| WO | WO 2022/154979 | 7/2022 |
| WO | WO 23/110598 | 6/2023 |

OTHER PUBLICATIONS

US 12,108,960 B1, 10/2024, Teigen et al. (withdrawn)

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904.11102v1 [cs.RO], 8 pp.

Bergman et al., 2020, Robotic assisted percutaneous coronary interventions, in Handbook of Robotic and Image Guided Surgery, Elsevier Inc., pp. 341-362.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv: 1902.08164v1 [cs.RO], 19 pp.

Das et al., May 29, 2020, Stochastic Modeling of Distance to Collision for Robot Manipulators, arXiv:2005.14391v1 [cs.RO], 8 pp.

Evard, Jun. 2018, Catheter localization utilizing a sensor-enabled guidewire design of a proof-of- concept system, Masters Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008.05112v1 [cs.RO}, 7 pp.

Kagiyama et al., Jul. 31, 2019, First experience of robotic-assisted percutaneous coronary intervention in Japan, Intern Med Advance Publication, doi: Oct. 2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv: 1809.05645v1 [cs. CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1 - 1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

International Search Report and Written Opinion dated Apr. 30, 2024 in application No. PCT/US2023/081823.

* cited by examiner

142

$$C = e_0 \times \frac{A}{d} \, (F)$$

Side View of Puck and Carriage

Equivalent System

4102

4012

4124

4124

4120

4120

4026  4028

METHOD FOR USING A TELESCOPING DRIVE TABLE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57. The present application claims priority to U.S. Provisional Patent Application No. 63/385,761, filed Dec. 1, 2022, titled TELESCOPING DRIVE TABLE, the entire content of which is incorporated by reference herein for all purposes and forms a part of this specification.

BACKGROUND

Field

The present application relates to neurovascular procedures, and more particularly, to catheter assemblies and robotic control systems for neurovascular site access.

Description of the Related Art

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to energy storage and release caused by frictional interplay between coaxial shafts and the patient's vasculature. Supra-aortic access necessary to reach the neurovasculature is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

There is provided in accordance with one aspect of the present disclosure a supra-aortic access robotic control system. The system includes a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter. The access catheter hub may also laterally deflect a distal deflection zone of the access catheter. The guidewire hub may additionally be configured to laterally deflect a distal portion of the guidewire. The guidewire hub may be configured to adjust the guide catheter in a rotational direction.

There may also be provided a procedure catheter hub configured to manipulate a procedure catheter. Following robotic placement of the guidewire, access catheter and guide catheter such that the guide catheter achieves supra aortic access, the guidewire and access catheter may be proximally withdrawn and the procedure catheter advanced through and beyond the guide catheter, with or without guidewire support (said guidewire may be smaller in diameter and/or more flexible than the guidewire used to gain supra aortic access), to reach a more distal neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, an ablation catheter, an RF ablation catheter or guidewire, a balloon catheter, or a microcatheter used to deliver a stent retriever, a balloon catheter or a stent retriever.

The control system may further include a driven magnet on each of a guidewire hub, an access catheter hub and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may include a tray made from a thin polymer membrane, or any membrane of non-ferromagnetic material.

The control system may further include a control console which may be connected to the support table or may be located remotely from the support table. The position of each driven magnet and corresponding hub is movable in response to manual manipulation of a guidewire drive control, access catheter drive control, or procedure catheter drive control on the console or on a particular controller not associated with the console.

The control system may further include a processor for controlling the position of the drive magnets. The processor may be in wired communication with the control console, or in wireless communication with the control console. The driven magnets may be configured to remain engaged with the corresponding drive magnets until application of an axial disruption force of at least about 300 grams. In some embodiments, the nominal driving force is at least 15 N or 1500 grams.

There is also provided a robotically driven interventional device. The device includes an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. In some embodiments, at least one control element may be an axially movable tubular body or fiber, ribbon, or wire such as a pull wire extending through the interventional device to, for example, a distal deflection zone. In some embodiments, any number of control elements may be advanced, retracted, or otherwise moved in a similar manner.

There is also provided a control system for controlling movement of interventional devices. In one configuration, the control system includes a guidewire control, configured to control axial travel and rotation of a guidewire; an access catheter control, configured to control axial and rotational movement of an access catheter; and a guide catheter control, configured to control axial movement and/or rotation of a guide catheter.

The control system may further include a deflection control, configured to control deflection of the access catheter or procedure catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further include a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further include a graphical user interface with at least one display for indicating the status of at least one device parameter, and/or indicating the status of at least one patient parameter.

There is also provided a sterile packaging assembly for transporting interventional devices to a robotic surgery site. The packaging assembly may include a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient. In some embodiments, the support table is a drive table. An upper surface of the base can be within a sterile field, and a lower surface of the base can be outside of the sterile field.

Any of the hubs disclosed herein may further include a fluid injection port and/or a wireless RF transceiver for communications and/or power transfer. The hub may include a visual indicator, for indicating the presence of a clot. In some embodiments, the hub may also include wired electrical communications and power port. The visual indicator may include a clot chamber having a transparent window. A filter may be provided in the clot chamber.

Any of the hubs disclosed herein may further include a sensor for detecting a parameter of interest such as the presence of a clot. The sensor, in some instances, may be positioned on a flexible body. The sensor may include a pressure sensor or an optical sensor. In some embodiments, the sensor may include one or more of a force sensor, a positioning sensor, a temperature sensor, and/or an oxygen sensor. In some embodiments, the sensor may include a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each include one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method includes the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally include advancing the procedure catheter hub to position a distal end of the procedure catheter at a neurovascular treatment site. The driving the access catheter step may include driving the access catheter distally through a guide catheter. The driving the access catheter step may include the step of laterally deflecting a distal region of the access catheter to achieve supra-aortic access. In some embodiments, the driving the access catheter step may also include rotating the access catheter.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guidewire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may include magnetically coupling a hub on each of the guidewire, access catheter and guide catheter, to separate corresponding couplers carrying corresponding drive magnets independently movably carried by the drive table. The procedure assembly may include a guidewire, a first catheter and a second catheter. The guidewire and first catheter may be positioned concentrically within the second catheter. The procedure assembly may be advanced as a unit through at least a portion of the length of the guide catheter, and the procedure may include a neurovascular thrombectomy.

There is also provided a method of performing a neurovascular procedure. The method includes the steps of providing a multi-catheter assembly including an access catheter, a guide catheter, and a procedure catheter, coupling the assembly to a robotic drive system, driving the assembly to achieve supra-aortic access, driving a subset of the assembly to a neurovascular site, wherein the subset includes the guide catheter and the procedure catheter, proximally removing the access catheter, and performing a neurovascular procedure using the procedure catheter.

The neurovascular procedure can include a neurovascular thrombectomy. The assembly may further include a guidewire, wherein each of the guidewire, the access catheter, the guide catheter, and the procedure catheter are configured to be adjusted by a respective hub. Coupling the assembly to the robotic drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The first drive magnet, the second drive magnet, the third drive magnet, and the fourth drive magnet can each be independently movably carried by a drive table. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

There is also provided a method of performing a neurovascular procedure. The method includes the steps of providing an assembly including a guidewire, an access catheter, a guide catheter, and a procedure catheter coaxially moveably assembled into a single multi-catheter assembly, coupling the assembly to a drive system, driving the assembly to achieve supra-aortic access, driving a subset of the assembly to an intracranial site, wherein the subset includes the guidewire, the guide catheter, and the procedure catheter, and performing a neurovascular procedure using the subset of the assembly.

Each of the guidewire, the access catheter, the guide catheter, and the procedure catheter can be configured to be adjusted by a respective hub. Coupling the assembly to the drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The drive system can be a robotic drive system, and the first drive magnet, the second drive magnet, the third drive magnet, and the fourth drive magnet can each be independently movably carried by a drive table associated with the robotic drive system. The first drive magnet, the second drive magnet, the third drive magnet, and the fourth drive magnet can each be independently movably carried by a drive table.

There is also provided a method of performing a neurovascular procedure. The method includes providing an assembly including a guidewire having a guidewire hub, an access catheter having an access catheter hub, and a guide catheter having a guide catheter hub. The method also includes coupling the guidewire hub to a first hub adapter, the access catheter hub to a second hub adapter, and the guide catheter hub to a third hub adapter, wherein each of the first hub adapter, the second hub adapter and the third hub adapter is movably carried by a support table. The method also includes driving the assembly in response to movement of each of the first hub adapter, the second hub adapter and the third hub adapter along the support table until the assembly is positioned to achieve supra-aortic vessel access.

The method can include the step of driving a subset of the assembly along the support table until the subset of the assembly is positioned to perform a neurovascular procedure at a neurovascular treatment site, wherein the subset of the assembly includes the guidewire, the guide catheter, and a procedure catheter. The neurovascular procedure can include a thrombectomy. Coupling the guidewire hub to the first hub adapter can include magnetically coupling the guidewire hub to a first drive magnet. Coupling the access catheter hub to the second hub adapter can include magnetically coupling the access catheter hub to a second drive magnet. Coupling the guide catheter hub to the third hub adapter can include magnetically coupling the guide catheter hub to a third drive magnet. The first drive magnet, the second drive magnet and the third drive magnets can be independently movably carried by the support table. The first drive magnet can be coupled to a first driven magnet across a sterile field barrier. The second drive magnet can be coupled to a second driven magnet across the sterile field barrier. The third drive magnet can be coupled to a third driven magnet across the sterile field barrier. Coupling the guidewire hub to the first hub adapter can include mechanically coupling the guidewire hub to a first drive. Coupling the access catheter hub to the second hub adapter can include mechanically coupling the access catheter hub to a second drive. Coupling the guide catheter hub to the third hub adapter can include mechanically coupling the guide catheter hub to a third drive. The guidewire and the guide catheter can be advanced as a unit along at least a portion of a length of the access catheter after supra-aortic access is achieved. The guidewire hub can be configured to adjust an axial position and a rotational position of the guidewire. The assembly can further include a procedure catheter having a procedure catheter hub. The procedure catheter hub can be configured to adjust an axial position and a rotational position of the procedure catheter. The procedure catheter hub can be further configured to laterally deflect a distal deflection zone of the procedure catheter. The guidewire hub can be configured to adjust an axial position and a rotational position of the guidewire. The procedure catheter hub can be configured to adjust an axial position and a rotational position of the procedure catheter. The guide catheter hub can be configured to adjust an axial position of the guide catheter. The access catheter hub can be configured to adjust an axial position and a rotational position of the access catheter. The procedure catheter hub can be further configured to laterally deflect a distal deflection zone of the procedure catheter. The access catheter hub can be further configured to laterally deflect a distal deflection zone of the access catheter. The guide catheter hub can be configured to adjust an axial position of the guide catheter. The guide catheter hub can be configured to adjust a rotational position of the guide catheter. The access catheter hub can be configured to adjust an axial position and a rotational position of the access catheter. The access catheter hub can be further configured to laterally deflect a distal deflection zone of the access catheter.

There is also provided a drive system for achieving supra-aortic access and neurovascular treatment site access. The system includes a guidewire hub configured to adjust an axial position and a rotational position of a guidewire, a procedure catheter hub configured to adjust an axial position and a rotational position of a procedure catheter, a guide catheter hub configured to adjust an axial position of a guide catheter, and an access catheter hub configured to adjust an axial position and a rotational position of an access catheter, the access catheter further configured to laterally deflect a distal deflection zone of the access catheter.

The procedure catheter hub can be further configured to laterally deflect a distal deflection zone of the procedure catheter. The guidewire hub can be configured to couple to a guidewire hub adapter by magnetically coupling the guidewire hub to a first drive magnet. The access catheter hub can be configured to couple to an access catheter hub adapter by magnetically coupling the access catheter hub to a second drive magnet. The guide catheter hub can be configured to couple to a guide catheter hub adapter by magnetically coupling the guide catheter hub to a third drive magnet. The procedure catheter hub can be configured to couple to a procedure catheter hub adapter by magnetically coupling the procedure catheter hub to a fourth drive magnet. The first drive magnet, the second drive magnet, the third drive magnet, and the fourth drive magnet can be independently movably carried by a drive table. The system can include first driven magnet on the guidewire hub configured to cooperate with the first drive magnet such that the first driven magnet moves in response to movement of the first drive magnet. The first drive magnet can be configured to move outside of a sterile field while separated from the first driven magnet by a sterile field barrier while the first driven magnet is within the sterile field. A position of the first drive magnet can be movable in response to manipulation of a procedure drive control on a control console in electrical communication with the drive table. The system can include a second driven magnet on the access catheter hub configured to cooperate with the second drive magnet such that the second driven magnet is configured to move in response to movement of the second drive magnet, wherein the second drive magnet is configured to move outside of the sterile field while separated from the second driven magnet by the barrier while the second driven magnet is within the sterile field. The system can include a third driven magnet on the guide catheter hub configured to cooperate with the third drive magnet such that the third driven magnet is configured to move in response to movement of the third drive magnet, wherein the third drive magnet is configured to move outside of the sterile field while separated from the third driven magnet by the barrier while the third driven magnet is within the sterile field. The system can include a fourth driven magnet on the procedure catheter hub configured to cooperate with the fourth drive magnet such that the fourth driven magnet is configured to move in response to movement of the fourth drive magnet, wherein the fourth drive magnet is configured to move outside of the sterile field while separated from the fourth driven magnet by the barrier while the fourth driven magnet is within the sterile field. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a balloon catheter. The procedure catheter can be a catheter to facilitate percutaneous valve repair or replacement. The procedure catheter can be an ablation catheter.

There is also provided method of achieving supra-aortic access and neurovascular treatment site access. The method includes the steps of providing a drive system including a guidewire hub configured to adjust an axial position and a rotational position of a guidewire, a procedure catheter hub configured to adjust an axial position and a rotational position of a procedure catheter; a guide catheter hub configured to adjust an axial position of a guide catheter, and an access catheter hub configured to adjust an axial position and a rotational position of an access catheter, the access catheter further configured to laterally deflect a distal deflection zone of the access catheter, and moving at least one of the guidewire hub, the procedure catheter hub, the guide catheter hub, and the access catheter hub to drive movement of at least one of the guidewire, the procedure catheter, the guide catheter, and the access catheter. The method can further include controlling the procedure catheter hub to laterally deflect a distal deflection zone of the procedure catheter.

There is also provided a method of achieving supra aortic access. The method includes the steps of providing an assembly including a guidewire, an access catheter and a guide catheter, coaxially moveably assembled into a single multi-catheter assembly, coupling the assembly to a drive system, driving the assembly to an aortic arch, and advancing the access catheter to achieve supra-aortic access to a branch vessel off of the aortic arch.

The method can further include driving a subset of the assembly to an intracranial site, and performing a neurovascular procedure using the subset of the assembly. The subset can include the guidewire, the guide catheter, and a procedure catheter. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter. The intracranial procedure can include an intracranial thrombectomy. The neurovascular procedure can include a neurovascular thrombectomy. At least one of the guidewire, the access catheter, and the guide catheter can include a hub configured to couple to a robotic drive system. Coupling the assembly to the drive system can include magnetically coupling a guide catheter hub to the drive system. Coupling the assembly to the drive system can include mechanically coupling a guide catheter hub to the drive system. The drive system can be a robotic drive system, and at least a first drive magnet, a second drive magnet, and a third drive magnet are each independently movably carried by a drive table associated with the robotic drive system.

There is also provided a robotic drive system. The robotic drive system, includes a base structure; a drive table coupled with the base structure and configured to move axially; a first hub adapter coupled with the drive table, the first hub adapter being coupleable with a first hub coupleable with a first interventional device; and a second hub adapter coupled with the drive table, the second hub adapter configured to move a second hub coupleable with a second interventional device axially along the drive table.

The robotic drive system can include an arm coupled with the base structure and the drive table, the arm configured to move the drive table relative to the base structure in an axial direction and/or in a vertical direction. The arm can be further configured to move the drive table in an orthogonal direction, wherein the orthogonal direction can be orthogonal to the axial direction and can be orthogonal to the vertical direction. The drive table can be configured to rotate between at least a first position in which the drive table can be generally parallel to a ground surface and at least a second position that can be orthogonal to the first position. The drive table can be configured to move in a vertical direction from at least a first height from a ground surface to at least a second height from the ground surface, wherein the second height can be greater than the first height. The first hub adapter can be fixed to the drive table such that the first hub adapter cannot move relative to the drive table. The robotic drive system can be configured to move the first hub adapter in at least a first axial direction relative to a patient reference point by maintaining the first hub adapter in a fixed position on the drive table and moving the drive table in the first axial direction relative to the patient reference point. The robotic drive system can be configured to maintain the second hub adapter in a fixed position relative to the patient reference point when the drive table can be moved relative to the patient reference point by moving the second hub adapter relative to the drive table in a direction that is opposite to a movement of the drive table relative to the patient reference point. The robotic drive system can be configured to maintain the second hub adapter in a fixed position relative to a patient reference point when the drive table is moved in the first axial direction relative to the patient reference point by moving the second hub adapter in a second axial direction relative to the drive table that is opposite to the first axial direction as the drive table is moved in the first axial direction. The robotic drive system can be configured to move the second hub adapter independently of the first hub adapter. The robotic drive system can include a third hub adapter coupled with the drive table and a fourth hub adapter coupled with the drive table; wherein the third hub adapter can be configured to move a third hub coupleable with a third interventional device axially along the drive table; wherein the fourth hub adapter can be configured to move a fourth hub coupleable with a fourth interventional device axially along the drive table; and wherein the second hub adapter can be distal to the third hub adapter and the third hub adapter can be distal to the fourth hub adapter. The second, third, and fourth hub adapters can each be independently movable axially relative to the drive table. The second hub adapter can be axially aligned with the first hub adapter such that a first interventional device coupled with the first hub and a second interventional device coupled with the second hub can be coaxially aligned when the first and second hubs are coupled with the first and second hub adapters, respectively. The second hub adapter can be axially aligned with the first hub adapter such that a first interventional device coupled with the first hub and a second interventional device coupled with the second hub can be coaxially aligned when the first and second hubs can be magnetically coupled with the first and second hub adapters, respectively. The arm can include a first arm segment coupled at a proximal end thereof directly or indirectly to the base structure, a second arm segment coupled at a proximal end thereof to a distal end of the first arm segment, and a third arm segment coupled at a proximal end thereof to a distal end of the second arm segment. The arm can include a first joint at a proximal end of the first arm segment, a second joint at a distal end of the first arm segment, and a third joint at a distal end of the second arm segment, wherein the first arm segment can be configured to rotate in a horizontal plane about the first joint; the second arm segment can be configured to rotate in a horizontal plane about the second joint; and the third arm segment can be configured to rotate in a horizontal plane about the third joint. The first, second, and third joints can be configured to independently exert a torque on the first, second, and third arm segments in response to an input provided by a user of the robotic drive system to cause the first, second, and third arm segments to rotate about the first, second, and third joints, respectively. The first joint, the second joint, and the third joint can be configured to be switched between a passive state wherein the joint can be freely manually moved and an active state wherein the joint can be configured to generate a torque force. The robotic drive system can include a fourth arm segment coupled at a proximal end thereof to a distal end of the third arm segment and a fourth joint at a distal end of the third arm segment, wherein the fourth arm segment can be configured to rotate in a horizontal plane about the fourth joint. The fourth arm segment can be coupled at a distal end thereof directly or indirectly to the drive table. The robotic drive system can include a fifth joint at a distal end of the fourth arm segment, wherein the drive table can be coupled to the fifth joint and the fifth joint can be configured to rotate the drive table in vertical plane about the fifth joint. One or more of the joints can include a selectable brake element that can be actuated to lock a joint in a fixed position, wherein the brake can be actuated manually or electronically. The first hub adapter and/or the second hub adapter can be configured to move axially relative to the drive table in response to an input provided by a user of the robotic drive system. The first hub adapter and the second hub adapter can be configured to independently move in an axial direction relative to the drive table in response to an input provided by a user of the robotic drive system. The first hub adapter and/or the second hub adapter can be configured to move axially relative to the drive table on a rack and pinion linear actuator in response to an input provided by a user of the robotic drive system. The second hub adapter, the third hub adapter, and the fourth hub adapter can each be configured to move axially relative to the drive table via a rack and pinion linear actuator, wherein each of the second hub adapter, the third hub adapter, and the fourth hub adapter can include an independently controllable motor. The second hub adapter, the third hub adapter, and the fourth hub adapter can each include an encoder configured to provide position data that can be used by a controller of the robotic drive system to determine a position of each of the second hub adapter, the third hub adapter, and the fourth hub adapter. Each of the joints can have an encoder configured to provide position data that can be used by the controller to determine a position of the respective joint and a position of the drive table. The first hub adapter and/or the second hub adapter can have a plurality of wheels configured to move along one or more rails of the drive table. The first hub adapter and/or the second hub adapter can be configured to move axially relative to the drive table using a belt drive system, a lead screw system, or a ball screw system. The drive table can be foldable to reduce an overall length of the drive table in a stowed configuration. The robotic drive system can include a support bracket extending distally in an axial direction away from a distal end of the drive table and an anti-buckling element coupled at a distal end thereof with the support bracket, the anti-buckling element can be configured to stiffen a portion of an interventional device supported by the drive table spanning from the drive table to a boss clip supported by the support bracket, wherein the boss clip can be coupled to a femoral sheath. The support bracket can be configured to couple the anti-buckling element to a flexible sheath sleeve that can be configured to couple with the femoral sheath. The robotic drive system can include a linear actuator configured to move the drive table relative to the base structure in response to an input provided by a user of the robotic drive system. The linear actuator can include a rack and pinion actuator including a rack that extends from a proximal end of the drive table along a majority of a length of the drive table and a motor supported by the base structure having a pinion gear thereon that can be configured to engage the rack and to move the drive table axially relative to the base structure. The rack can extend from a proximal end of the drive table along at least 70% of a length of the drive table. The rack can extend from a proximal end of the drive table along at least 80% of a length of the drive table. The rack can extend from a proximal end of the drive table along at least from 60% or approximately 60% to 90% or approximately 90% of a length of the drive table. The drive table can be configured to be movable in an axial direction between a proximal position and a distal position, wherein a distance between a distal end of the drive table in the proximal position and the distal end of the drive table in the distal position can be at least 80% of a length of the drive table from a proximal end of the drive table to the distal end of the drive table. The first hub adapter can include a drive magnet coupled with the first hub adapter and can be configured to couple with a driven magnet of the first hub such that the driven magnet can move in response to a movement of the drive magnet, and the second hub adapter can include a drive magnet coupled with the second hub adapter and can be configured to couple with a driven magnet of the second hub such that the driven magnet of the second hub can move in response to a movement of the drive magnet of the second hub adapter. The robotic drive system can include a first sensor coupled with the first hub adapter or the first hub, the first sensor can be configured to measure a magnitude of a magnetic field on the first sensor from the drive magnet of the hub adapter and/or the driven magnet of the first hub. The first sensor can be a magnetometer. The drive magnet and driven magnet magnetically can couple the hub adapter to the hub when the hub is within a predetermined distance of the hub adapter in an axial direction. The base structure can be configured to be coupled with a surgical bed. The base structure can be configured to be mounted to a ground surface. The robotic drive system can include a controller or control circuit configured to control a position and a movement of the drive table, the first hub adapter, and the second hub adapter. The arm can include three or more, or four rotational degrees of freedom. The drive table can include a support surface positioned between the first and second hub adapters and the first and second hubs, the support surface can be oriented at an angle relative to a horizontal plane.

There is also provided a robotic drive system. The robotic drive system can include a drive table including: a main body; and an extendable member configured to be at least partially received within the main body and being extendable from a proximal end or a distal end of the main body; and one or more hub adapters coupled with the drive table, each of the one or more hub adapters configured to couple to a corresponding hub so that axial movement of the each of the one or more hub adapters drives axial movement of the corresponding hub, the one or more hub adapters comprising a first hub adapter configured to couple to a first hub so that axial movement of the first hub adapter drives axial movement of the first hub, wherein the first hub adapter can be configured to translate from a first axial position within the main body to a second axial position within the extendable member beyond the proximal end or the distal end of the main body.

The first hub adapter can be configured to drive movement of the first hub from a first axial position on a drive surface of the main body to a second axial position on a drive surface of the extendable member. The first hub can be a guide catheter hub. The one or more hub adapters can include: a second hub adapter configured to couple to a procedure catheter hub; and a third hub adapter configured to couple to an access catheter hub. The one or more hub adapters can include a fourth hub adapter configured to couple to a guidewire hub. The extendable member can be extendable from the distal end of the main body. The first hub can be a guidewire hub. The extendable member can be extendable from the proximal end of the main body. The robotic drive system can further include a shuttle configured to move axially within the main body and the extendable member, wherein the one or more hub adapters can be configured to move axially along the shuttle. The drive table can include: a first linear actuator assembly configured to control axial movement of the shuttle within the main body and the extendable member; a second linear actuator assembly configured to control axial movement of the one or more hub adapters relative to the shuttle; and a third linear actuator assembly configured to control axial movement of the extendable member. The robotic drive system can further include a cable management system configured to position one or more cables within an interior section of the shuttle. The robotic drive system can further include one or more motors configured to drive the one or more hub adapters axially along the shuttle, wherein the cable management system can be configured to prevent engagement of the one or more cables with the one or more motors. The extendable member can be a first extendable member, the first extendable member can be extendable from the distal end of the main body, wherein the drive table can further include a second extendable member extendable from the proximal end of the main body. Each of the first extendable member and the second extendable member can have a length of about half of a length of the main body. The one or more hub adapters can include a second hub adapter to translate from a first axial position within the main body to a second axial position within the second extendable member beyond the proximal end of the main body. The robotic drive system can further include: a base structure; and an arm coupled with the base structure and the drive table, the arm configured to move the drive table relative to the base structure in an axial direction and/or in a vertical direction. The drive table can include a drive surface oriented at an angle relative to a horizontal plane.

There is also provided a method of driving an interventional device assembly. The method of driving the interventional device assembly can include: axially advancing an extendable member from a proximal end or a distal end of a main body of a drive table; and axially advancing a hub adapter from a first axial position within the main body to a second axial position within the extendable member beyond the proximal end or the distal end of the main body, the hub adapter being configured to couple to a corresponding hub so that axial movement of the hub adapter drives axial movement of the corresponding hub.

The hub adapter can be configured to drive movement of the hub from a first axial position on a drive surface of the main body to a second axial position on a drive surface of the extendable member. The hub can be a guide catheter hub. The hub adapter can be a first hub adapter, the method can further include: axially advancing a second hub adapter configured to couple to an access catheter; and axially advancing a third hub adapter configured to couple to a procedure catheter. The method can further include axially advancing a fourth hub adapter configured to couple to a guidewire hub. The extendable member can be extendable from the distal end of the main body. The hub can be a guidewire hub. The extendable member can be extendable from the proximal end of the main body. The method can further include a shuttle configured to move axially within the main body and the extendable member, wherein the hub adapter can be configured to move axially along the shuttle. The drive table can include: a first linear actuator assembly configured to control axial movement of the shuttle within the main body and the extendable member; a second linear actuator assembly configured to control axial movement of the hub adapter relative to the shuttle; and a third linear actuator assembly configured to control axial movement of the extendable member. The drive table can further include a cable management system configured to position one or more cables within an interior section of the shuttle. The drive table can further include a motor configured to drive the hub adapter axially along the shuttle, wherein the cable management system can be configured to prevent engagement of the one or more cables with the motor. The extendable member can be a first extendable member, the first extendable member can be extendable from the distal end of the main body, the method can further include axially advancing a second extendable member from the proximal end of the main body of the drive table. Each of the first extendable member and the second extendable member can have a length of about half of a length of the main body. The hub adapter can include a first hub adapter, the method can further include axially advancing a second hub adapter to a first axial position within the main body to a second axial position within the second extendable member beyond the proximal end of the main body. The method can further include moving the drive table relative to a base structure in an axial direction and/or in a vertical direction by an arm coupled with the base structure. The drive table can include a drive surface oriented at an angle relative to horizontal plane.

There is also provided a robotic drive system. The robotic drive system can include: a drive table including a support surface oriented at an angle relative to a horizontal plane; and one or more hub adapters coupled with the drive table, each of the one or more hub adapters being coupleable with a corresponding hub of one or more hubs, each hub being couplable with an interventional device of one or more interventional devices; wherein the support surface can be positioned between the one or more hub adapters and the corresponding hubs.

The support surface can be oriented between 20 and 70 degrees from the horizontal plane. The support surface can be oriented between 50 and 60 degrees from the horizontal plane. The support surface can be oriented 55 degrees from the horizontal plane. The support surface can be oriented between 20 and 70 degrees from a vertical plane. The support surface can be oriented between 40 and 50 degrees from the vertical plane. The support surface can be oriented 35 degrees from the vertical plane. Each of the one or more hub adapters can be magnetically couplable with the corresponding hub. The drive table can include a main body and one or more extendable members. The one or more extendable members can be configured to transition between a collapsed state and a deployed state. wherein the one or more hubs are configured to move axially along the one or more extendable members. The one or more extendable members can include a distal extendable member configured to extend distally from the main body. The one or more extendable members can include a proximal extendable member configured to extend proximally from the main body. At least a portion of at least one of the one or more hubs can be configured to extend laterally and inferiorly relative to an inferior edge of the support surface when the hub is positioned on the support surface. Each of the one or more hub adapters can be configured to move axially along the drive table to drive axial movement of the corresponding hub. At least one of the one or more interventional devices can be configured to be positioned laterally and inferiorly relative to an inferior edge of the support surface when the hub to which the interventional device is coupled is positioned on the support surface. The robotic drive system can include a shuttle configure to translate axially within the drive table, wherein the one or more hub adapters are coupled to the shuttle. The one or more hub adapters are configured to move axially along the shuttle.

There is also included a robotic drive system. The robotic drive system can include: a drive table; a shuttle configured to move axially within the drive table; and one or more hub adapters coupled to the shuttle, the one or more hub adapters being configured to move axially along the shuttle, each of the one or more hub adapters configured to couple to a corresponding hub so that axial movement of the each of the one or more hub adapters drives axial movement of the corresponding hub.

The one or more hub adapters can include: a first hub adapter configured to couple to a guide catheter hub; a second hub adapter configured to couple to a procedure catheter hub; and a third hub adapter configured to couple to an access catheter hub. The one or more hub adapters can further include a fourth hub adapter configured to couple to a guidewire hub. Each of the one or more hub adapters can be configured to magnetically couple to the corresponding hub through a sterile barrier. The robotic drive system can further include: a first linear actuator assembly configured to control axial movement of the shuttle; and a second linear actuator assembly configured to control axial movement of the one or more hub adapters relative to the shuttle. The robotic drive system can further include a cable management system configured to position one or more cables within an interior section of the shuttle. The robotic drive system can further include one or more motors configured to drive the one or more hub adapters axially along the shuttle, wherein the cable management system can be configured to prevent engagement of the one or more cables with the one or more motors. Movement of a proximal most hub adapter of one or more hub adapters can be configured to be temporarily linked to a distal most hub adapter of the plurality of hub adapters so that the proximal most hub adapter and the distal most hub adapter move at a same speed in a same direction. The robotic drive system can further include a control system configured to control movement of the shuttle and the one or more hub adapters in response to a user input. The control system can be configured to cause the shuttle to translate axially by a first distance in a first direction in response to a user input to move the first hub adapter in the first direction. The control system can be configured to cause the second hub adapter to move axially in a second direction opposite of the first direction by a second distance in response to the user input to move the first hub adapter in the first direction, wherein the second distance can be the same as the first distance. The one or more hub adapters can include a first hub adapter and a second hub adapter, wherein the control system can be configured to temporarily link movement of the first hub adapter and the second hub adapter so that the first hub adapter and the second hub adapter move at a same speed in a same direction in response to a user input to move one or both of the first hub adapter and the second hub adapter such that an axial distance between the first hub adapter and the second hub adapters would be greater than an axial length of the shuttle. The drive table can include: a main body; and an extendable member configured to be at least partially received within the main body and can be extendable from a proximal end or a distal end of the main body. The shuttle can be configured to translate from a first axial position within the main body to a second axial position in which at least a portion of the shuttle can be positioned within the extendable member beyond the proximal end or distal end of the main body. The extendable member can be a first extendable member, the first extendable member can be extendable from the distal end of the main body, wherein the drive table can further include a second extendable member extendable from the proximal end of the main body. Each of the first extendable member and the second extendable member can have a length of about half of a length of the main body. The shuttle can be configured to translate from a first axial position within the main body to a second axial position in which at least a portion of the shuttle can be positioned within the first extendable member beyond the distal end of the main body. The shuttle can be configured to translate from a first axial position within the main body to a second axial position in which at least a portion of the shuttle can be positioned within the second extendable member beyond the proximal end of the main body. The shuttle can be configured to translate from a first axial position wherein at least a portion of the shuttle can be positioned in the first extendable member distal to the main body to a second axial position wherein at least a portion of the shuttle is positioned in the second extendable member proximal to the main body.

There is also included a robotic drive system. The robotic drive system can include: a base structure; a drive table coupled with the base structure and configured to rotate between at least a first position in which a longitudinal axis of the drive table can be oriented at a first angle relative to a ground surface and a second position in which the longitudinal axis of the drive table is orientated at a second angle relative to the ground surface, the second angle being different from the first angle.

The longitudinal axis of the drive table in the second position can be perpendicular to the longitudinal axis of the drive table in the first position. The longitudinal axis of the drive table can be parallel to the ground surface in the first position. The drive table can include a planar drive surface extending in a horizontal plane. The robotic drive system can further include an arm coupled with the base structure and the drive table, the arm configured to rotate the drive table about an axis perpendicular to the longitudinal axis of the drive table. The arm can be further configured to move the drive table relative to the base structure in a horizontal direction and/or in a vertical direction relative to the ground surface. The arm can include a first arm segment coupled at a proximal end thereof directly or indirectly to the base structure, a second arm segment coupled at a proximal end thereof to a distal end of the first arm segment, and a third arm segment coupled at a proximal end thereof to a distal end of the second arm segment. The arm can be configured to rotate the drive table in a vertical plane. The arm can include a joint configured to rotate the drive table in the vertical plane, wherein the joint can include a selectable brake that can be actuated to lock the joint in a fixed position. The selectable brake can be actuated manually or electronically. The drive table can include a main body and an extendable member configured to be at least partially received within the main body and can be extendable from a proximal end or a distal end of the main body. The robotic drive system can further include one or more hub adapters coupled with the drive table, each of the one or more hub adapters can be configured to couple to a corresponding hub so that axial movement of the each of the one or more hub adapters drives axial movement of the corresponding hub, the one or more hub adapters can include a first hub adapter configured to couple to a first hub so that axial movement of the first hub adapter drives axial movement of the first hub, wherein the first hub adapter can be configured to translate from a first axial position within the main body to a second axial position within the extendable member beyond the proximal end or the distal end of the main body. The first hub adapter can be configured to drive movement of the first hub from a first axial position on a drive surface of the main body to a second axial position on a drive surface of the extendable member. The robotic drive system can further include a shuttle configured to move axially within the main body and the extendable member, wherein the one or more hub adapters can be configured to move axially along the shuttle. The extendable member can be a first extendable member, the first extendable member can be extendable from the distal end of the main body, wherein the drive table can further include a second extendable member extendable from the proximal end of the main body. Each of the first extendable member and the second extendable member can have a length of about half of a length of the main body. The one or more hub adapters can include a second hub adapter to translate from a first axial position within the main body to a second axial position within the second extendable member beyond the proximal end of the main body. The robotic drive system can further include: a shuttle configured to move axially within the drive table; and one or more hub adapters coupled to the shuttle, the one or more hub adapters can be configured to move axially along the shuttle, each of the one or more hub adapters can be configured to couple to a corresponding hub so that axial movement of the each of the one or more hub adapters drives axial movement of the corresponding hub.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table is positioned over or alongside the patient, and configured to axially advance, retract, and in some cases rotate and/or laterally deflect two or three or more different (e.g., concentrically or side by side oriented) intravascular devices. The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub can be in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device approximately or distally within the patient's vasculature.

The carriages on the drive table, which magnetically couple with the hubs to provide linear motion actuation, are universal. Functionality of the catheters/guidewire are provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
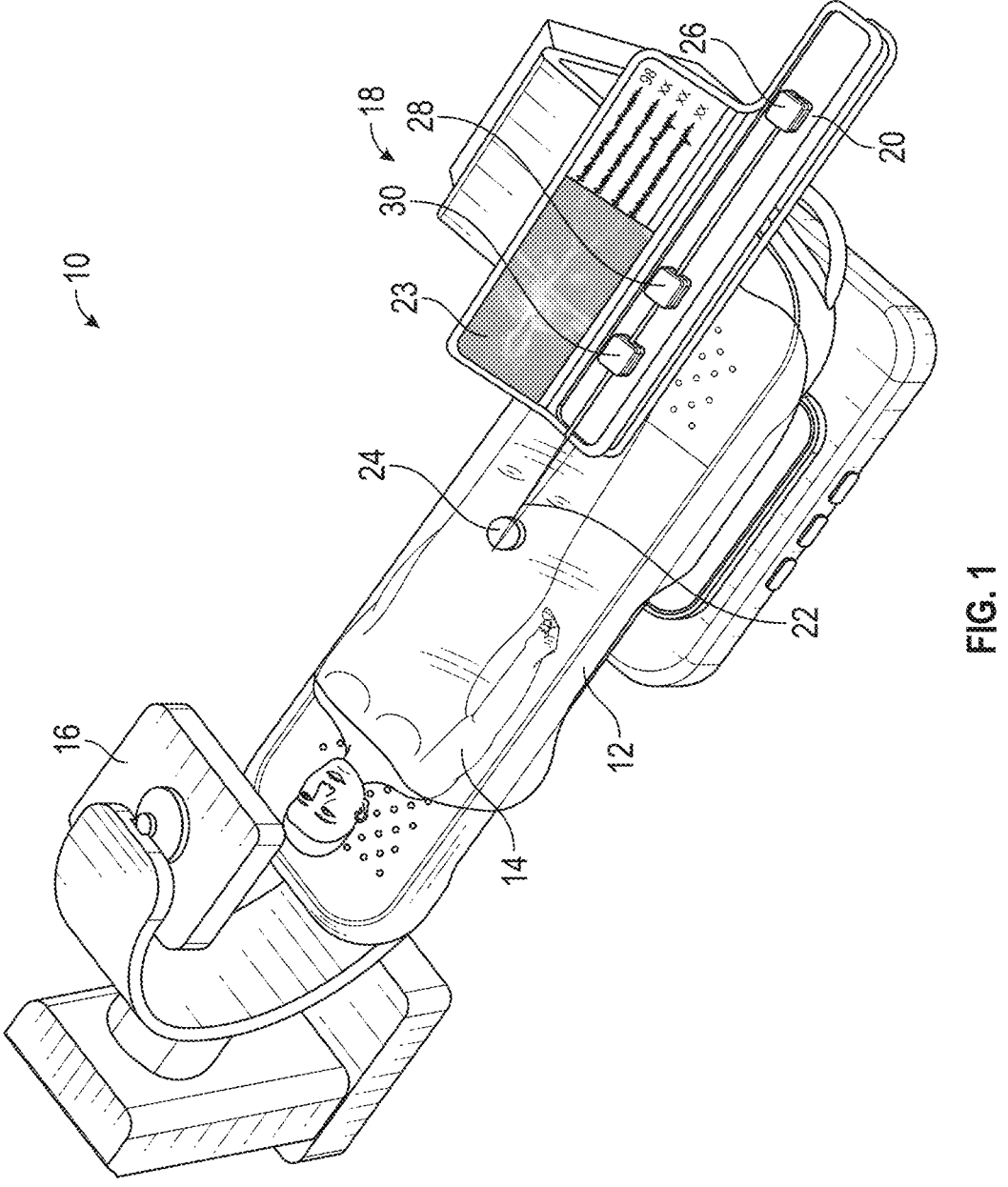
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, in intra-cardiac or structural heart applications, such as valve repair or replacement, or in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
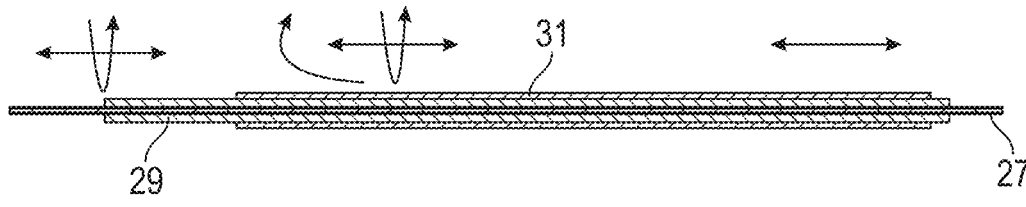
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
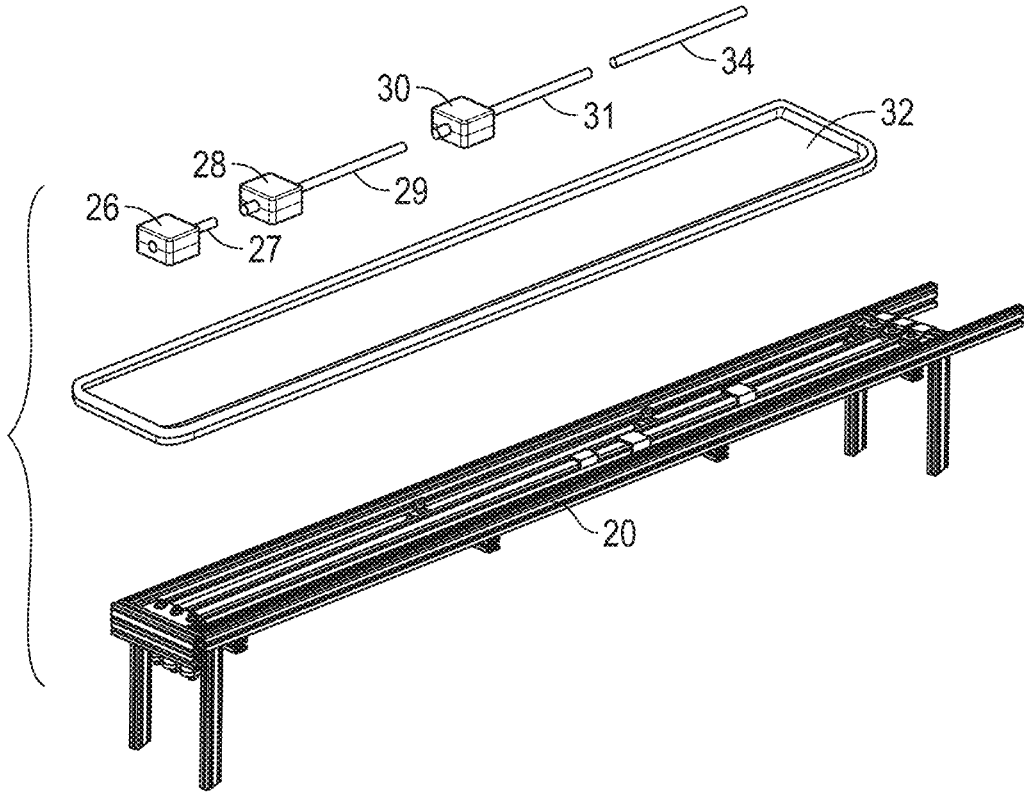
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti-buckling zone for resisting buckling of the portion of the interventional devices spanning the distance between the support table 20 and the femoral artery access point 24. The anti-buckling feature 34 may include a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be a hollow and flexible coating attached to a hub to protect from abrasion, buckling, or damage at the inputs and outputs of the hubs. For example, the hollow, flexible coating may cover a portion of the device shaft when threaded through the hubs. Such a coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypotube, a spring, telescoping tubes, tensioned split tubing, or the like.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK), polyether ketone ketone (PEKK), polyethylenimine (PEI), or polyimide (PI). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough.

The interventional device hubs may be separated from the support table 20 by sterile barrier 32. Sterile barrier 32 may include a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
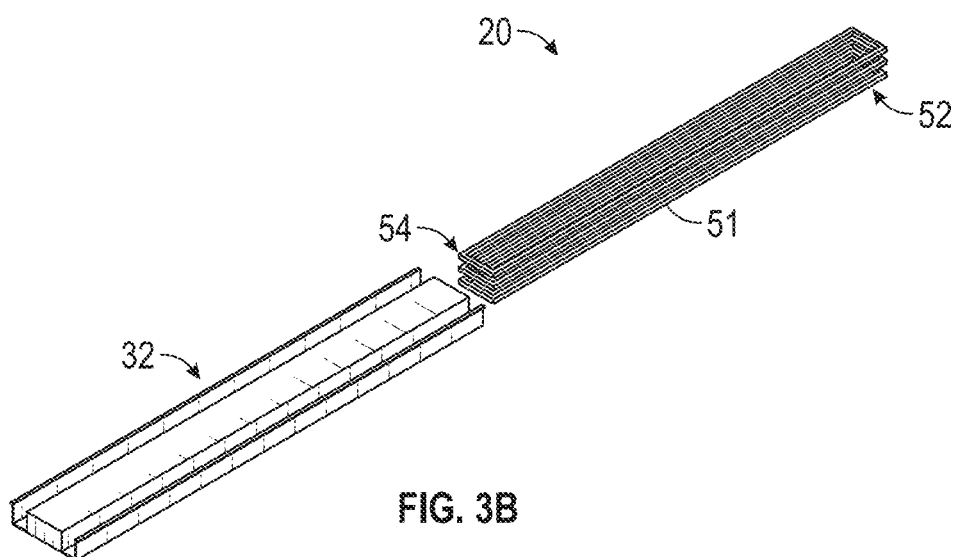
FIGS. 3B-3F show an alternate sterile barrier in the form of a shipping tray having one or more storage channels for carrying interventional devices.
Figure 3C:
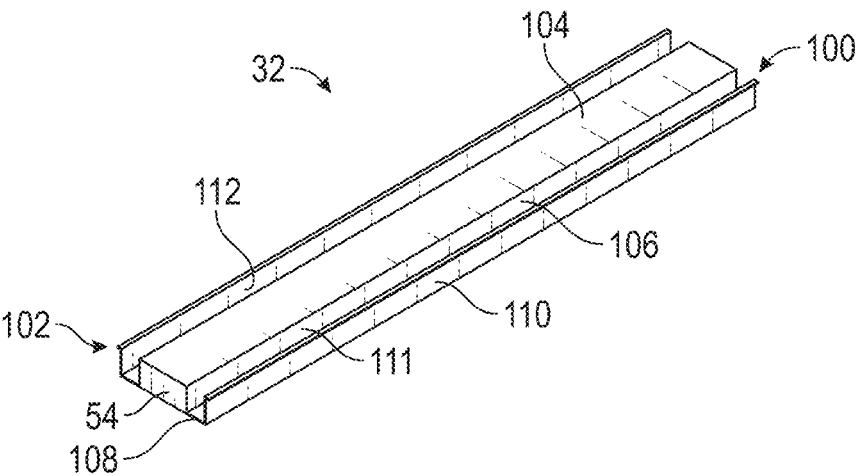

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to about 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figures 3D, 3E, 3F:
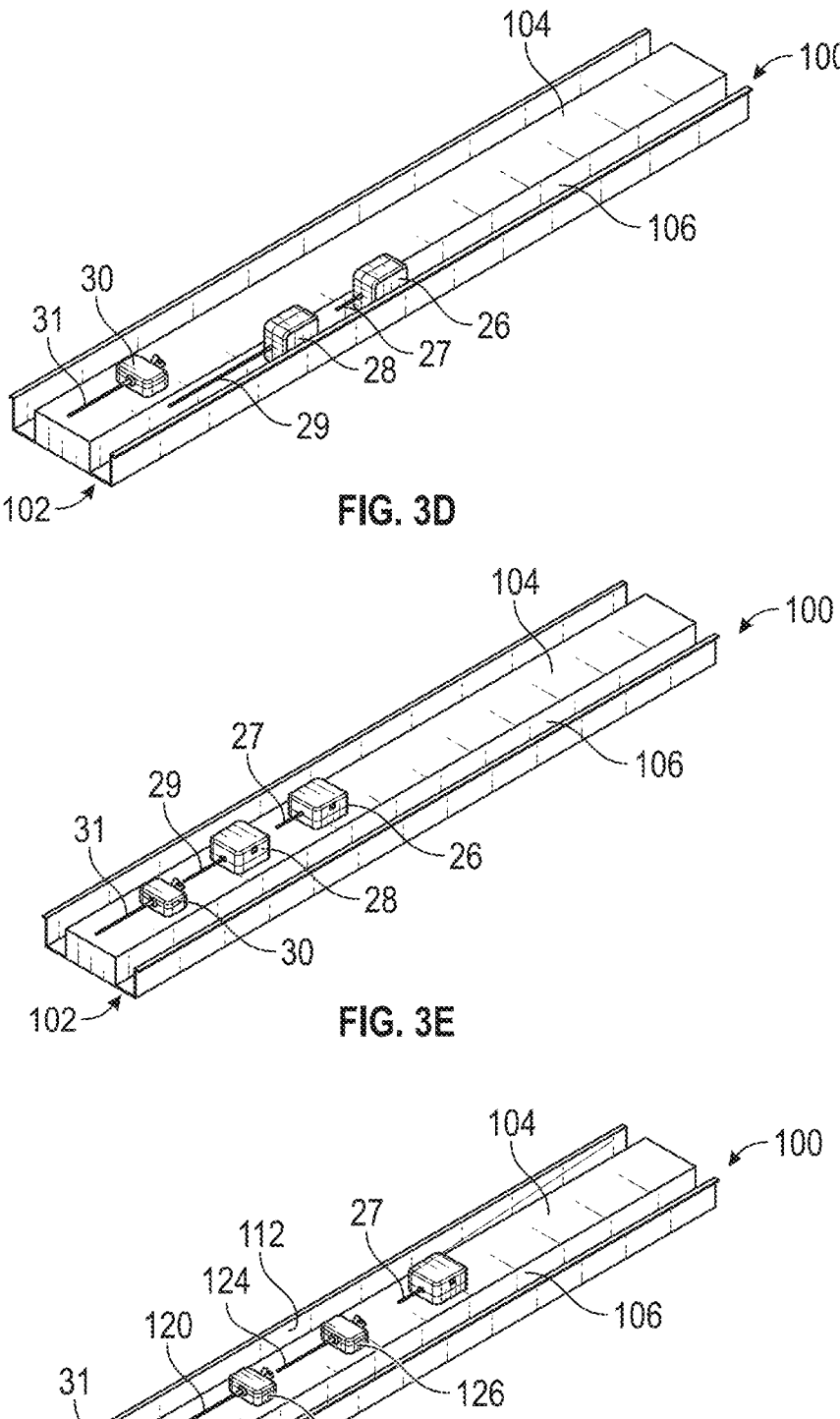

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. This may be accomplished in either a manual or a robotically driven procedure. In one example, the guide catheter 31 may include a catheter having an inner diameter of at least about 0.08 inches and in one implementation about 0.088 inches. The first procedure catheter 120 may include a catheter having an inner diameter within the range of from about 0.065 inches to about 0.075 inches and in one implementation catheter 120 has an inner diameter of about 0.071 inches. The second procedure catheter 124 may be an access catheter having an OD sized to permit advance through the first procedure catheter 120. The second procedure catheter may be steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having an inner diameter of at least about 0.075 or at least about 0.080 inches in diameter. The catheter 120 may be an aspiration catheter having an inner diameter within the range of from about 0.060 to about 0.075 inches. The catheter 124 may be a steerable catheter with a deflectable distal tip, having an inner diameter within the range of from about 0.025 to about 0.050 inches. The guidewire 27 may have an outer diameter within the range of from about 0.014 to about 0.020 inches. In one example, the catheter 31 may have an outer diameter of about 0.088 inches, the catheter 120 about 0.071 inches, the catheter 124 about 0.035 inches, and the guidewire 27 may have a diameter of about 0.018 inches.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 3G, 3H, 3I, 3J, 3K, 3L, 3M:
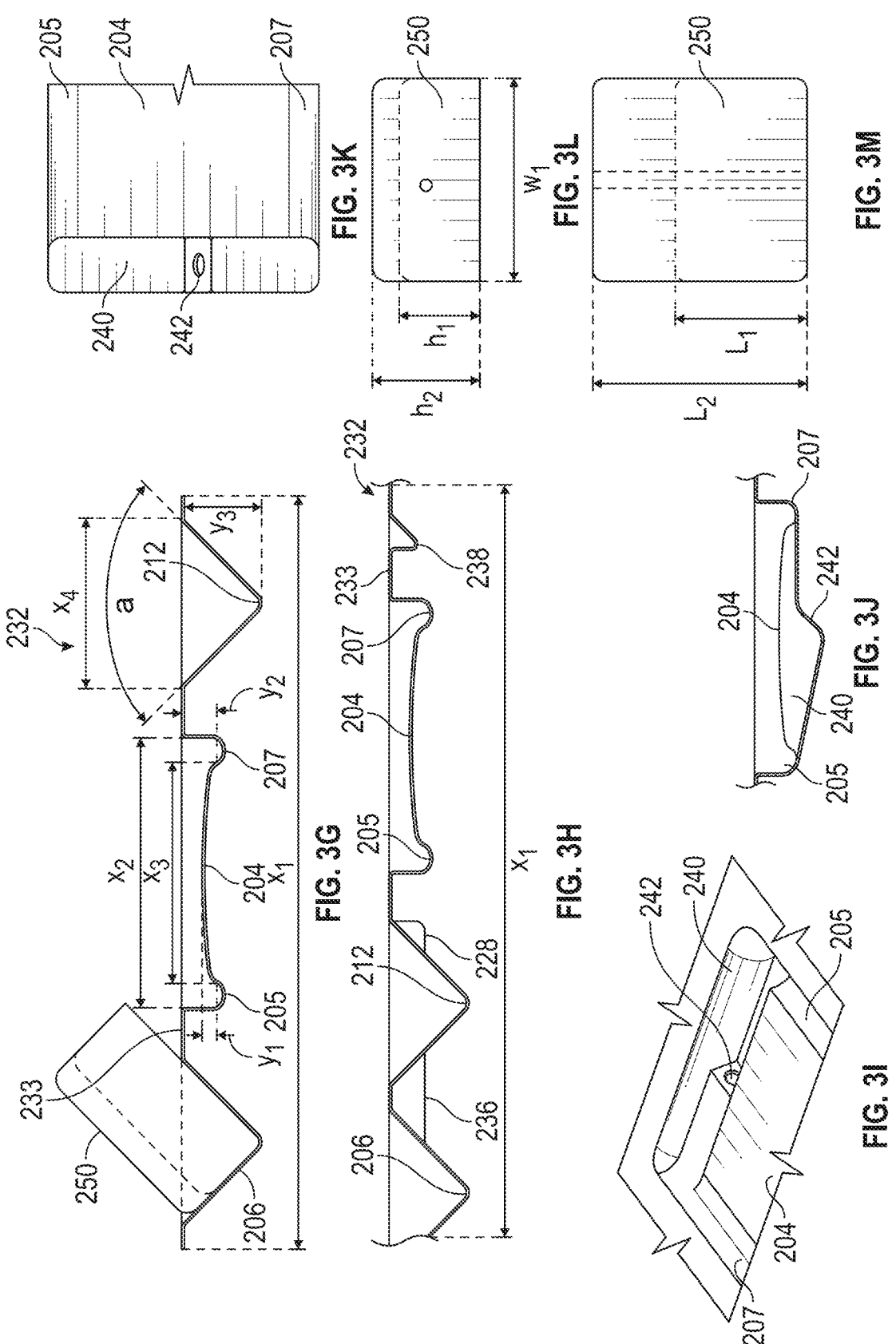
FIGS. 3G-3K show embodiments of an alternate sterile barrier having a convex drive surface.
FIGS. 3L and 3M depict an example of a hub that may be used with the sterile barriers of FIGS. 3G-3K.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

The trough 240 can include a drain hole 242. The trough 240 can be shaped, dimensioned, and/or otherwise configured so that fluid within the trough 240 empties to the drain hole 242. The drain hole 242 can include tubing, a barb fitting, and/or an on-off valve for removal of fluids from the trough 240. As shown in FIGS. 3I-3K, the trough 240 can be positioned at the proximal end of the sterile barrier 232. In alternate embodiments, the trough 240 may be positioned at a distal end of the sterile barrier 232. In some embodiments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dislodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alternate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as additional channels or wells may be provided, to hold additional medical devices or supplies that may be useful during the interventional procedure as well as to collect fluids and function as wash basins for catheters and related devices. In some embodiments, any of the channels or wells described herein may not be part of the sterile barrier, but may instead be part of the drive table positioned below the sterile barrier.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be 15 in, about 15 in, between 13 in and 17 in, between 11 in and 19 in, or any other suitable width. A height $y_1$ of the support surface 204 can be 0.125 in, about 0.125 in, between 0.1 and 0.15 in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and 0.75 in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and 5 in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle $\alpha$ of 90°, about 90°, between 80° and 100°, or any other suitable angle, and a radius of curvature of 0.125 in, about 0.125 in, between 0.1 and 0.15 in, or any other suitable radius of curvature. In certain embodiments, an arc angle $\alpha$ of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height $h_1$ of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configuration shown, for example, in FIGS. 3A-3F. For example, the support surface 104 can be positioned at about 90 degrees (or any other suitable angle) from a horizontal plane (e.g., rotated 90 degrees about a long axis of the support surface 104 relative to the embodiment shown in of FIGS. 3A-3F). A vertical configuration may provide for easier interaction with the drive system 18 by a physician. A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figures 4, 5A, 5B:
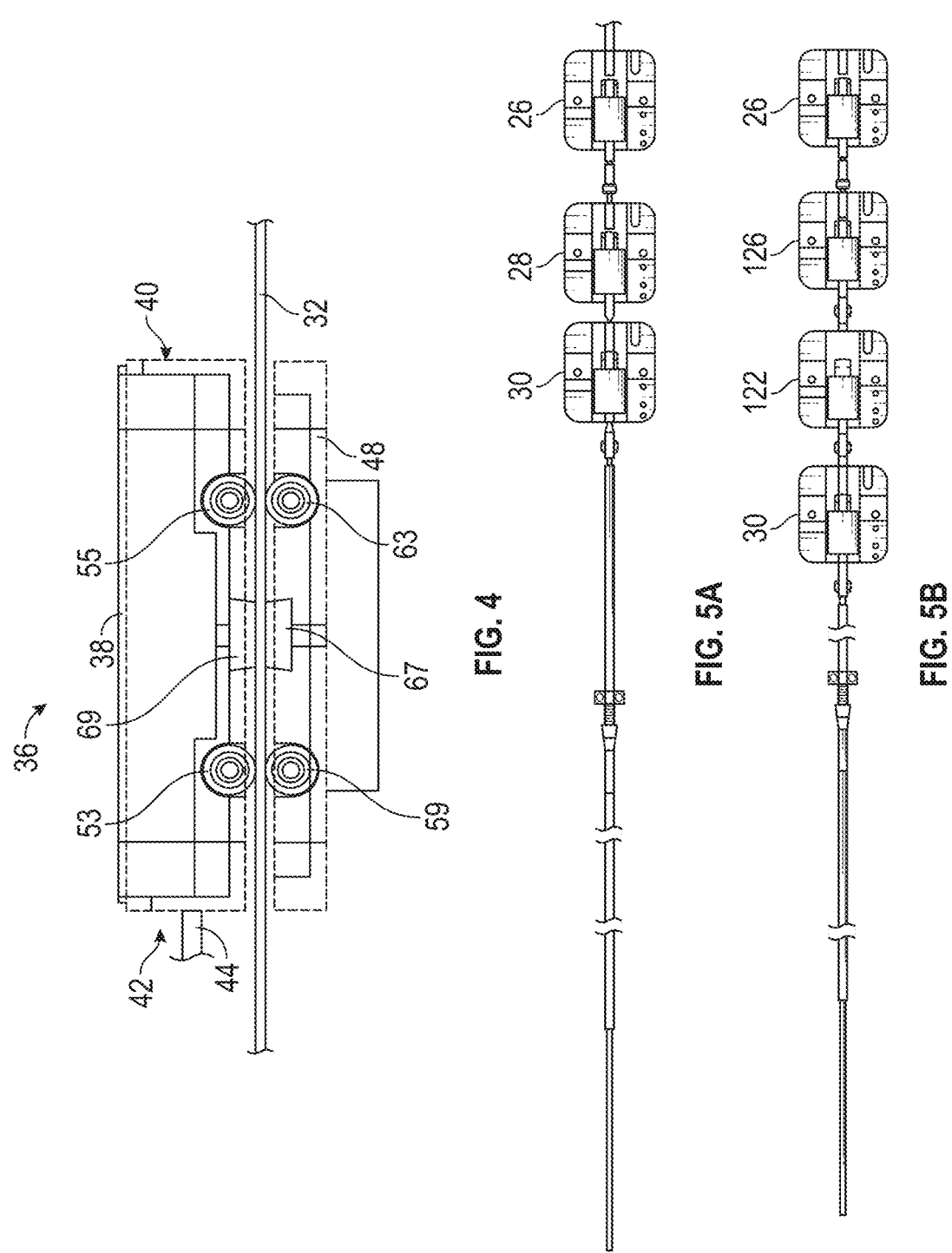
FIG. 4 is a schematic elevational cross section through a hub adapter having a drive magnet separated from an interventional device hub and driven magnet by a sterile barrier.
FIGS. 5A and 5B schematically illustrate a three interventional device and a four interventional device assembly.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field.

Movement of the hub adapter is driven by a drive system carried by the support table and described in additional detail below.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some implementations, the space is within the range of from about 0.03 centimeters (about 0.010 inches) and about 0.041 centimeters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 centimeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
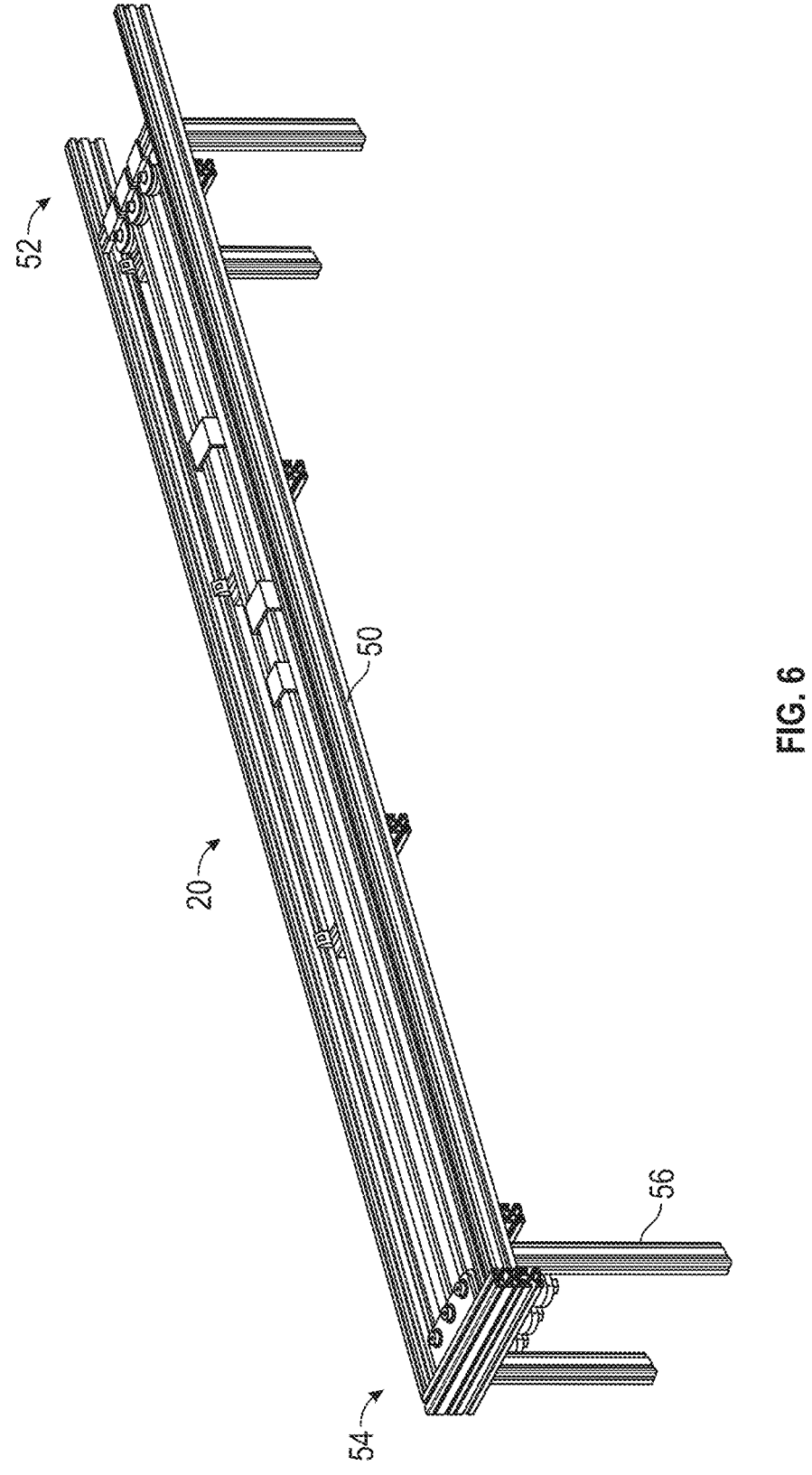
FIG. 6 is a perspective view of a support table.

Referring to FIG. 6, there is schematically illustrated one example of a low-profile linear drive support table 20. Support table 20 includes an elongated frame 51 extending between a proximal end 52 and a distal end 54. At least one support table support 56 is provided to stabilize the support table 20 with respect to the patient (not illustrated). Support 56 may include one or more legs or preferably an articulating arm configured to allow movement and positioning of the frame 51 over or adjacent to the patient.

Figure 7:
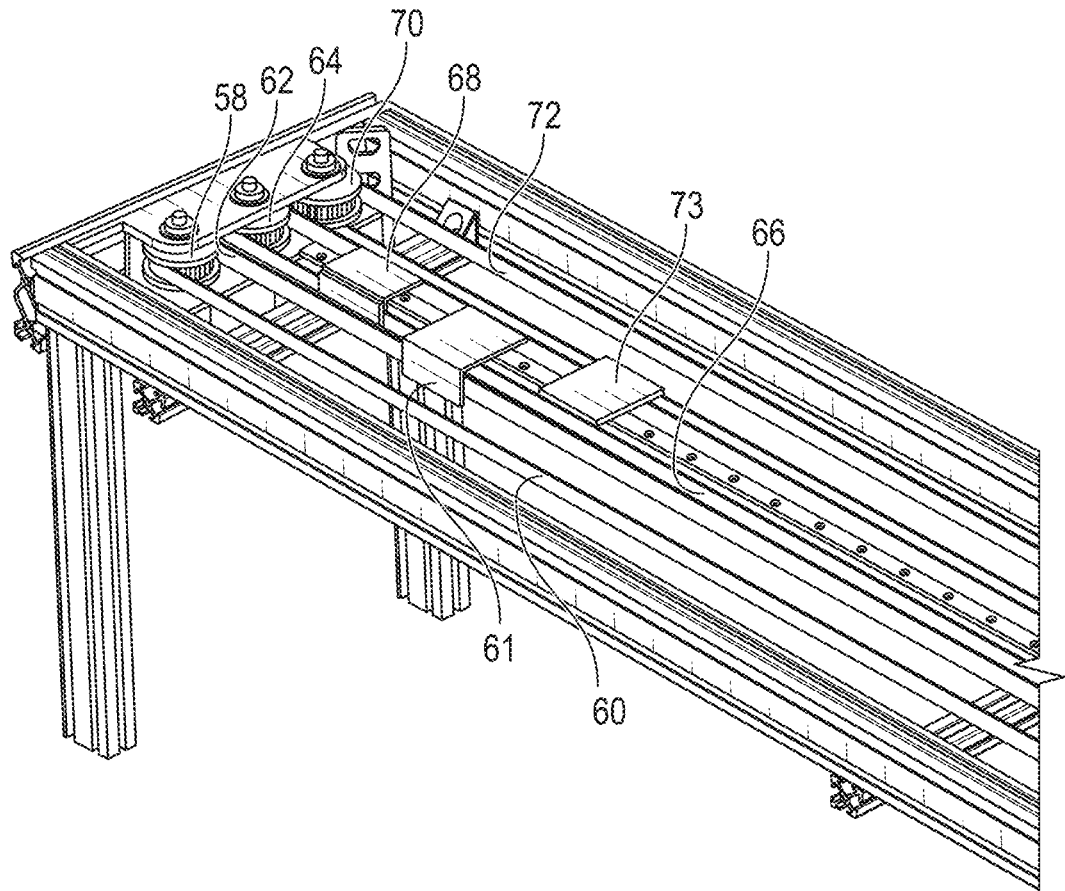
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
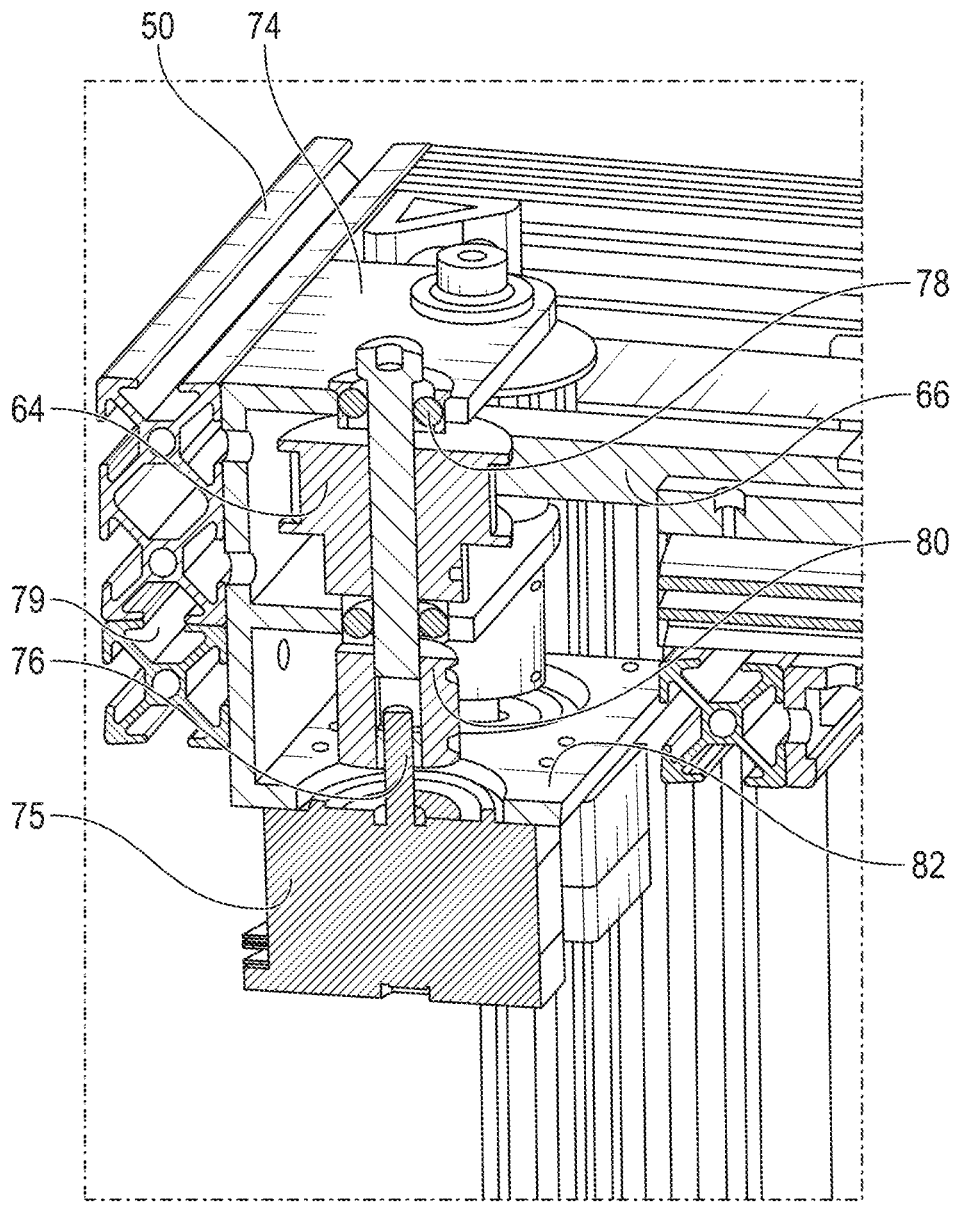
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 maybe similarly constructed and are not further detailed herein. In some embodiments, the drive systems described herein may be a rack and pinion drive table system that is foldable. In such embodiments, motors 75 may be attached to and move with the carriages.

Figure 9:
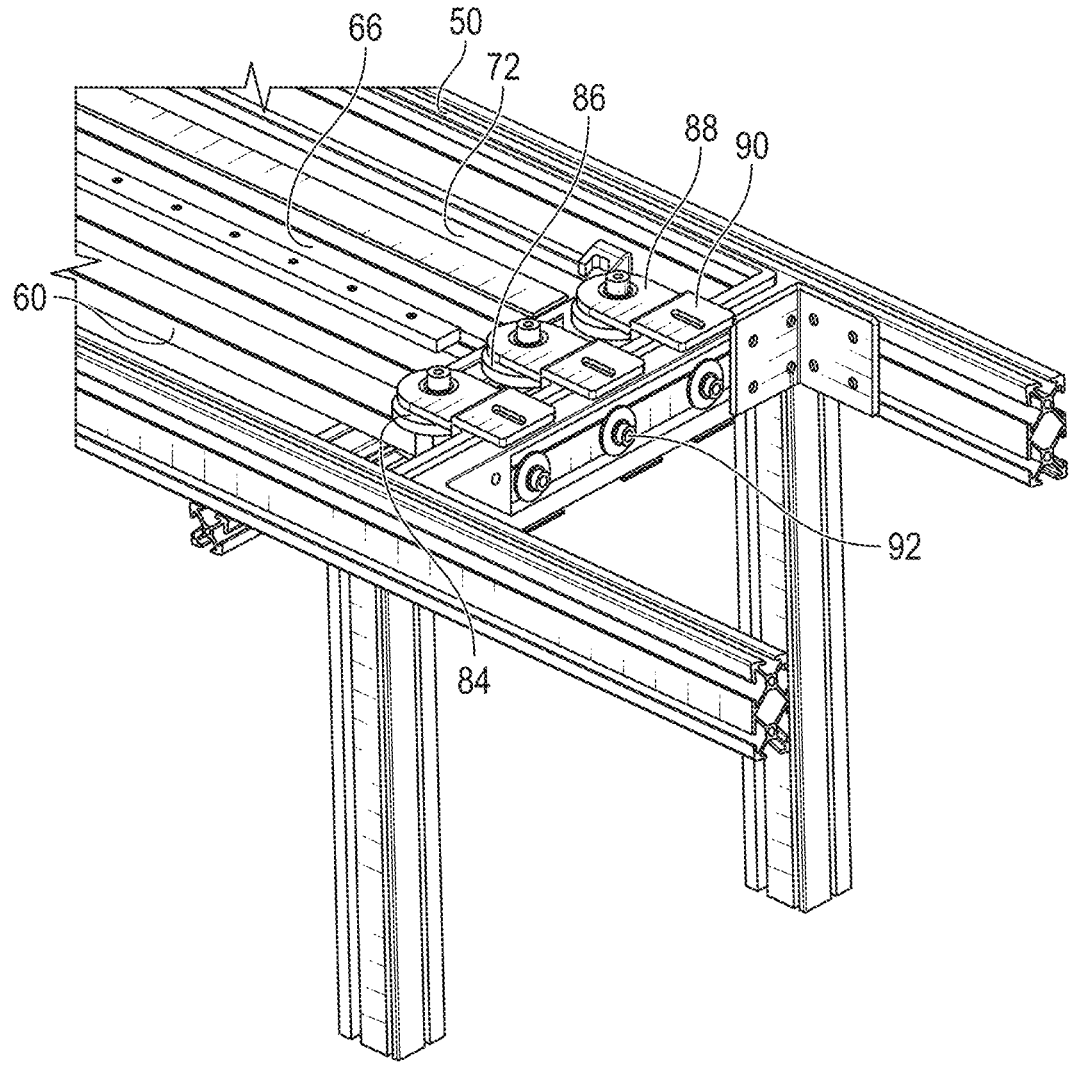
FIG. 9 is a close-up view of a pulley end of the support table.
Figure 10:
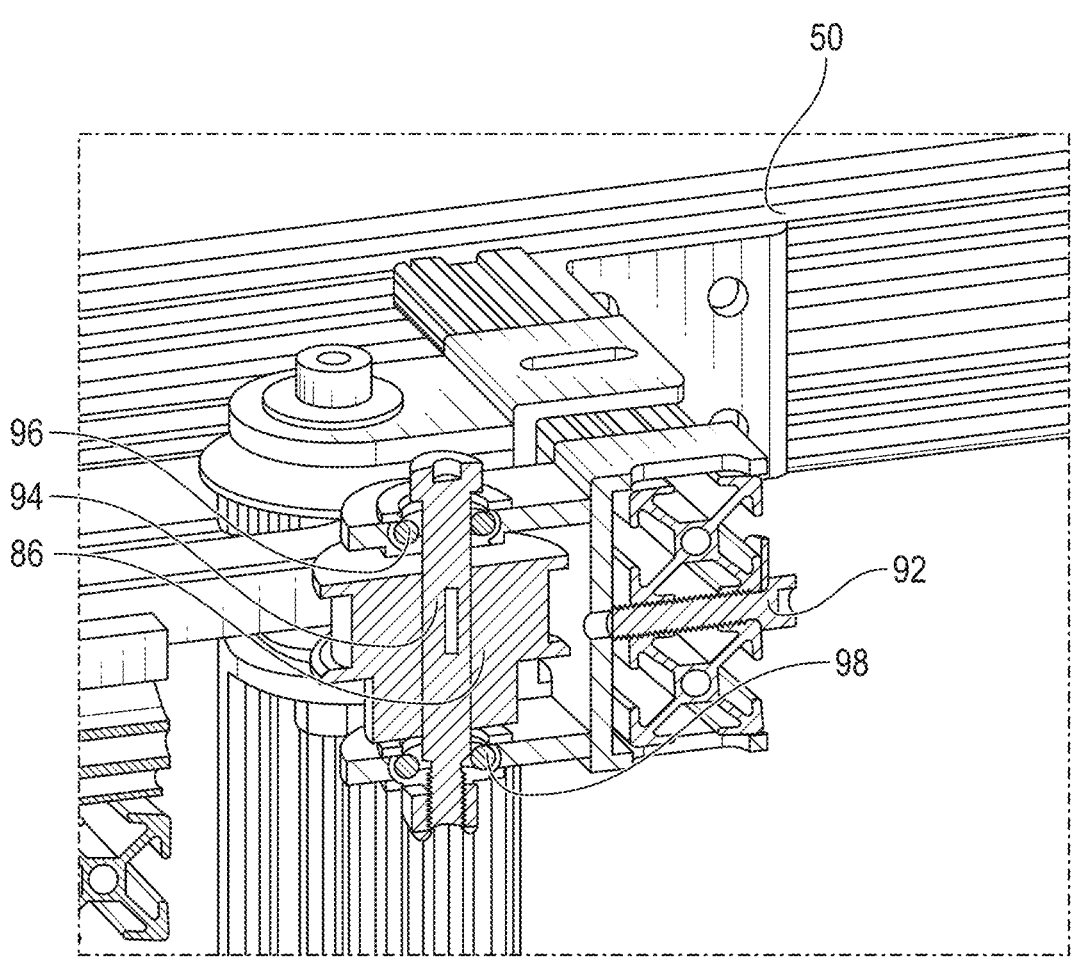
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 11:
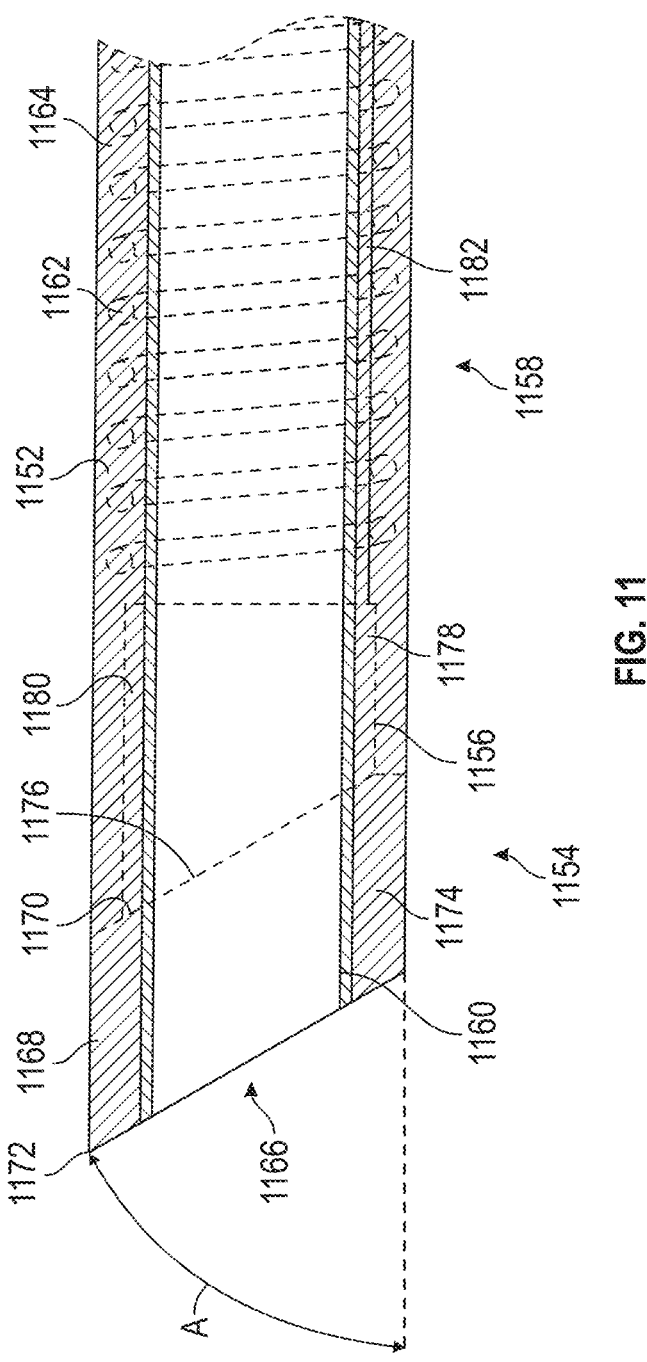
FIG. 11 is a side elevational cross-section through a distal portion of a catheter such as any of those shown in FIGS. 5A and 5B.

Any of the catheters illustrated, for example, in FIG. 5A, 5B or 11 generally include an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 includes a tubular body 1152 which includes an advance segment 1154, a marker band 1156 and a proximal segment 1158. An inner tubular liner 1160 may extend throughout the length of the distal catheter tip 1150, and may include dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may include any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may include a distal extension of the outer tubular jacket 1164 and optionally the inner liner 1160, without other internal supporting structures distally of the marker band 1156. Outer jacket 1164 may include extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further include an axial tension element or support such as a ribbon or one or more filaments or fibers for increasing the tension resistance and/or influencing the bending characteristics in the distal zone. The tension support may include one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may include materials such as Vectran®, Kevlar®, Polyester®, Spectra®, Dyneema®, Meta-Para-Aramide®, or any combinations thereof. At least one of the one or more tension element 1182 may include a single fiber or a multi-fiber bundle, and the fiber or bundle may have a round or rectangular (e.g., ribbon) cross section. The terms fiber or filament do not convey composition, and they may include any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figures 12A, 12B:
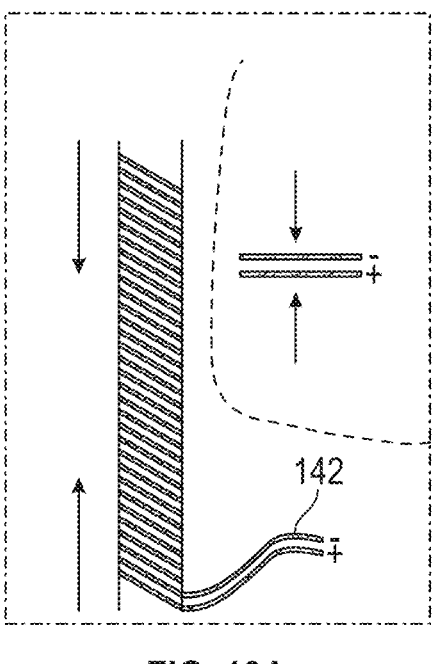
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
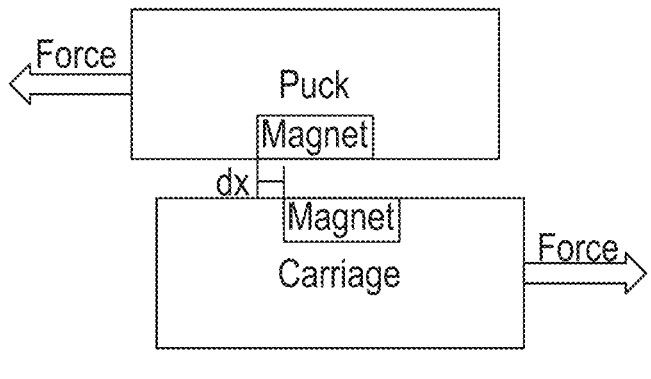
FIGS. 13A and 13B schematically illustrate a sensor for measuring elastic forces at the magnetic coupling between the hub and corresponding carriage.
Figure 13B:

It may also be desirable to measure clastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the hub and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs and carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the hubs through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
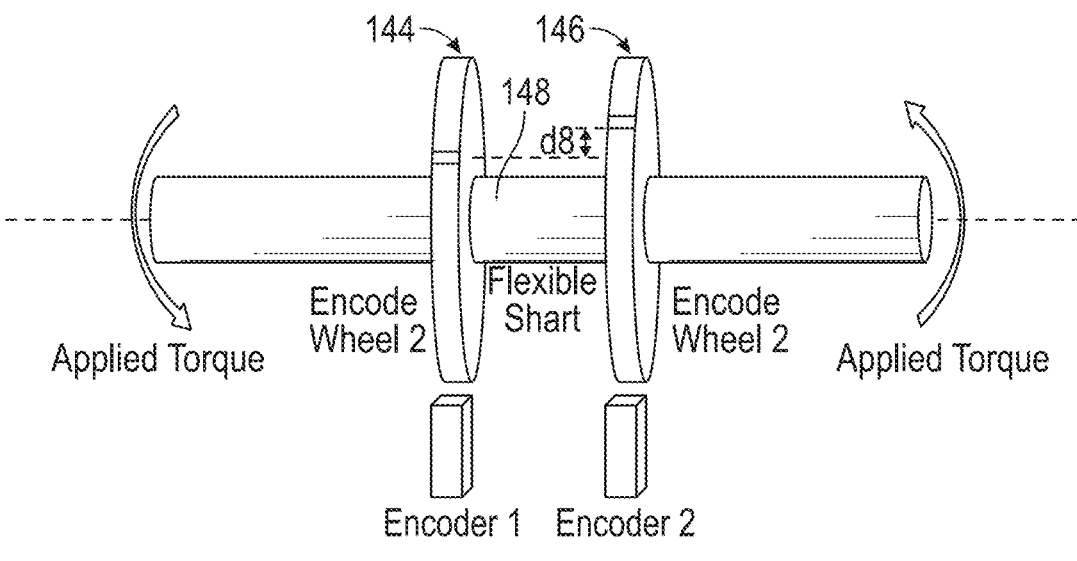
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders (dθ) tells us the torque. T=k*dθ, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
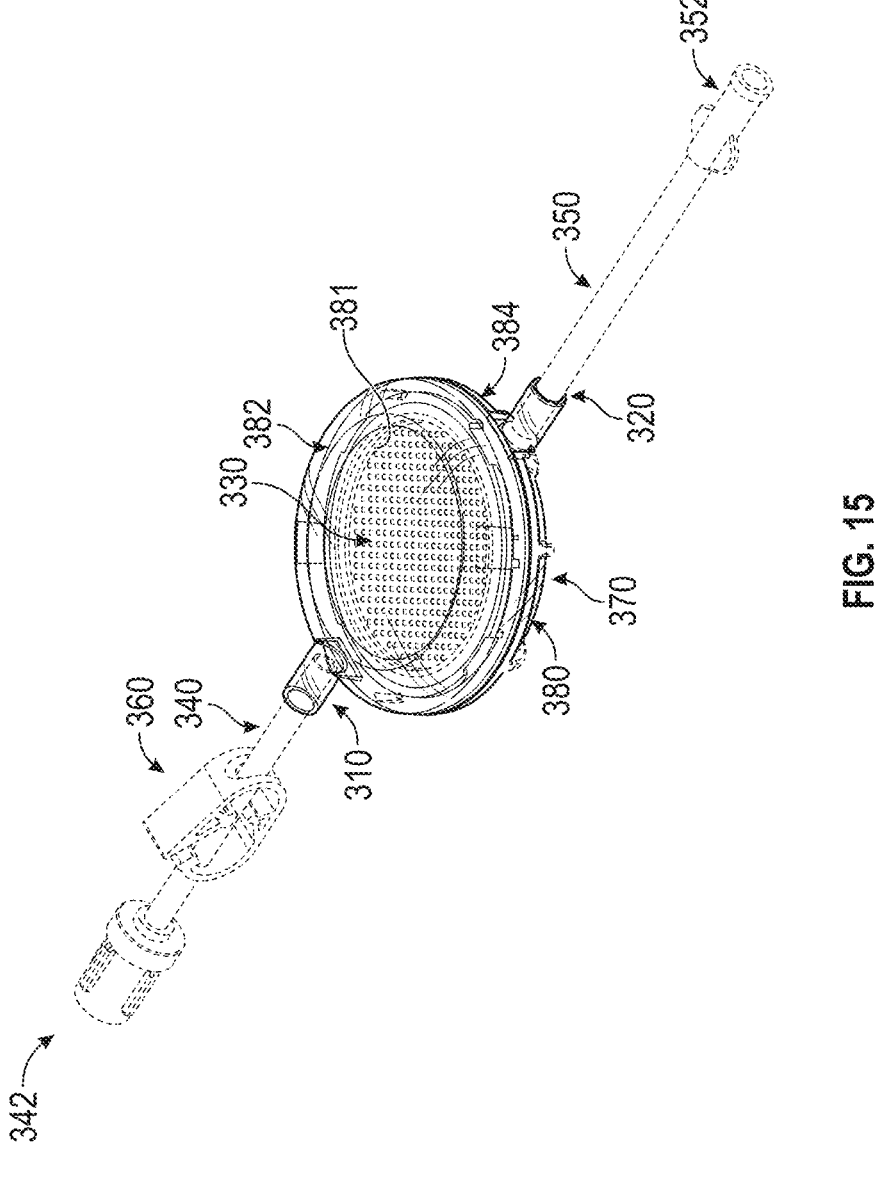
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp. The clamp can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

Figure 16A:
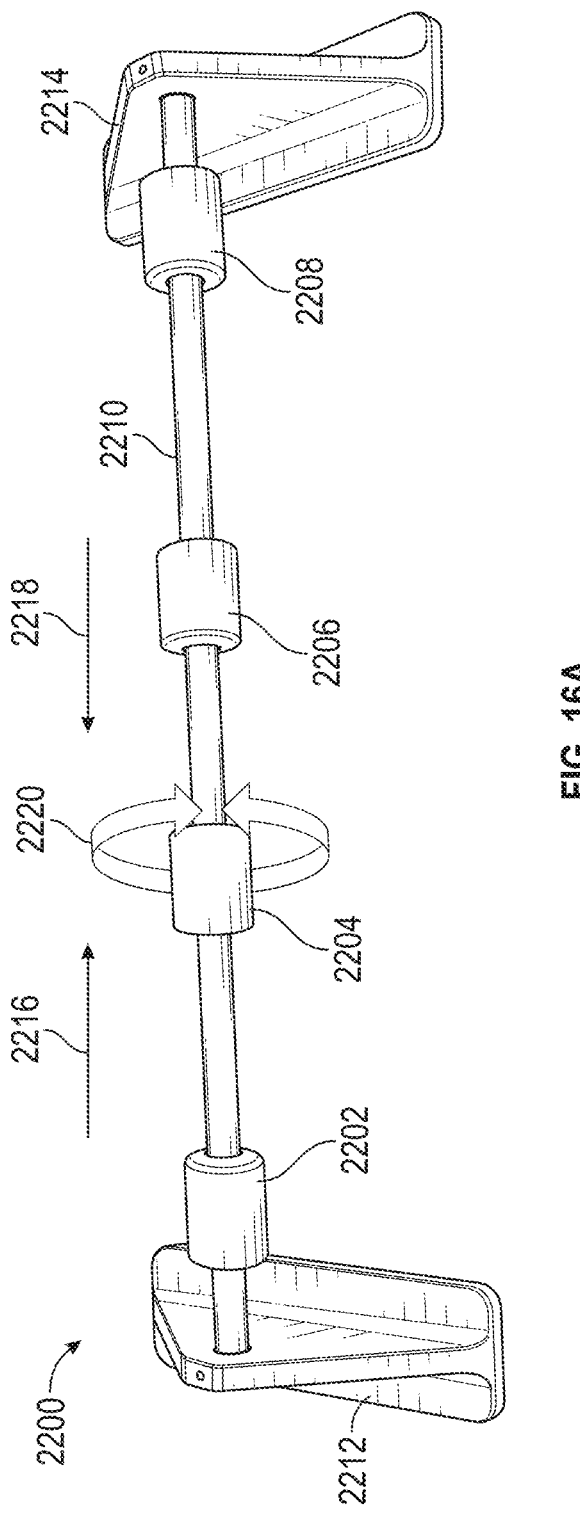
FIGS. 16A-16C illustrate an example control mechanism for manipulating interventional devices driven by respective hubs.
Figure 16B:
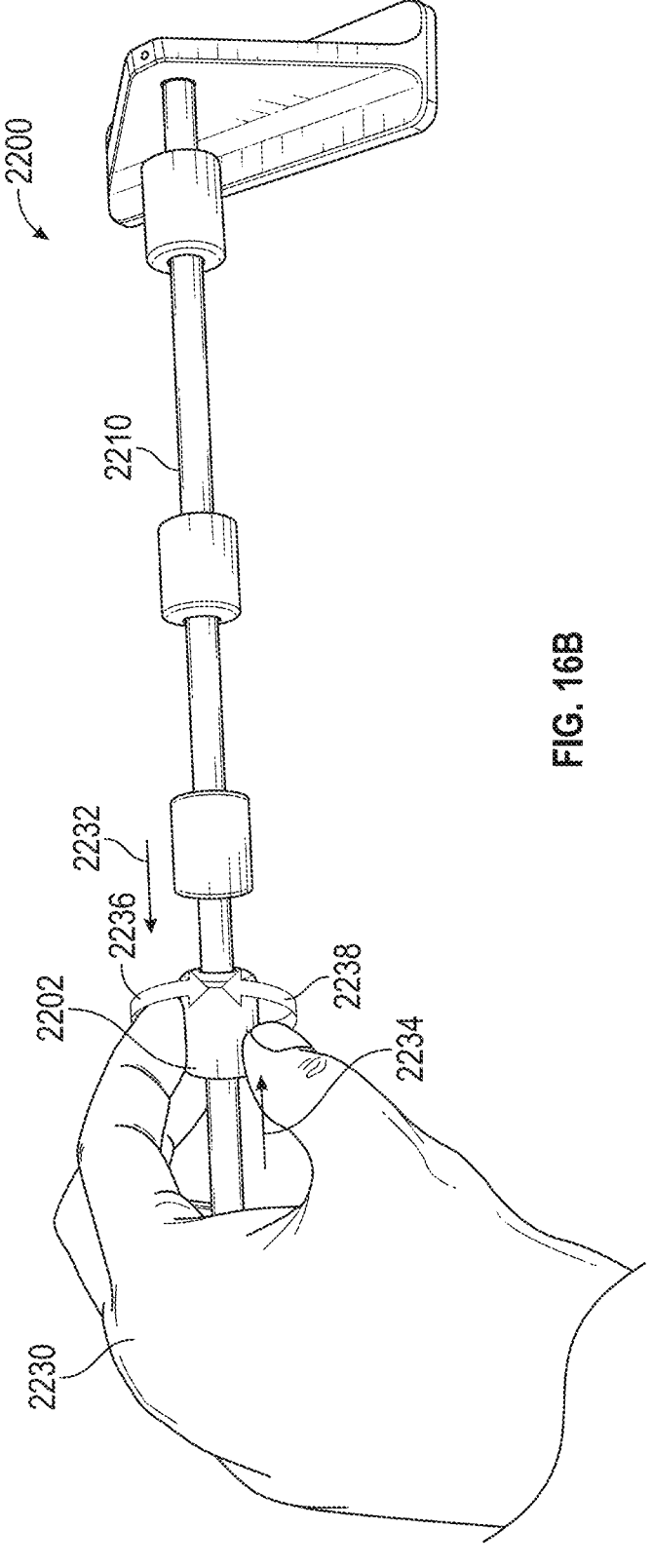
Figure 16C:
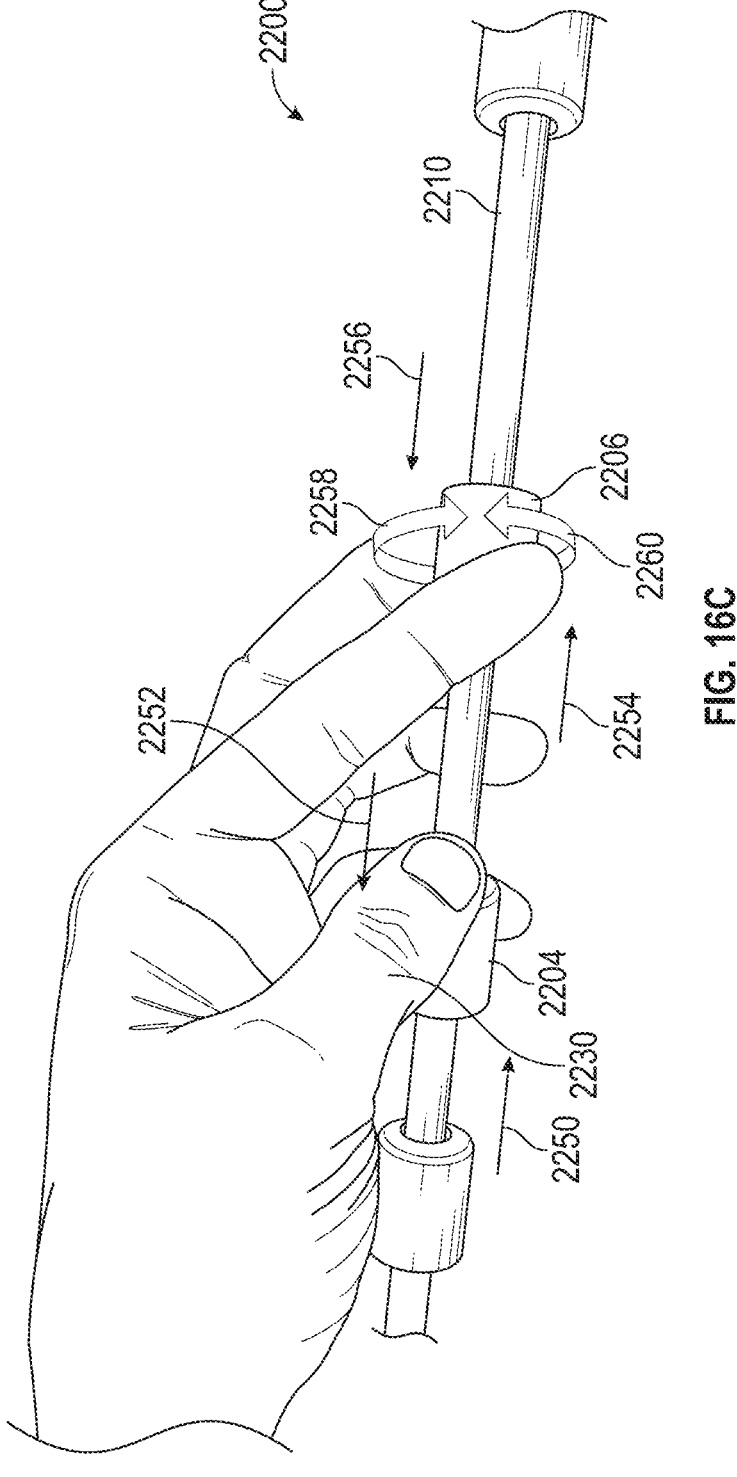

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 include a first control 2202, a second control 2204, a third control 2206, and a fourth control 2208. More or fewer controls may be provided, depending upon the intended interventional devices configuration. Each control 2202-2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device.

Axial movement of a control may be configured to move the coupled hub on a 1:1 basis, or on a non 1:1 scaled basis. For example, if the user 2230 advances the control 2022 about 5 millimeters distally along the shaft 2210, then the corresponding hub may responsively move 5 millimeters in the distal direction.

If the user 2230 rotates the control 2022 about its rotational axis by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using controls 2202-2208. For example, controls 2202-2208 may be configured to drive a shape change and/or stiffness change of a corresponding interventional device. Controls 2202-2208 may be toggled between different operating modes. For example, controls 2202-2208 may be toggled between movement driven by acceleration and velocity to movement that reflects actual linear displacement or rotation.

In some implementations, the control mechanism 2200 may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism 2200 may include haptic components to provide haptic feedback to a user operating the controls. For example, if the control 2202 is triggering movement of a catheter and the catheter detects a large force at the tip, the control 2202 may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
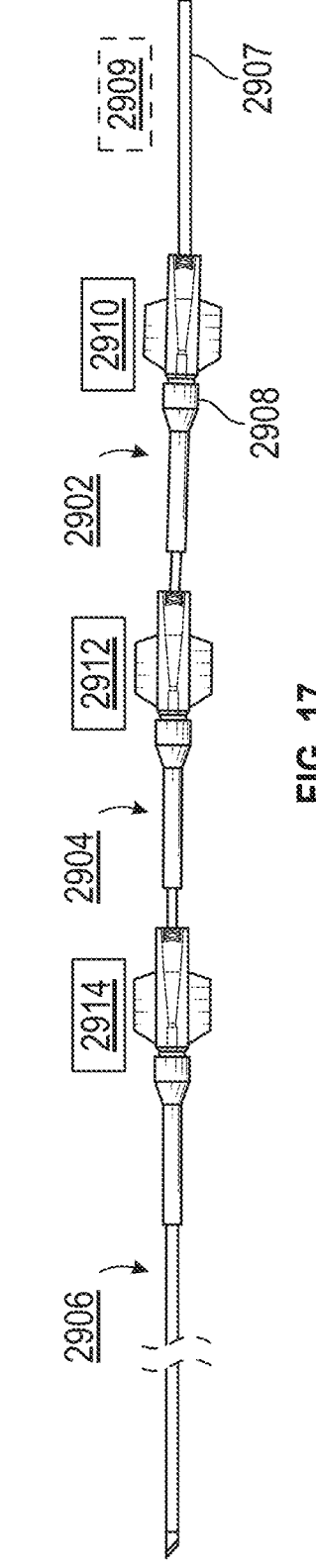
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more catheters of assembly 2900.

In operation, the multi-catheter assembly 2900 may be used without having to exchange hub components. For example, in the two stage procedure disclosed previously, a first stage for achieving supra-aortic access, includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. Additional details regarding hemostasis valves are included in U.S. patent application Ser. No. 17/879,614, entitled Multi Catheter System With Integrated Fluidics Management, filed Aug. 2, 2022, which is hereby expressly incorporated by reference in its entirety herein Once access above the aortic arch has been achieved, the insert or access catheter 2902 (associated with insert catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the catheter 2906 may function as a guide catheter. The catheter 2904 may function as a procedure (e.g., aspiration) catheter. In some embodiments, the catheter 2906 may function to perform aspiration in addition to functioning as a guide catheter, either instead of or in addition to the catheter 2904. The access catheter 2902 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having a diameter of at least about 0.075 or at least about 0.080 inches in diameter. The procedure catheter 2904 may be an aspiration catheter having a diameter within the range of from about 0.060 to about 0.075 inches. The access catheter 2902 may be a steerable catheter with a deflectable distal tip, having a diameter within the range of from about 0.025 to about 0.050 inches. The guidewire 2907 may have a diameter within the range of from about 0.014 to about 0.020 inches. In one example, the guide catheter 2906 may have a diameter of about 0.088 inches, the procedure catheter 2904 about 0.071 inches, the access catheter 2902 about 0.035 inches, and the guidewire 2907 may have a diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Figures 18A, 18B, 18C:
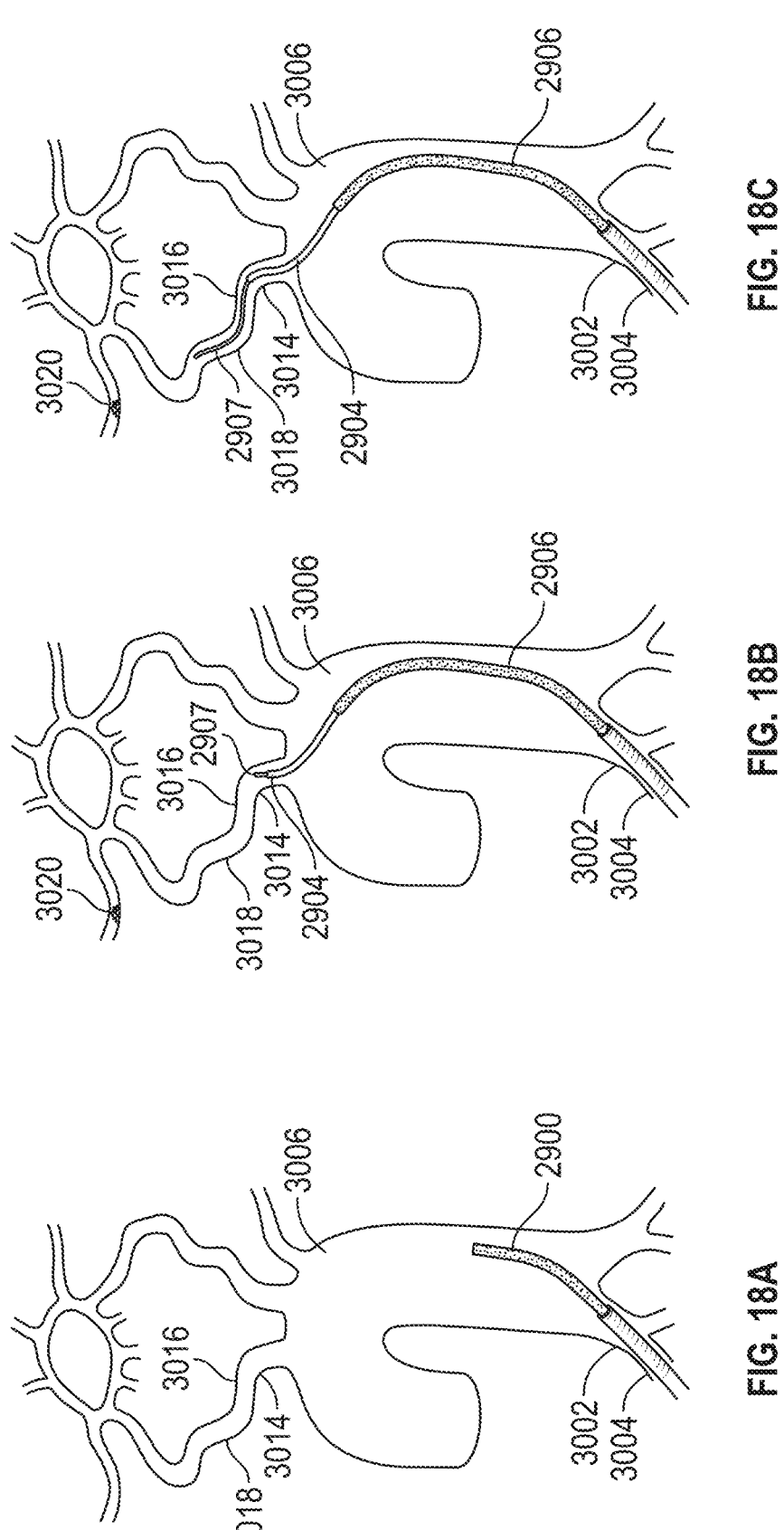
FIGS. 18A-18E depict an example sequence of steps of introducing a catheter assembly configured to achieve supra-aortic access and neurovascular site access.

Referring to FIG. 18A, the three catheter interventional device assembly 2900 is shown driven through an introducer sheath 3002, up through the iliac artery 3004 and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced up to the petrous segment 3018 of the internal carotid artery 3016.

Figure 18E:
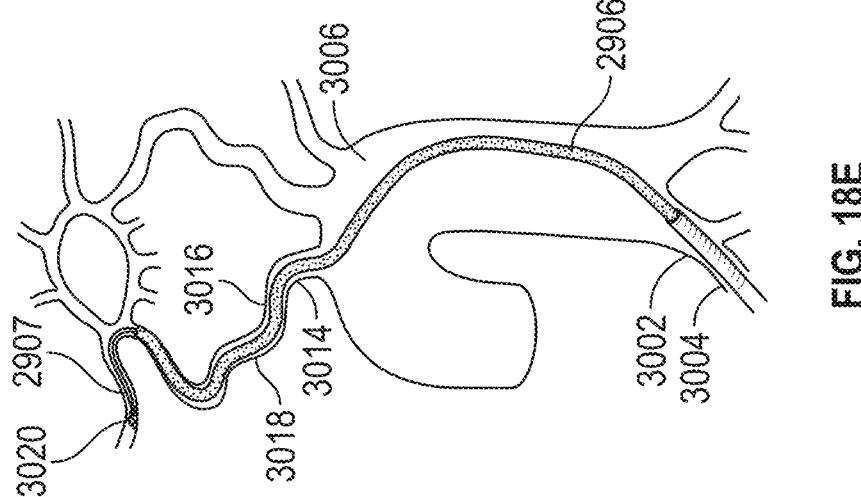
Figure 18D:
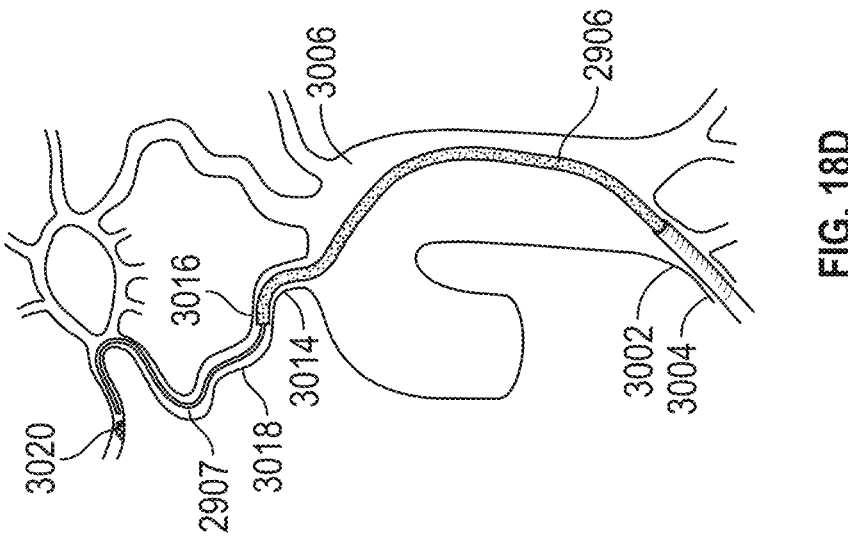

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the M1 segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub 2909 on the guidewire 2907 to a first drive magnet, magnetically coupling a second hub 2910 on the access catheter 2902 to a second drive magnet, magnetically coupling a third hub 2912 on the procedure catheter 2904 to a third drive magnet, and magnetically coupling a fourth hub 2914 on the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

An example robotic control system may include at least a guidewire hub (e.g., guidewire hub 2909) configured to adjust each of an axial position and a rotational position of a guidewire 2907. The robotic control system may also include an access catheter hub 2910 configured to adjust axial and rotational movement of an access catheter 2902. The robotic control system may also include a guide catheter hub 2914 configured to control axial movement of a guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The access catheter hub 2910 is configured to couple to an access catheter hub adapter by magnetically coupling the access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail with respect to FIG. 4 above.

In some embodiments, the robotic control system includes a second driven magnet on the access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the access catheter hub 2910, the procedure catheter hub 2912, and/or the guide catheter hub 2914) with one or more drive mechanisms.

Figure 23:
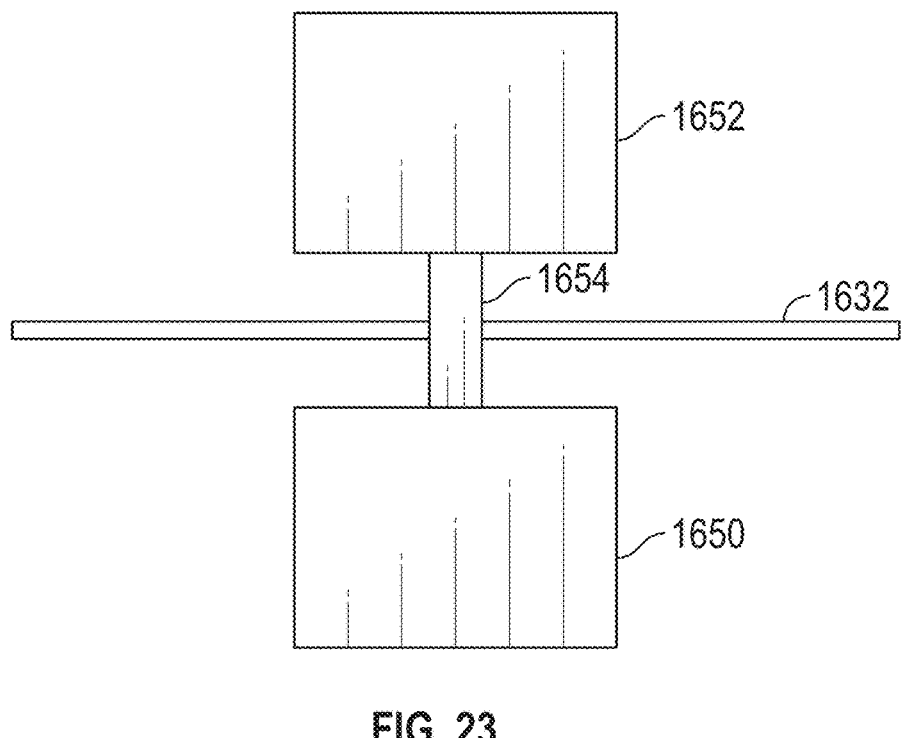
FIG. 23 schematically illustrates an embodiment of a mechanical coupling between a drive mechanism and a driven mechanism.

FIG. 23 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the access catheter hub 2910, the procedure catheter hub 2912, or the guide catheter hub 2914). In some instances, the mechanical coupling mechanism 1654 may include a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may include a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the coaptive edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The mechanical coupling mechanism 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn turn the sterile pulley in the hub via the sterile splined shaft.

It will be understood by one having skill in the art that any embodiment as described herein may be modified to incorporate a mechanical coupling mechanism, for example, as shown in FIG. 23.

Figure 19A:
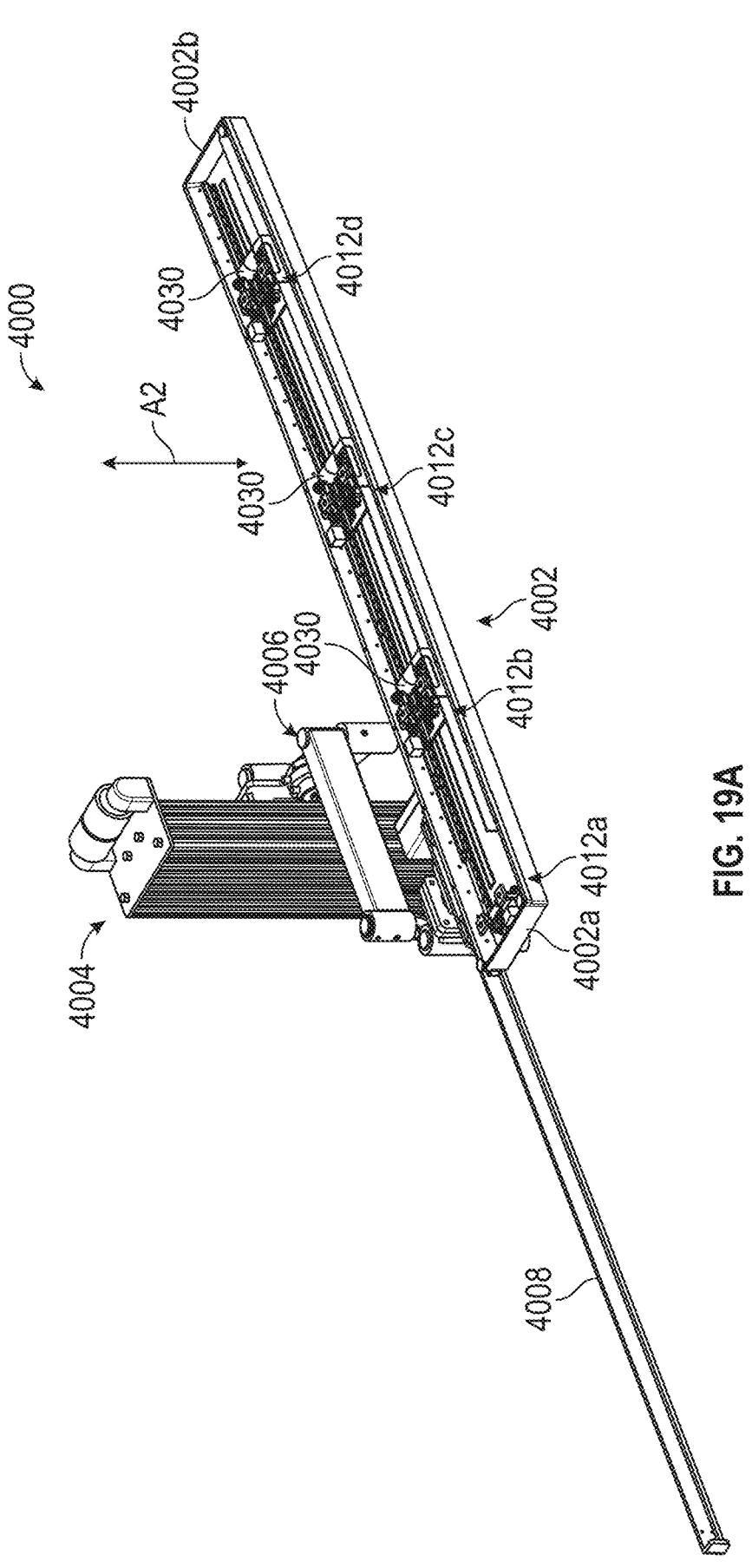
FIGS. 19A-19J show another embodiment of a robotic control system.

Telescoping Hub Drive:

Any embodiments of the robotic control system disclosed herein can have a telescopic or telescoping drive table coupled. An example embodiment of a robotic control system 4000 having a telescoping drive table 4002 coupled with a base structure 4004 is shown in FIG. 19A. In some embodiments, the drive table 4002 can have any of the components, features, and/or details of any other embodiments of the drive tables disclosed herein, including without limitation one, two, three, four, or more than four hub adapters 4012 (e.g., hub adapters 4012a-d in FIG. 19A) that can be used to move one, two, three, four, or more than four hubs (not shown in FIG. 19A) in an axial direction and/or vertical direction, as will be described. As described, the hubs can each be coupled to or configured to receive an interventional device. More or fewer hub adapters and interventional device hubs can be supported by the drive table 4002, depending upon the desired clinical procedure.

Figure 19B:
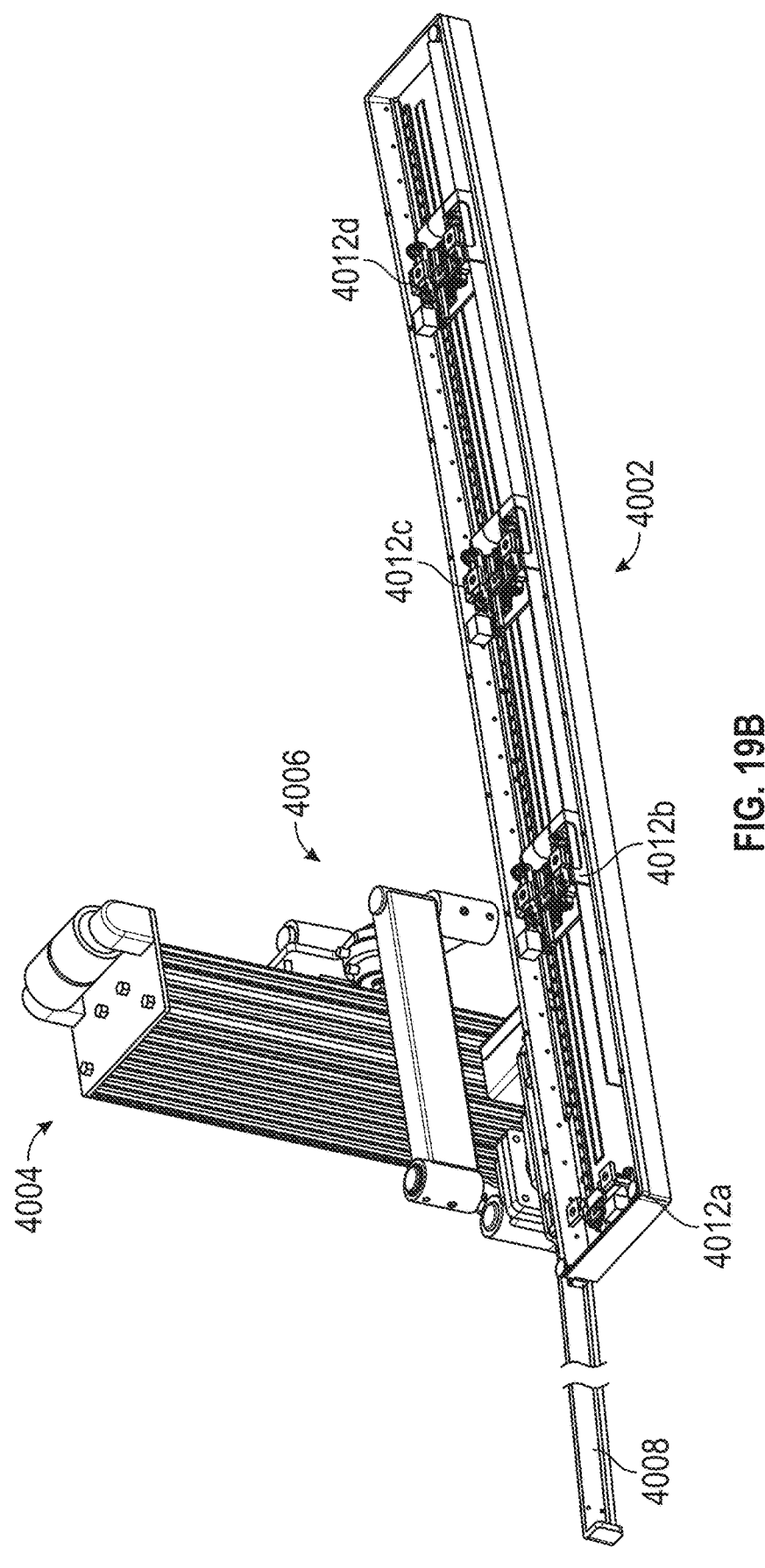
Figure 19C:
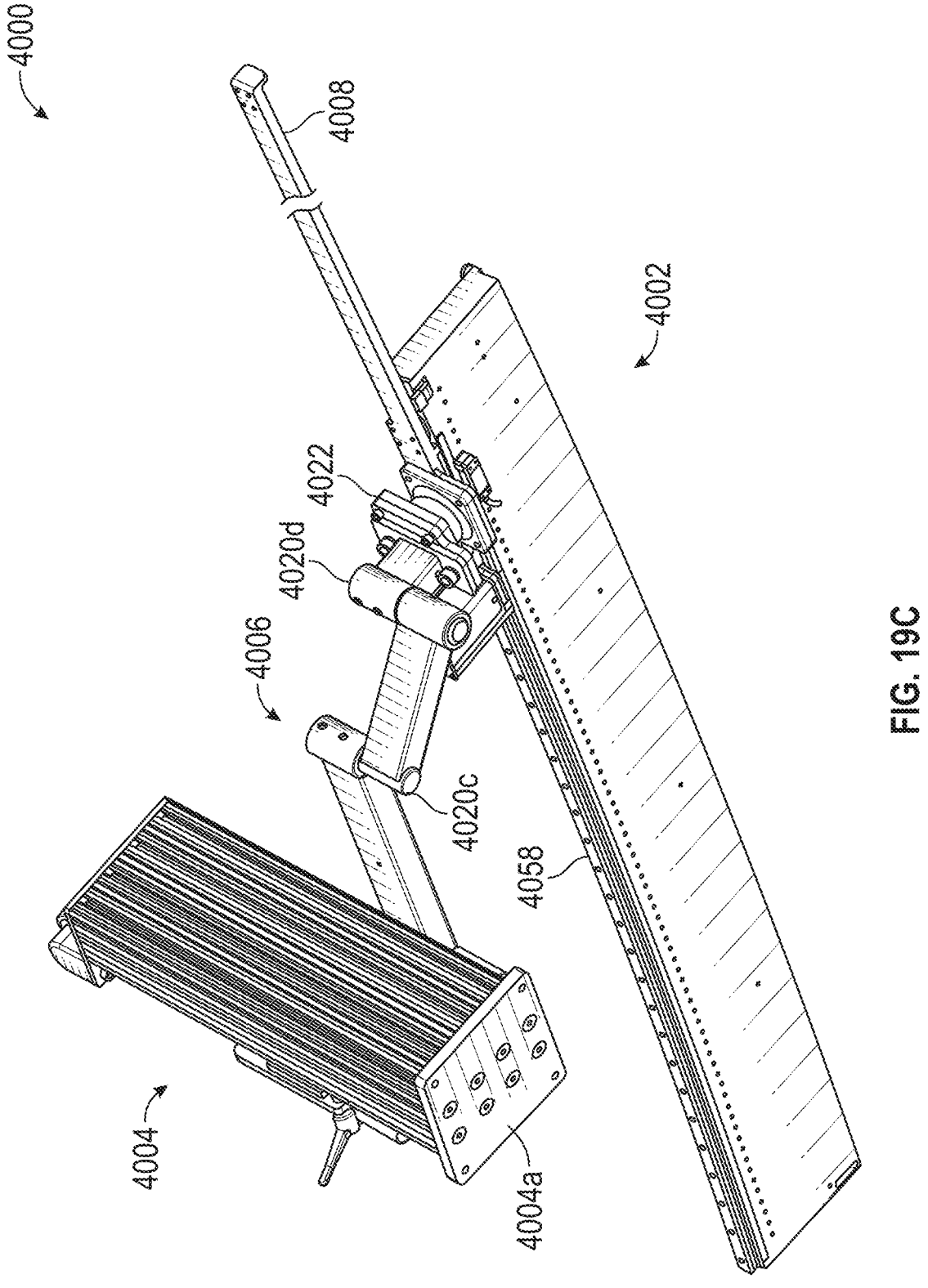
Figure 19D:
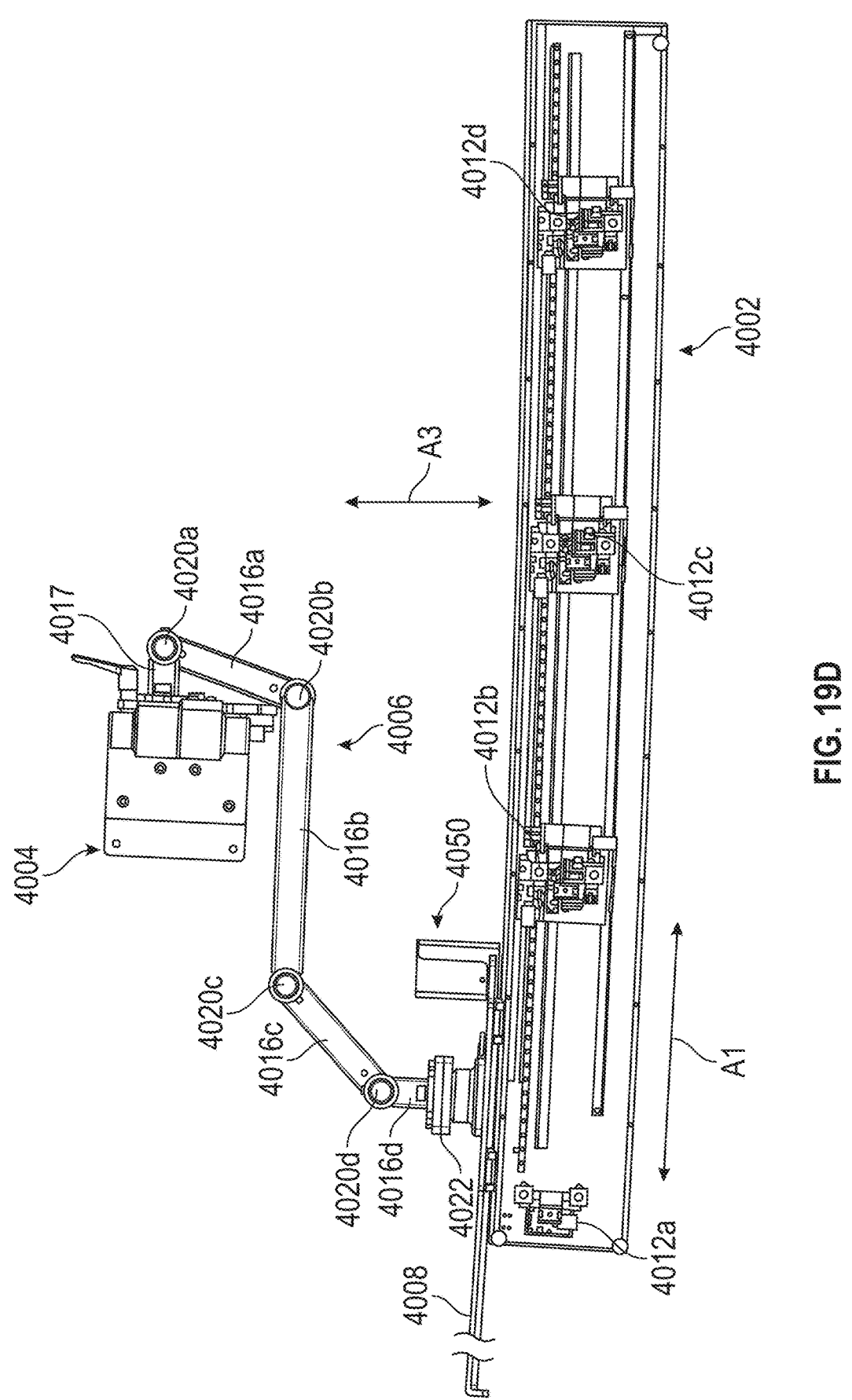
Figure 19E:
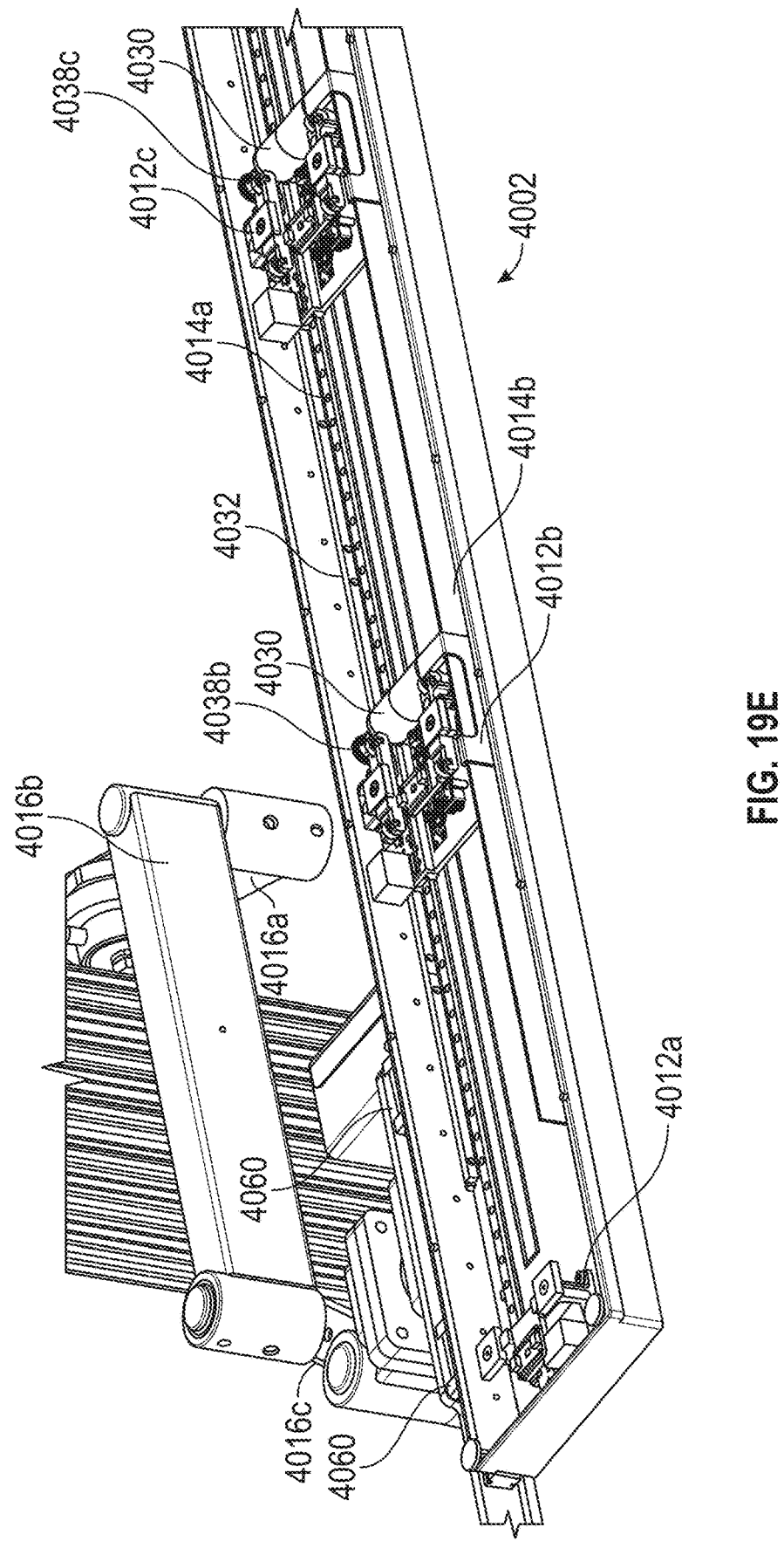
Figure 19F:
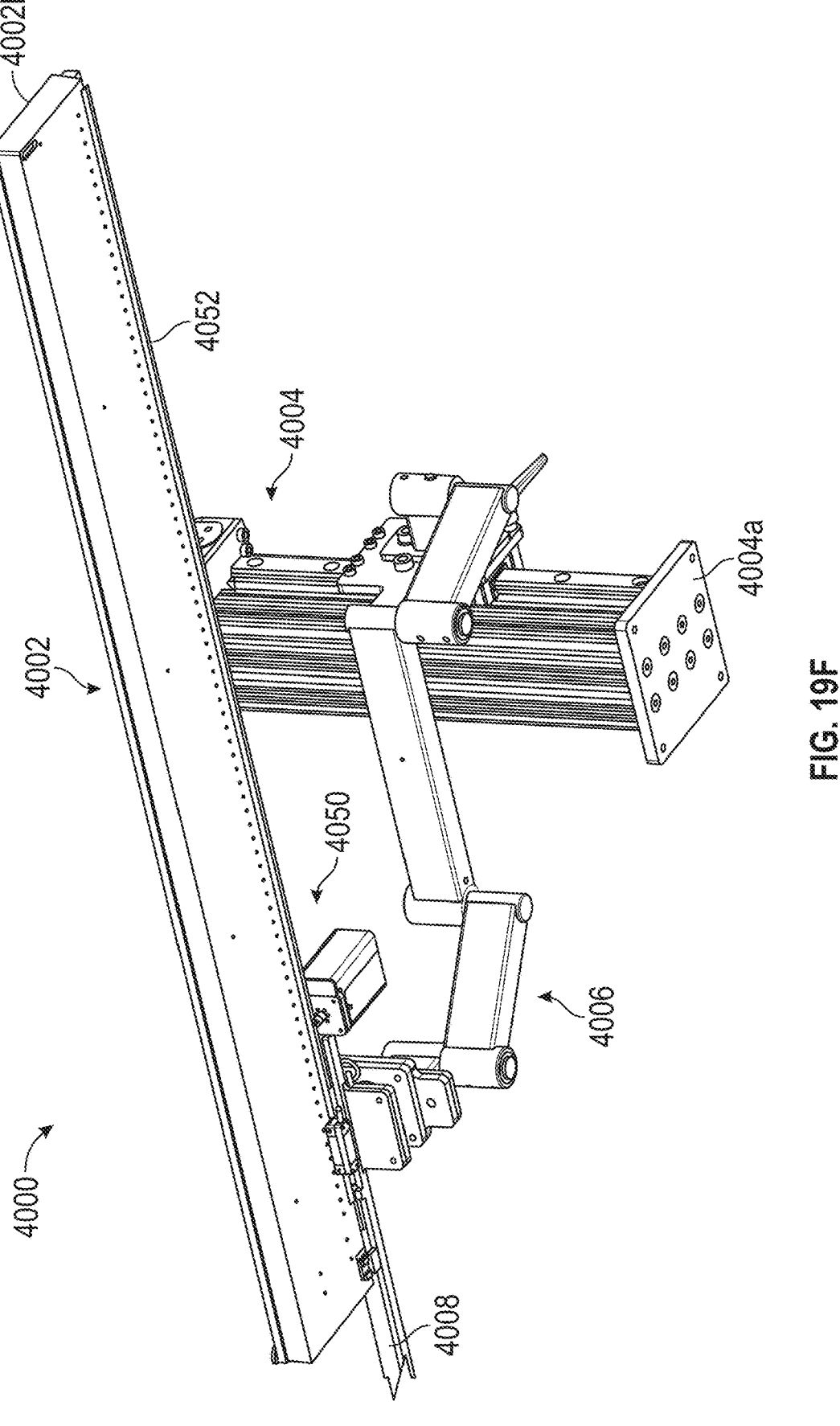
Figure 19G:
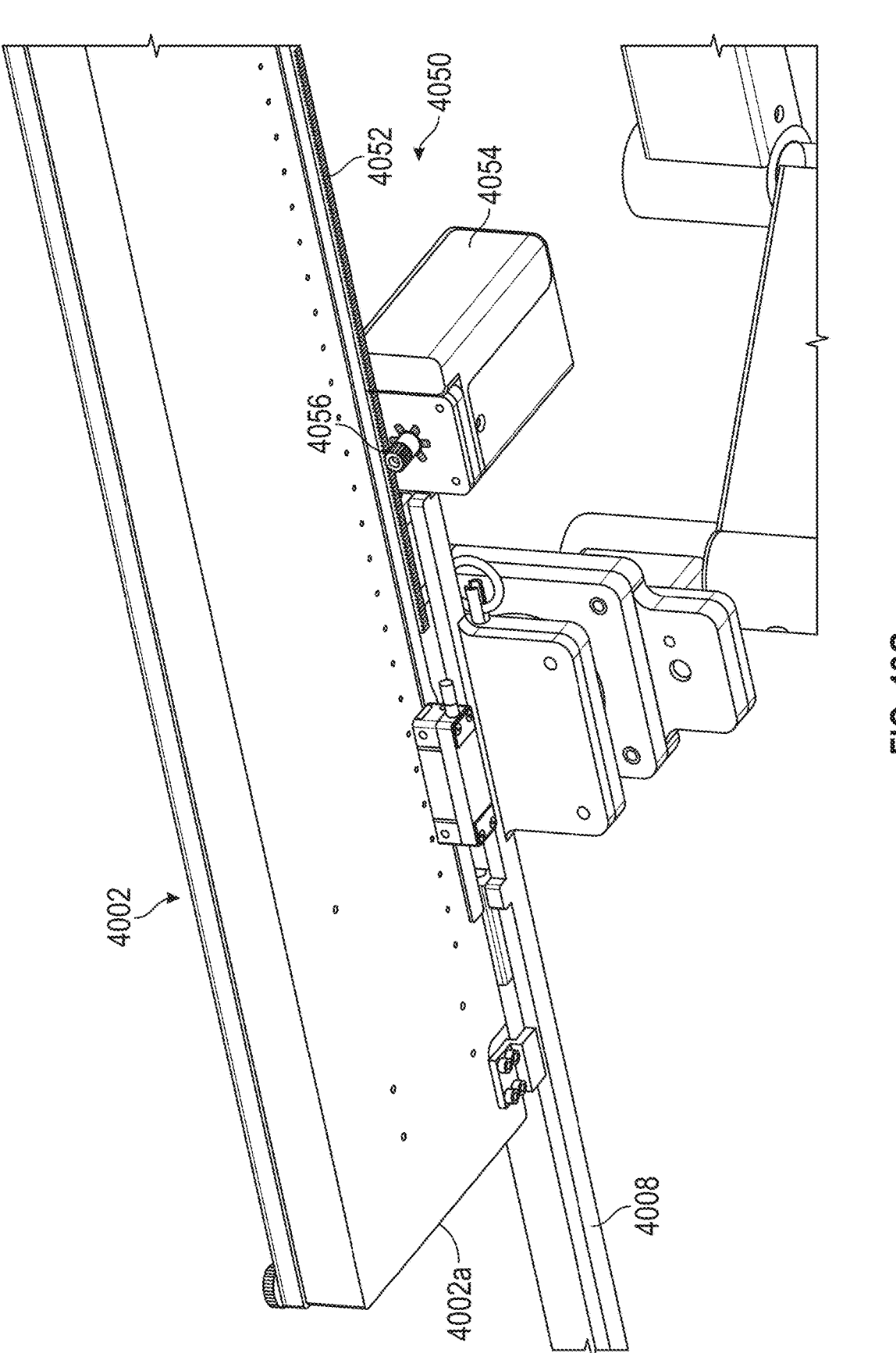
Figure 19H:
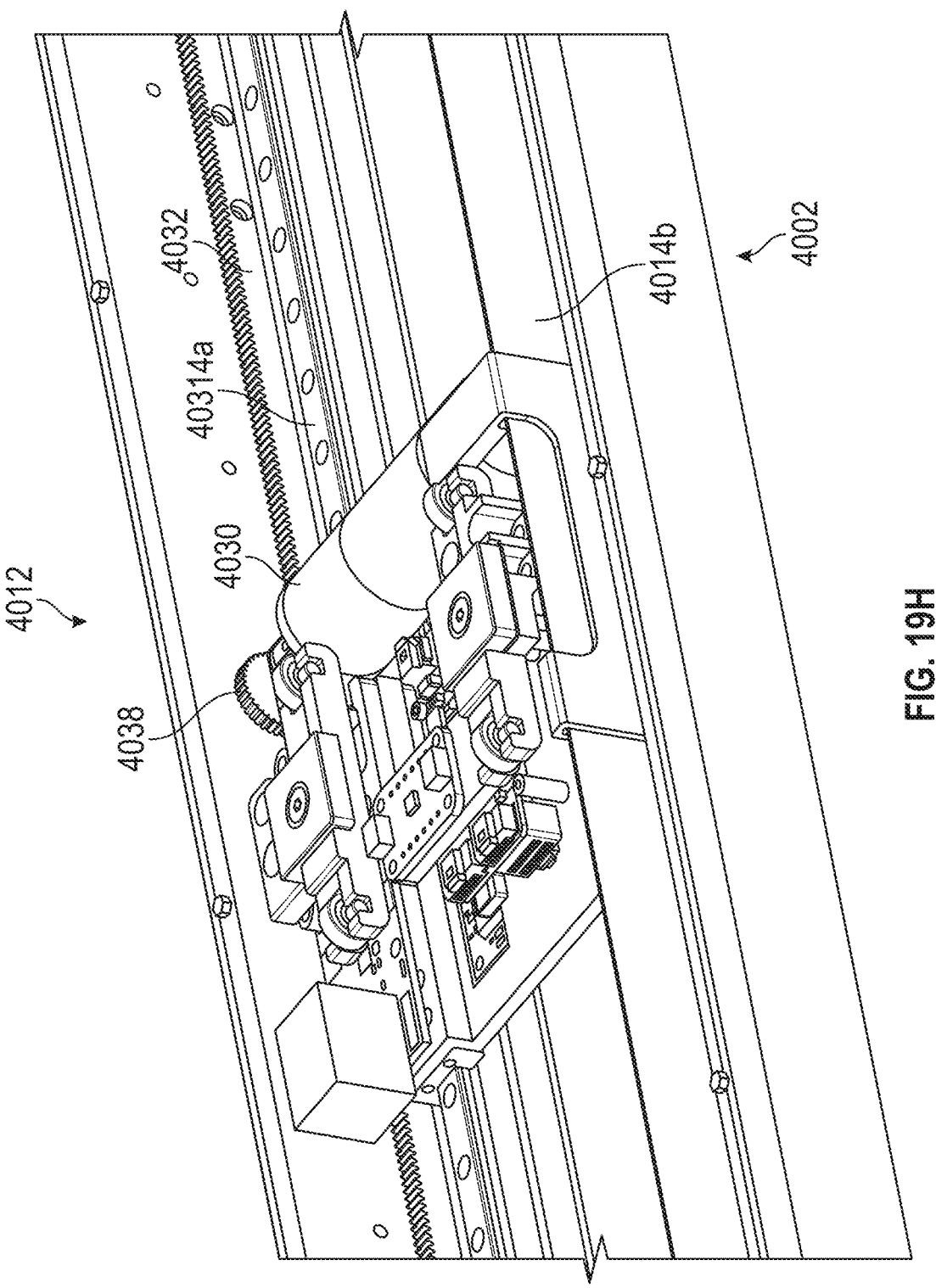
Figure 19I:
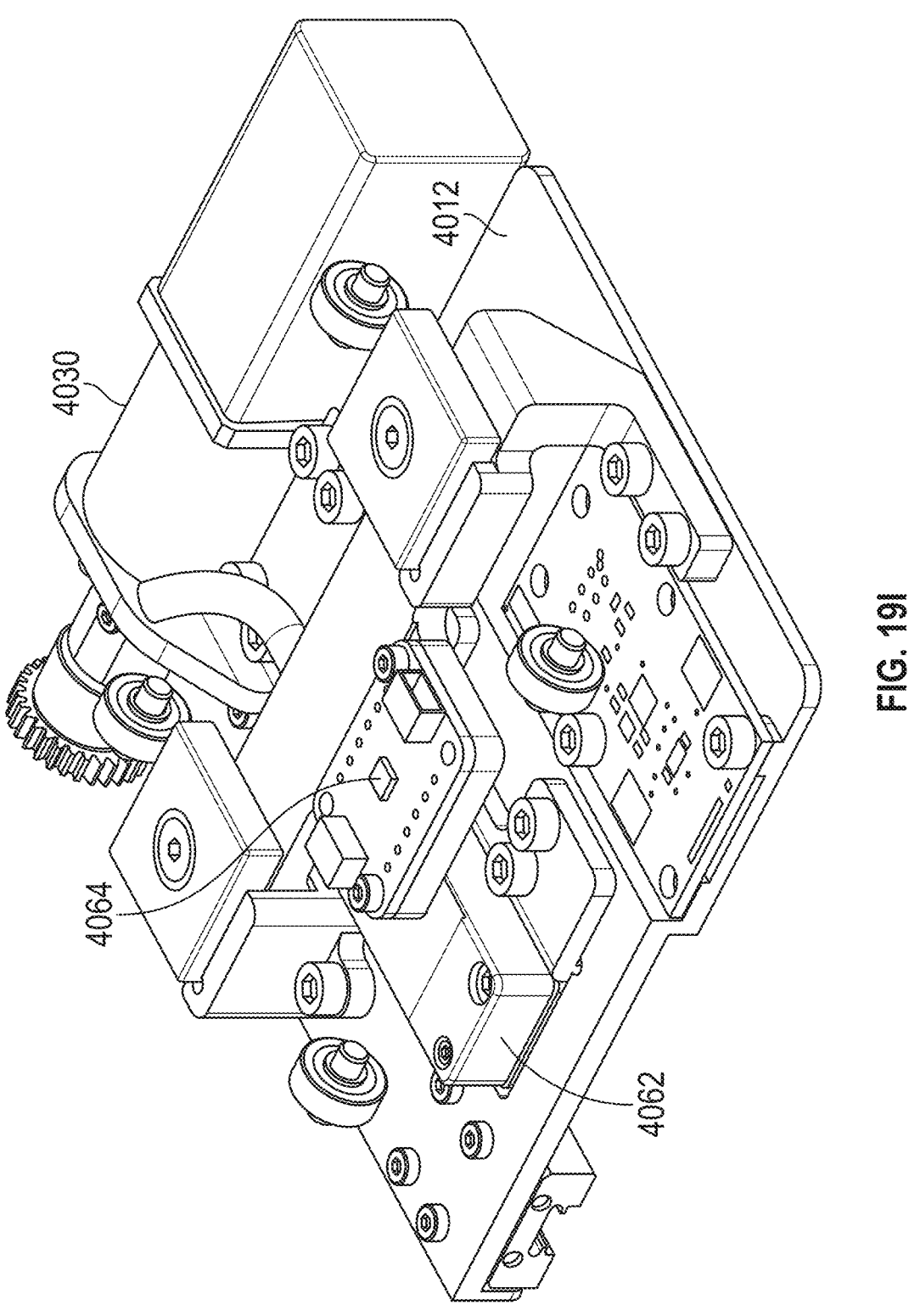
Figure 19J:
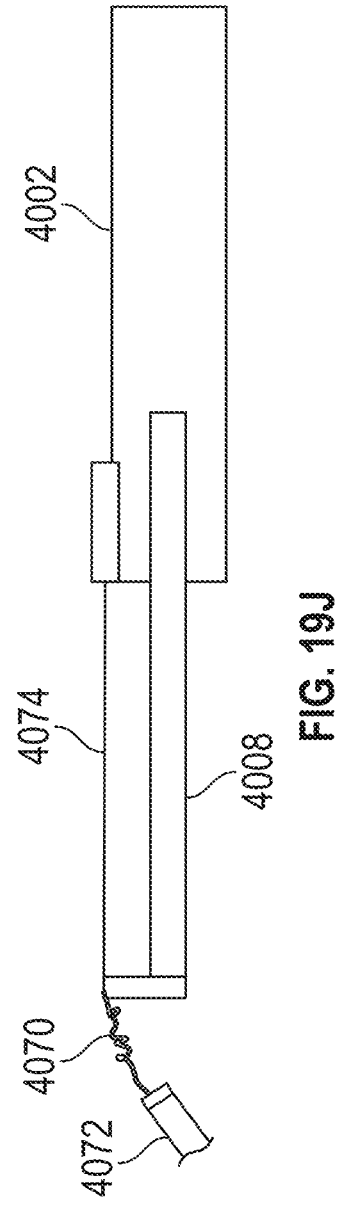

FIG. 19A depicts a top perspective view of the control system 4000. FIG. 19B depicts another top perspective view of the control system 4000. FIG. 19C depicts a bottom perspective view of the control system 4000. FIG. 19D depicts a top view of the control system 4000. FIG. 19E depicts a partial top perspective view of the control system 4000. FIG. 19F depicts another bottom perspective view of the control system 4000. FIG. 19G depicts a partial bottom perspective view of the control system 4000. FIG. 19H depicts a partial top perspective view of the control system 4000. FIG. 19I depicts a top perspective view of a hug adapter 4012 of the control system 4000. FIG. 19J depicts a side schematic view of the control system 4000.

In some embodiments, the drive table 4002 can be rotated, translated in an axial direction (e.g., proximally and distally), and/or translated in a vertical direction (e.g., up and down). Other embodiments of the robotic control system 4000 can be configured to translate and/or rotate The axial direction is the direction that is collinear with an axial centerline of an interventional device supported by or coupled with the drive table. The vertical direction is the direction that is orthogonal to the axial direction and orthogonal to the ground surface. As will be described in greater detail, moving the drive table 4002 in the axial direction can result in movement of the hub adapters (and any of the hubs and interventional devices coupled thereto) in the axial direction (proximally and distally).

In certain embodiments, the telescoping drive table 4002 can be translated axially to translate one or more interventional devices coupled to the drive table 4002 axially during a neurovascular (or other) procedure. Axial translation of the drive table 4002 to axially translate an interventional device can allow for a drive table 4002 having a shorter length (e.g., between a distal end 4002a and a proximal end 4002b) in comparison to a drive table that does not axially translate. For example, at least some of the axial motion of an interventional device coupled to the drive table 4002 relative to a patient reference point (e.g., a femoral access point 24) may be accomplished by moving the drive table 4002 while the interventional device is coupled to the drive table 4002 instead of moving the interventional device relative to the drive table 4002.

In embodiments having a drive table that does not axially translate, each interventional device of an interventional device assembly (e.g., interventional device assembly 2900) may move along and relative to the drive table during a neurovascular procedure. In such embodiments, the drive table may have a sufficient length to accommodate a desired range of motion of each interventional device.

In embodiments having an axially translatable telescoping drive table 4002, at least some of the desired range of axial motion for one or more interventional devices can be provided by axial movement of the drive table 4002.

In some embodiments, the position of one of the interventional devices coupled to the drive table 4002 can be fixed relative to the drive table (for example, by a hub adapter fixed to the drive table 4002) so that the axially range of motion desired for that interventional device is accommodated by axial movement of the drive table 4002. Such a telescoping drive table 4002 may thus reduce the overall length of the drive table 4002 in comparison to a drive table that does not axially translate by at least a portion of the desired range of motion of the interventional device having a position fixed to the drive table 4002 (e.g., by 90%, 80%, 70%, 60%, 50%, or any other suitable percentage). The reduced length of the telescoping drive table 4002 may be beneficial for storage of the drive table 4002.

In some embodiments, the telescoping drive table 4002 can have a length of between 100 cm and 160 cm, between 110 cm and 150 cm, between 120 cm and 140 cm, about 100 cm, about 110 cm, about 120 cm, about 130 cm, about 140 cm, about 150 cm, about 160 cm or any other suitable length.

An embodiment of the robotic control system 4000 disclosed herein can include at least a guidewire hub (e.g., guidewire hub 2909) configured to adjust each of an axial position and a rotational position of a guidewire (e.g., guidewire 2907). The robotic control system 4000 of any embodiment can also include an access catheter hub (e.g., access catheter hub 2910) configured to adjust axial and rotational movement of an access catheter (e.g., access catheter 2902). The robotic control system 4000 can also include a procedure catheter hub (e.g., procedure catheter hub 2912) configured to adjust an axial position and a rotational position of a procedure catheter (e.g., procedure catheter 2904). The robotic control system 4000 can also include a guide catheter hub (e.g., guide catheter hub 2914) configured to control axial movement of a guide catheter (e.g., guide catheter 2906). In some embodiments, the access catheter hub can be further configured to laterally deflect a distal deflection zone of the access catheter. In some embodiments, the procedure catheter hub can be further configured to laterally deflect a distal deflection zone of the procedure catheter. Each of the foregoing interventional devices and hubs may be coupled with a hub adapter of the drive table 4002. Any other components, features, or other details regarding the robotic control system embodiments or interventional devices disclosed above can be combined with any of the features of any of the robotic control system 4000 embodiments or interventional devices disclosed below.

With reference to FIGS. 19A-19H, in any embodiments disclosed herein, the robotic control system 4000 can include a drive table 4002, a base structure 4004, and an arm 4006 coupled with the base structure 4004 and the drive table 4002. As described in further detail herein, in certain embodiments, the drive table 4002 can be configured to move in an axial direction (e.g., along a desired axis of catheter insertion and/or along the longitudinal axis of the drive table 4002). In certain embodiments, the drive table 4002 can be configured to move relative to the base structure 4004 (e.g., in the axial direction). The axial direction is represented by arrow A1 in FIG. 19D, which points in both directions along the longitudinal axis of the drive table 4002.

In some embodiments, the arm 4006 can be configured to move the drive table 4002 (and any interventional devices coupled thereto) in at least an axial direction along a desired axis of catheter insertion. In some embodiments, moving the drive table 4002 in the axial direction along the desired axis of catheter insertion includes moving the drive table 4002 relative to the base structure 4004.

Additionally, some embodiments of the robotic control system 4000 can be configured to move the drive table 4002 in a vertical direction (e.g., relative to the base structure 4004) in response to an input provided by a user of the robotic control system. The vertical direction is represented by arrow A2 in FIG. 19A, which points in both directions along an axis that is orthogonal to a ground surface or to a bottom surface 4004a of the base structure 4004. In some embodiments, the drive table 4002 can be configured to move in the vertical direction from at least a first height from a ground surface to at least a second height from the ground surface, wherein the second height can be greater than the first height.

In some embodiments, the arm 4006 can be also configured to move the drive table 4002 (and any interventional devices coupled thereto) in an orthogonal direction (e.g., relative to the base structure 4004) in response to an input provided by a user of the robotic control system, wherein the orthogonal direction is orthogonal to the axial direction and is orthogonal to the vertical direction. The orthogonal direction is represented by arrow A3 in FIG. 19D, which points in both directions in a horizontal direction that is orthogonal to the axial direction of the drive table 4002.

In some embodiments, the drive table 4002 (and any interventional devices coupled thereto) can be configured to rotate (e.g., relative to the base structure 4004) to any desired angle relative to a ground surface, for example and without limitation, so that the drive table 4002 moves along an axis that is angled relative to a horizontal plane. For example and without limitation, some embodiments of the robotic control system 4000 can have a rotatable joint 4022 that is configured to rotate about an axis that is parallel to a ground surface or parallel to a bottom surface of some embodiments of the base structure 4004 (such as the illustrated embodiment). In some embodiments, the drive table 4002 can be configured to rotate to an angle or orientation that is orthogonal to the ground surface (e.g., to an upright, stored position). In other words, in some embodiments, the drive table 4002 can be configured to rotate between at least a first position in which the drive table 4002 is generally parallel to a ground surface and at least a second position in which the drive table 4002 is orthogonal to the first position, or within 10 degrees or approximately 10 degrees of orthogonal to the ground surface. This can be useful for moving the drive table 4002 to a stored position to make the robotic control system 4000 more compact when not being used and also more compact for moving or transporting the robotic control system 4000.

In some embodiments, the drive table 4002 can be configured to rotate to an angle or orientation suitable for advancing interventional devices coupled to the drive table into the access point while positioning the drive table 4002 above the anatomy of the patient. For example, the drive table 4002 can be rotated so that the proximal end 4002b of the drive table 4002 is vertically above the distal end 4002a of the drive table 4002 to position a proximal section of the drive table 4002 vertically above the feet of the patient.

In some embodiments, the drive table 4002 can be foldable to reduce an overall length of the drive table 4002 in a stowed configuration, thus providing a more compact robotic surgical system that can provide space savings as compared to conventional surgical robots.

In some embodiments, the base structure 4004 can be configured to be coupled with a surgical bed. In some embodiments, the base structure 4004 can be configured to be mounted to a ground surface.

In some embodiments, the robotic control system 4000 can include a first hub adapter 4012a coupled with the drive table 4002, the first hub adapter 4012a can be configured to couple with and/or move a first hub coupled with a first interventional device (which can be any of the interventional devices disclosed herein and/or that are suitable for use in any interventional procedures) in at least the axial direction (e.g., relative to the base structure 4004) in response to an input provided by a user of the robotic control system. In some embodiments the first hub adapter 4012a can be configured to couple with and/or move a guide catheter hub (e.g., guide catheter hub 2914) coupled to a guide catheter (e.g., guide catheter 2906).

In some embodiments, the robotic control system 4000 can include a second hub adapter 4012b coupled with the drive table 4002. The second hub adapter 4012b can be configured to couple with and/or move a second hub coupled with a second interventional device (which can be any of the interventional devices disclosed herein and/or that are suitable for use in any interventional procedures) in at least the axial direction (e.g., relative to the base structure 4004) in response to an input provided by a user of the robotic control system. In some embodiments the second hub adapter 4012b can be configured to couple with and/or move a procedure catheter hub (e.g., procedure catheter hub 2912) coupled to a procedure catheter (e.g., procedure catheter 2904).

In some embodiments, the robotic control system 4000 can include a third hub adapter 4012c coupled with the drive table 4002. The third hub adapter 4012c can be configured to couple with and/or move a third hub coupled with a third interventional device (which can be any of the interventional devices disclosed herein and/or that are suitable for use in any interventional procedures) in at least the axial direction (e.g., relative to the base structure 4004) in response to an input provided by a user of the robotic control system. In some embodiments the third hub adapter 4012c can be configured to couple with and/or move an access catheter hub (e.g., access catheter hub 2910) coupled to an access catheter (e.g., access catheter 2902).

In some embodiments, the robotic control system 4000 can include a fourth hub adapter 4012d coupled with the drive table 4002. The fourth hub adapter 4012d can be configured to couple with and/or move a fourth hub coupled with a fourth interventional device (which can be any of the interventional devices disclosed herein and/or that are suitable for use in any interventional procedures) in at least the axial direction (e.g., relative to the base structure 4004) in response to an input provided by a user of the robotic control system. In some embodiments the fourth hub adapter 4012d can be configured to couple with and/or move a guidewire hub (e.g., guidewire hub 2909) coupled to a guidewire (e.g., guidewire 2907).

In some embodiments, the first hub adapter 4012a can be coupled at a fixed position to the drive table 4002 such that a position of the first hub adapter 4012a relative to the drive table 4002 does not change (e.g., the first hub adapter 4012a does not move relative to the drive table). In this configuration, the robotic control system 4000 can be configured to move the first hub adapter 4012a (and any hub and interventional device coupled thereto) axially (e.g., proximally or distally) relative to a patient reference point (e.g., a femoral access point) by maintaining the first hub adapter 4012a in a fixed position on the drive table 4002 and moving the drive table 4002 axially (e.g., proximally or distally) relative to the patient reference point, thereby effectively moving the first hub adapter 4012a relative to the patient reference point. In this way, the drive table 4002 can be moved axially to move an interventional device coupled at a fixed position to the drive table 4002 (e.g., via a hub coupled to the hub adapter 4012a). The interventional device may be a distal most interventional device (e.g., a guide catheter 2906). In other embodiments, the interventional device coupled at a fixed position to the drive table 4002 can be a proximal most interventional device (e.g., a guidewire 2907).

In some embodiments, any of the second hub adapter 4012b, the third hub adapter 4012c, and the fourth hub adapter 4012d (and any interventional devices/hubs coupled thereto) can be configured to move axially relative to the drive table 4002 (e.g., by moving proximally or distally along the drive table 4002). In some embodiments, any of the second hub adapter 4012b, the third hub adapter 4012c, and the fourth hub adapter 4012d (and any interventional devices/hubs coupled thereto) can be configured to move axially relative to the first hub adapter 4012a (and any interventional device/hub coupled thereto) (e.g., by moving proximally or distally along the drive table 4002).

For example, with reference to the interventional device assembly 2900, one or more of the procedure catheter 2904 (e.g., coupled to the hub adapter 4012b via hub 2912), the access catheter 2902 (e.g., coupled to the hub adapter 4012c via hub 2910), and the guidewire 2907 (e.g., coupled to the hub adapter 4012d via hub 2909) can move axially along the drive table 4002 relative to the guide catheter 2906 which can be coupled to the drive table 4002 at a fixed position (e.g., coupled to the hub adapter 4012a via hub 2914). In such embodiments, the guide catheter 2906 can be axially movable via axial movement of the drive table 4002.

In certain embodiments, the robotic control system 4000 can include a control mechanism having one or more user controls for controlling the movement of the interventional devices coupled to the hub adapters 4012a-d by controlling movement of the hub adapters 4012a-d. For example, a user may operate a first control to control axial movement of the drive table and, consequently, axial movement of the first hub adapter 4012a and the interventional device coupled thereto. The user may operate a second control to control axial movement of the second hub adapter 4012b and the interventional device coupled thereto along the drive table 4002, a third control to control axial movement of the third hub adapter 4012c and the interventional device coupled thereto along the drive table 4002, and a fourth control to control axial movement of the hub adapter 4012d and the interventional device coupled thereto along the drive table 4002.

In some embodiments, in response to movement of the drive table 4002 and/or a user control operation to control movement of the drive table 4002, the robotic control system 4000 can be configured to adjust the positions of the hub adapters that are movable along the drive table 4002 (e.g., hub adapters 4012b-d) and the interventional devices coupled thereto relative to a patient reference point (e.g., access point 24) to correspond to the positions they would be in the absence of movement of the drive table 4002. For example, the robotic control system 4000 can be configured to adjust the positions of the hub adapters that are movable along the drive table 4002 (e.g., hub adapters 4012b-d) and the interventional devices coupled thereto relative to a patient reference point (e.g., access point 24) to correspond to the positions they would be in if each of the hub adapters 4012a-d were independently movable relative to a drive table (e.g., as discussed with respect to drive table 20) herein.

For example, in any embodiments disclosed herein, in the absence of a user control operation for moving the second hub adapter 4012*b* (e.g., a user operating a control to axially move an interventional device coupled with the second hub adapter 4012*b*) the robotic control system 4000 can be configured to maintain the second hub adapter 4012*b* in a fixed position relative to a patient reference point (e.g., access point 24) when the drive table 4002 is moved relative to the patient reference point. For example, in certain embodiments, the robotic control system 4000 can move the second hub adapter 4012*b* relative to the drive table 4002 in a direction that is opposite to a movement of the drive table 4002 relative to the patient reference point. In other words, as the drive table 4002 is moved, such as to move the first hub adapter 4012*a* (and corresponding interventional device), the position of the second hub adapter 4012*b* relative to the patient reference point can be maintained or fixed by moving the second hub adapter 4012*b* on the drive table 4002 by an equal magnitude or speed as compared to a movement of the drive table 4002 in an opposite direction. As another example, the robotic control system 4000 can be configured to maintain the second hub adapter 4012*b* in a fixed position relative to a patient reference point when the drive table 4002 is moved in a first axial direction relative to the patient reference point by moving the second hub adapter 4012*b* in a second axial direction relative to the drive table 4002 that is opposite to the first axial direction as the drive table 4002 is moved in the first axial direction. Similarly, the robotic control system 4000 can be configured to maintain the third hub adapter 4012*c* and/or the fourth hub adapter 4012*d* (and/or any other additional hub adapters) in a fixed position relative to a patient reference point when the drive table 4002 is moved relative to the patient reference point.

In some embodiments, in response to user operation of controls to move the hub adapters 4012*a-d*, the control system 4000 can cause the hub adapters 4012*a-d* to adjust their positions relative to one another to correspond to the positions they would be in if each of the hub adapters 4012*a-d* were independently movable relative to a drive table (e.g., as discussed with respect to drive table 20 herein). For example, in response to a user control operation (e.g., manipulation of a first control) to move the interventional device coupled to the hub adapter 4012*a* in a distal direction by moving the drive table 4002 in the distal direction, the control system 4000 can adjust the positions of the hub adapters 4012*b-d* so that they move along the drive table in the in the proximal direction by an equal magnitude or speed.

In response to control operations to axially move the hub adapter 4012*a* (via movement of the drive table 4002) and also axially move one or more of the other hub adapters 4012*b-d*, the control system 4000 can move the hub adapters 4012*b-d* to the same position relative to a patient reference point or relative to the hub adapter 4012*a* that they would be moved to in the absence of movement of the drive table 4002. For example, if a user performs a control operation to move the hub adapter 4012*a* and the hub adapter 4012*b* distally by 5 mm, the control system may move the drive table 4002 distally by 5 mm without moving the hub adapter 4012*b* relative to the drive table 4002. If a user performs a control operation to move the hub adapter 4012*a* distally by 5 mm and the hub adapter 4012*b* distally by 6 mm, the control system 4000 may move the drive table 4002 distally by 5 mm and move the hub adapter 4012*b* distally along the drive table by 1 mm so that the hub adapter 4012*b* has moved a total of 6 mm distally relative to a patient reference point (e.g., access point 24).

During some procedures, a user may perform a control operation intended to cause the distal most interventional device (e.g., a guide catheter 2906) coupled with the hub adapter 4012*a* to move distally relative to the proximal most interventional device (e.g., a guidewire 2907) (e.g., coupled to the hub adapter 4012*d*) by a distance greater than the total length of the drive table 4002. As described above, if a user performs a control operation to move the table 4002 and hub adapter 4012*a* distally, the control system 4000 may adjust the position of the hub adapter 4012*d* by moving the hub adapter 4012*d* in the proximal direction, preferably by an equal magnitude or speed. In some procedures, the table 4002 may be able to move in a distal direction by a greater magnitude than the hub adapter 4012*d* can move proximally. In other words, while adjusting in response to movement of the table 4002, the hub adapter 4012*d* may reach a proximal most position along the table 4002 and be prevented from further movement while the table 4002 continues to move in the distal direction. In response, the control system 4000 may compensate by temporarily linking the movement of the hub adapter 4012*d* with the movement of the hub adapter 4012*a* so that the hub adapter 4012*d* moves in unison with the hub adapter 4012*a*.

For example, when linked, if the hub adapter 4012*a* is moved distally, meaning that the table 4002 is moved distally, the hub adapter 4012*d* can move distally by the same magnitude and/or at the same speed. In this situation, the hub adapter 4012*d* can move distally by the same magnitude and/or at the same speed as the hub adapter 4012*a* by maintaining its position on the table while the table 4002 moves distally. Similarly, if the hub adapter 4012*a* is moved proximally, meaning that the table 4002 is moved proximally, the hub adapter 4012*d* can move proximally by the same magnitude and/or at the same speed. In this situation, the hub adapter 4012*d* can move proximally by the same magnitude and/or at the same speed as the hub adapter 4012*a* by maintaining its position on the table while the table 4002 moves proximally.

In some embodiments, the hub adapter 4012*d* can be unlinked from the hub adapter 4012*a* (e.g., such that it adjusts in response to movements of the hub adapter 4012*a*) in response to user manipulation of a control for the hub adapter 4012*d* causing it to move independently. In certain embodiments, while the hub adapter 4012*a* and hub adapter 4012*d* are linked, the control system 4000 can track the desired relative position of the hub adapter 4012*d* relative to the hub adapter 4012*a* and/or relative to a patient reference point and adjust the hub adapter 4012*d* to the desired position once sufficient space is available along the drive table 4002.

Linking of the distal most hub adapter (e.g., hub adapter 4012*a*) and the proximal most hub adapter (e.g., hub adapter 4012*d*) may allow for a shorter drive table. As an example, in certain embodiments, a length of the drive table 4002 may be about 130 cm long. A distal most interventional device (e.g., a guide catheter 2906) may have a length of about 127 cm. A length of a section of the distal most interventional device that overlaps the drive table 40002 (e.g., when coupled to a hub coupled to the distal most hub adapter (e.g., hub adapter 4012*a*)) may be about 3 cm. A proximal most interventional device (e.g., a guidewire 2907) can have a length of about 265 cm. A section of the proximal most interventional device may extend proximally from a proximal end of a proximal most hub coupled to a proximal most hub adapter (e.g., hub adapter 4012*d*). For example, in certain embodiments, the section of the proximal most interventional device may extend between about 2 cm and about 20 cm, between about 5 cm and about 15 cm, or about 10 cm from the proximal end of the proximal most hub. In some embodiments, the proximal most hub may extend proximally from a proximal end of the drive table 4002 by about 2.5 cm in its proximal most position. In certain embodiments, a proximal most end of the proximal most interventional device may be positioned proximally from a proximal end of the drive table 4002 by a distance of between about 4.5 cm and about 22.5 cm, between about 7.5 cm and about 17.5 cm, or about 12.5 cm, when the proximal most hub adapter is in its proximal most position. In an initial configuration a distal most end of the proximal most interventional device may be proximal to a distal most end of the distal most interventional device.

While discussed with respect to the drive table 4002, linking of hub adapters and/or hubs (e.g., linking of a proximal most hub adapter and a distal most hub adapter and/or linking of a proximal most hub and distal most hub) of the drive table may be performed with any of the embodiments of drive tables described herein.

In any embodiments disclosed herein, the robotic control system can be configured to move the second hub adapter 4012*b* independently of the first hub adapter 4012*a*. Further, in any embodiments having two, three, four, five, or more hub adapters disposed on the drive table 4002, the robotic control system 4000 can be configured such that each of the hub adapters is independently controllable and movable relative to the other hub adapters. For example and without limitation, each of the hub adapters 4012*a-d* on the drive table 4002 (including or, in some embodiments, excluding, the first hub adapter 4012*a*) can have an independently controllable motor 4030 or other actuator configured to independently move the hub adapter 4012*a-d* relative to the drive table 4002.

In an embodiment having a first hub adapter 4012*a*, a second hub adapter 4012*b*, a third hub adapter 4012*c*, and a fourth hub adapter 4012*d*, the first hub adapter 4012*a* can be fixed to the drive table 4002 and the second hub adapter 4012*b*, the third hub adapter 4012*c*, and the fourth hub adapter 4012*d* can each have an independently controllable motor 4030 or actuator configured to independently move the second hub adapter 4012*b*, the third hub adapter 4012*c*, and the fourth hub adapter 4012*d* relative to the drive table 4002 and the first hub adapter 4012*a*.

In another embodiment having a first hub adapter 4012*a*, a second hub adapter 4012*b*, a third hub adapter 4012*c*, and a fourth hub adapter 4012*d*, the first hub adapter 4012*a*, the second hub adapter 4012*b*, the third hub adapter 4012*c*, and the fourth hub adapter 4012*d* can each have an independently controllable motor or actuator configured to independently move the first hub adapter 4012*a*, the second hub adapter 4012*b*, the third hub adapter 4012*c*, and the fourth hub adapter 4012*d* relative to the drive table 4002. Any embodiment disclosed herein can also have a fifth hub adapter 4012 (not shown in the figures).

As mentioned, in some embodiments, the second hub adapter 4012*b*, third hub adapter 4012*b*, and fourth hub adapter 4012*c* can each be configured to move in the axial direction relative to the drive table 4002 in response to an input provided by a user of the robotic control system.

In some embodiments, one or more of the second hub adapter 4012*b*, the third hub adapter 4012*c*, and the fourth hub adapter 4012*d* can be configured to move in the axial direction relative to the drive table 4002 via a linear actuator (e.g., a rack and pinion linear actuator) in response to an input provided by a user of the robotic control system. With reference to FIG. 19H, the rack and pinion arrangement can have a rack (or straight gear) 4032 and a pinion gear 4038 coupled to a shaft of the motor 4030. For example and without limitations, the second hub adapter 4012*b* can have a motor 4030 and a pinion gear 4038*b* that can engage the rack 4032. The third hub adapter 4012*c* can have a motor 4030 and a pinion gear 4038*c* that can also engage the rack 4032. Similarly, the fourth hub adapter 4012*d* can have a motor and a pinion gear that can also engage the rack 4032. Each hub adapter 4012*b-d* can have its own unique motor and pinion gear to allow for independent movement of each hub adapter 4012*b-d*.

As shown in FIG. 19E, in some embodiments the hub adapters 4012*b-d* can be coupled to and move axially along a rail or linear guide 4014*a* and/or a rail or linear guide 4014*b*. The linear guide 4014*a* and/or linear guide 4014*b* can guide and/or constrain the hub adapters 4012*b-d* to move axially (e.g., proximally and distally) along a linear path when moved by linear actuator.

In any embodiments, the second hub adapter 4012*b*, the third hub adapter 4012*c*, and/or the fourth hub adapter 4012*d* (and/or any other hub adapter) can be configured to move in the axial direction relative to the drive table 4002 using a belt drive system, a lead screw system, a ball screw system, or any other suitable drive system.

Figure 21:
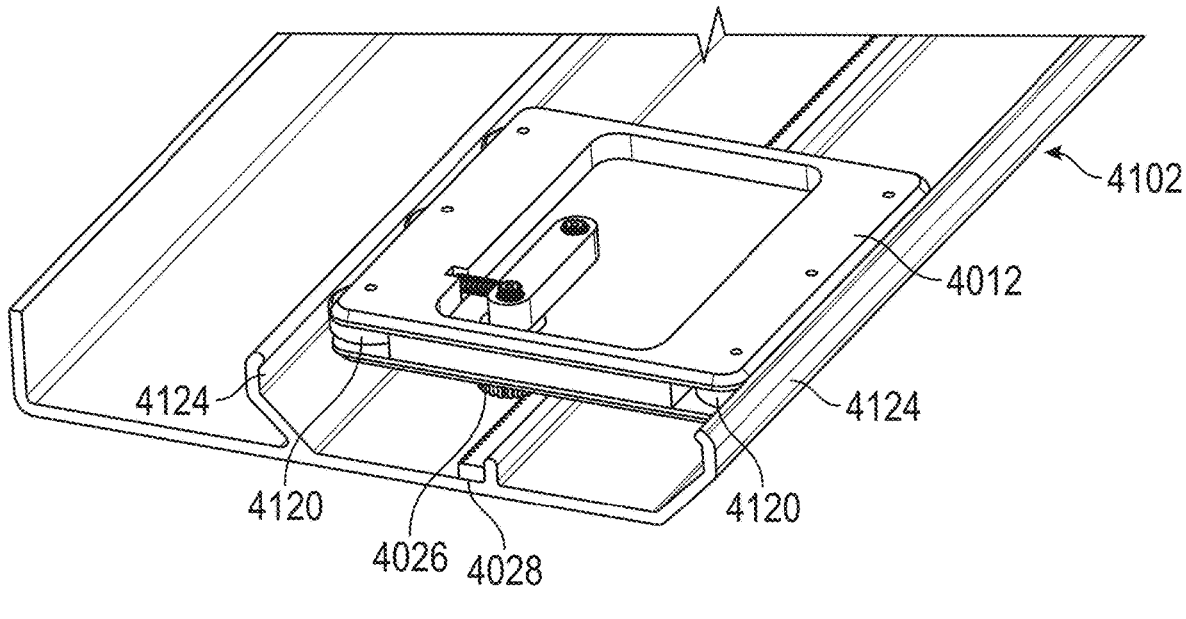
FIG. 21 shows a portion of another embodiment of a robotic control system.

Alternatively, in some embodiments and with reference to FIG. 21, the hub adapter 4012 (which may be any of the hub adapters described herein) can have a plurality of wheels 4120 (e.g., low friction wheels) configured to move along one or more rails 4124 of a drive table 4102. In some embodiments, one side of the hub adapter 4012 can be spring loaded to facilitate coupling with the rails 4124.

In the embodiment of FIG. 21, the hub adapter 4012 may be configured to move in the axial direction relative to the drive table 4002 via a linear actuator (e.g., a rack and pinion linear actuator). For example, the second hub adapter 4012 can have a motor and a pinion gear 4026 that can engage a rack 4028.

While only one hub adapter 4012 is shown in FIG. 21, one of skill in the art would understand that a plurality of hub adapters may be used with the embodiment of FIG. 21. For example, hub adapters 4012*a-d* may all couple with and move along the rails 4124 or the hub adapter 4012*a* may be maintained at a fixed position while the hub adapters 4012*b-d* move along the rails 4124 (for example, if the drive table 4102 is a telescoping table). In some embodiments, the drive table 4102 does not telescope.

In some embodiments, the drive table 4102 may be a foldable drive table having two segments that are coupled at a hinge or joint that may be folded together. The coupling between the hub adapter 4012 and rails 4124 described with respect to FIG. 21 may be beneficial for a foldable drive table by allowing less precise alignment of rail sections of the rails 4124 divided at the hinge or joint upon folding and unfolding in comparison to other drive systems.

In some embodiments, prior to folding of a foldable drive table, such as drive table 4102, each of the hub adapters 4012 coupled to the drive table (e.g., hub adapters 4012*a-d*) may be moved to one side of the hinge or joint (e.g., a proximal side). After the drive table is unfolded, each of the hub adapters 4012 may be moved to a desired position along the drive table.

As shown in FIG. 19A, the first hub adapter 4012*a* can be distal to the second hub adapter 401*b*, the second hub adapter 4012*b* can be distal to the third hub adapter 4012*c*, and the third hub adapter 4012*c* can be distal to the fourth hub adapter 4012*d*. In any embodiments, the second hub adapter 4012*b* can be axially aligned with the first hub adapter 4012a such that a first interventional device coupled with the first hub and a second interventional device coupled with the second hub are coaxially aligned when the first and second hubs are coupled with the first and second hub adapters 4012a, 4012b, respectively. Additionally, in some embodiments, the third hub adapter 4012c and the fourth hub adapter 4012d can be axially aligned with the first hub adapter 4012a such that a first interventional device coupled with the first hub, a second interventional device coupled with the second hub, a third interventional device coupled with the third hub, and a fourth interventional device coupled with the fourth hub are coaxially aligned with the first interventional device coupled with the first hub when the first, second, third, and fourth hubs are coupled (e.g., magnetically coupled) with the first, second, third, and fourth hub adapters 4012, respectively. As described herein, the first interventional device, second interventional device, third interventional device, and fourth interventional device can be arranged in a concentric stack.

In some embodiments, the robotic control system 4000 can include a linear actuator 4050 configured to move the drive table 4002 (e.g., relative to the base structure 4004) in response to an input provided by a user of the robotic control system. For example and without limitation, the linear actuator 4050 can include a rack and pinion actuator having a rack (or straight gear) 4052 that extends from a proximal end 4002b of the drive table 4002 along a majority of a length of the drive table 4002 and a motor 4054 supported by the arm 4006 (directly or indirectly, such as with a bracket or brackets (e.g., the support bracket 4008)) having a pinion gear 4056 coupled with a shaft of the motor 4054, as shown in FIG. 19G, that can be configured to engage the rack 4052 and to move the drive table 4002 in the axial direction (e.g., relative to the base structure 4004) in response to an input provided by a user of the robotic control system.

In some embodiments, the rack can extend from a proximal end 4002b of the drive table 4002 along at least 70% or approximately 70% of a length of the drive table 4002, or along at least 80% or approximately 80% of a length of the drive table 4002, or along at least from 60% or approximately 60% to 90% or approximately 90% of a length of the drive table 4002. In some embodiments, the drive table 4002 can be configured to be movable in the axial direction between a proximal position and a distal position, wherein a distance between a distal end 4002a of the drive table 4002 in the proximal position and the distal end 4002a of the drive table 4002 in the distal position can be at least 80% or approximately 80%, or at least 70% or approximately 70%, or from at least 60% or approximately 60% to 90% or approximately 90%, of a length of the drive table 4002 from a proximal end of the drive table 4002 to the distal end of the drive table 4002.

In some embodiments the table 4002 can include or be coupled to a rail or linear guide 4058, as shown in FIG. 19C, which can move within carriages 4060 in response to movement of the table 4002 by the linear actuator 4050. The linear guide 4058 and carriages 4060 can constrain movement of the table 4002 to the axial directions (proximally and distally). The carriages 4060 may be part of or coupled to a support bracket 4008. The support bracket 4008 can be coupled to the base structure 4004.

In some embodiments, as shown in FIGS. 19A-H, the drive table 4002 is configured to move (e.g., axially) relative to the arm 4006 (e.g., via the linear actuator 4050). In some embodiments, the arm 4006 can be configured to provide additional or alternative axial movement to the drive table

4002. In alternative embodiments, the drive table 4002 may be axially fixed (e.g., not move axially) relative to a fixed attachment point with the base structure 4004. For example, the drive table 4002 may be coupled at a fixed attachment point with an end of the arm 4006 (e.g., at the fifth joint 4022 in some embodiments), and the arm 4006 can be configured to move the drive table 4002 axially. In such embodiments, the drive table 4002 may be axially fixed relative to the fixed attachment point. In such embodiments, the joints of the robotic arm 4006 can be used to provide the desired axial motion. Such embodiments may be beneficial for allowing a simpler application of a sterile barrier between the robotic control system 4000 and the patient (e.g., by allowing axial movement without moving seams that can be covered and uncovered during motion) in comparison to embodiments in which the drive table 4002 moves axially relative to an attachment point with the arm 4006 and/or base structure 4004.

In some embodiments, the support bracket 4008 can extend distally in the axial direction away from a distal end 4002a of the drive table 4002 when the drive table 4002 is in a proximal position. As shown in FIG. 19J, the support bracket 4008 can extend to and be coupled to a boss clip 4070 configured to couple to a femoral sheath 4072. The robotic control system can also include an anti-buckling feature 4074 (which may be the same or similar to any of the anti-buckling features described herein) coupled at a distal end thereof with the support bracket 4008. The anti-buckling feature 4074 can be configured to stiffen a portion of an interventional device supported by the drive table 4002 spanning from the drive table 4002 to the boss clip 4070 supported by the support bracket 4008. In some embodiments, the support bracket 4008 can be configured to couple the anti-buckling feature to a flexible sheath sleeve that can be configured to couple with a femoral sheath 4072.

Figure 20:
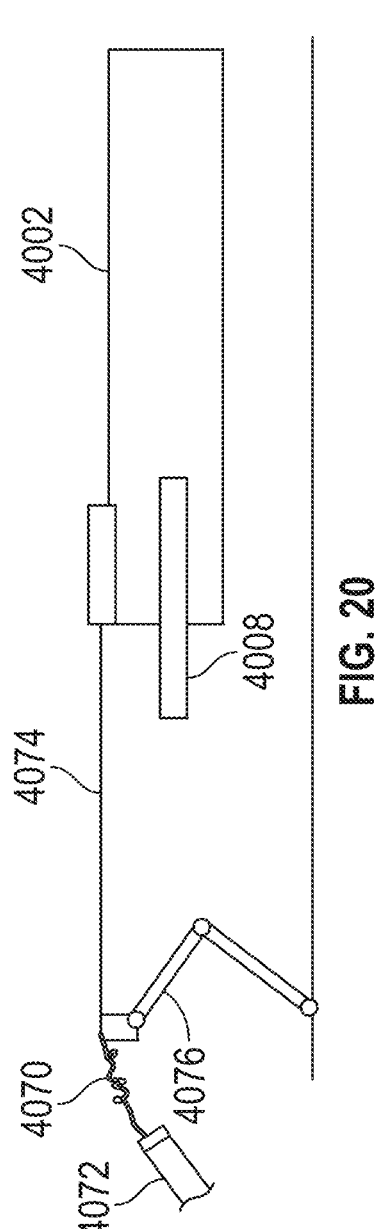
FIG. 20 shows another embodiment of a robotic control system.

In some alternative embodiments, as shown in FIG. 20, the support bracket 4008 does not extend to and couple to the boss clip or anti-buckling system. Instead, a separate arm 4076 may be provided to support the boss clip 4070 for the femoral sheath 4072 and/or anti-buckling feature 4074. The arm 4076 may be coupled to a surgical bed or a ground surface.

In some embodiments, the control system 4000 may have one or more sensors configured to detect an orientation of the boss clip 4070 and/or sheath 4072 relative to the table 4002 and/or interventional devices coupled thereto. The control system 4000 may be configured to adjust the position of the table 4002 (e.g., the angle, height, lateral position, etc. of the table 4002) to align the interventional devices with the boss clip 4070 and/or femoral sheath 4072.

In some embodiments, any one of the first hub adapter 4012a, the second hub adapter 4012b, the third hub adapter 4012c, and/or the fourth hub adapter 4012d (i.e., in any combination) can have an encoder 4062 configured to provide position data that can be used by a controller of the robotic control system 4000 to determine a position of each of the first hub adapter 4012a, the second hub adapter 4012b, the third hub adapter 4012c, and the fourth hub adapter 4012d. As shown in FIG. 19I the encoder 4062 can be a linear encoder positioned on a surface of the hub adapter 4012. The position data from the encoders 4062 can be used to determine the position of the hubs and/or interventional devices coupled to the hub adapters 4012a-d relative to the table 4002. Additionally or alternatively, in some embodiments, any of the motors (e.g., motors 4030) of the hub adapters, may include an encoder 4062 (e.g., a rotary to linear encoder) that may determine the position of the hub adapters based on detected motor movement.

In some embodiments, any of the hub adapters 4012a-d may include both a linear encoder positioned on the hub adapter and an encoder within the motor to provide redundancy and detect errors. For example, if a hub adapter 4012 becomes dislodged from the table 4002, the motor 4030 may still operate without causing movement of the hub adapter 4012 relative to the table. In such embodiments, the motor encoder may determine that the hub adapter 4012 is moving while the linear encoder may determine that the hub adapter 4012 is not moving, which can be used for error detection and handling.

Similarly, one or more encoders may be used to determine the position of the drive table 4002. For example, the one or more linear encoders may be positioned along the support bracket 4008. Additionally or alternatively, the motor 4054 can include one or more encoders to determine the position of the table 4002 based on detected motor movement.

The detected position of the table 4002 and detected position of the hub adapters along the table 4002 can be used to determine a position of each hub adapter relative to a patient reference point.

As described herein, in any embodiments, the first hub adapter 4012a can include a drive magnet coupled with the first hub adapter 4012a and configured to couple with a driven magnet of the first hub (e.g., through a sterile barrier) such that the driven magnet moves in response to a movement of the drive magnet, the second hub adapter 4012b can include a drive magnet coupled with the second hub adapter 4012b and configured to couple with a driven magnet of the second hub such that the driven magnet of the second hub moves in response to a movement of the drive magnet of the second hub adapter 4012b, the third hub adapter 4012c can include a drive magnet coupled with the third hub adapter 4012c and configured to couple with a driven magnet of the third hub such that the driven magnet of the third hub moves in response to a movement of the drive magnet of the third hub adapter 4012c, and the fourth hub adapter 4012d can include a drive magnet coupled with the fourth hub adapter 4012d and configured to couple with a driven magnet of the fourth hub such that the driven magnet of the fourth hub moves in response to a movement of the drive magnet of the fourth hub adapter 4012d.

In any embodiments, the robotic control system 4000 can include sensors 4064 coupled with one or more of the hub adapters or hubs and configured to measure a magnitude of a magnetic field on the sensor from the drive magnet of the hub adapter and/or the driven magnet of the hub. For example and without limitation, the sensor 4064 can be a magnetometer. In some embodiments, the drive magnet and driven magnet magnetically can be configured to couple the hub adapter with the hub when the hub is within a predetermined distance of the hub adapter in the axial direction.

In any embodiments disclosed herein, the robotic control system 4000 can include a controller or control circuit configured to control a position and a movement of the drive table 4002, and the second hub adapter 4012b, the third hub adapter 4012c, and the fourth hub adapter 4012d.

In some embodiments, the arm 4006 can include a first arm segment 4016a coupled at a proximal end thereof directly or indirectly to the base structure 4004, a second arm segment 4016b coupled at a proximal end thereof to a distal end of the first arm segment 4016a, and a third arm segment 4016c coupled at a proximal end thereof to a distal end of the second arm segment 4016b. In some embodiments, the first arm segment 4016a can be coupled with a fixed arm segment 4017 rigidly coupled with the base structure 4004.

In some embodiments, the arm 4006 can include a first joint 4020a at a proximal end of the first arm segment 4016a and a second joint 4020b at a distal end of the first arm segment 4016a, which is also at a proximal end of the second arm segment 4016b. The arm 4006 can also have a third joint 4020c at a distal end of the second arm segment 4016b, wherein the first arm segment 4016a can be configured to rotate in a horizontal plane about the first joint 4020a, the second arm segment 4016b can be configured to rotate in a horizontal plane about the second joint 4020b, and the third arm segment 4016c can be configured to rotate in a horizontal plane about the third joint 4020c.

In some embodiments, the robotic control system can include a fourth arm segment 4016d coupled at a proximal end thereof to a distal end of the third arm segment 4016c and a fourth joint 4020d at a distal end of the third arm segment 4016c. In some embodiments, the arm 4006 can have three or more, or four rotational degrees of freedom. The fourth arm segment 4016d can be configured to rotate in a horizontal plane about the fourth joint 4020d. In some embodiments, the fourth arm segment 4016d can be coupled at a distal end thereof directly or indirectly to the drive table 4002.

In some embodiments, the first joint 4020a, the second joint 4020b, the third joint 4020c, and/or the fourth joint 4020d (i.e., any combination of the joints) can be configured to independently exert a torque on the first arm segment 4016a, the second arm segment 4016b, and the third arm segment 4016c, respectively, in response to an input provided by a user of the robotic control system to cause the first arm segment 4016a, the second arm segment 4016b, and the third arm segment 4016c to rotate about the first, second, and third joint 4020s, respectively. In some embodiments, the first joint 4020a, the second joint 4020b, and the third joint 4020c can be switched between a passive state wherein the joint can be freely manually moved by a user and an active state wherein the joint can be controlled by a controller of the robotic control system 4000 so as to be configured to generate a torque force in response to an input from a user of the robotic control system 4000.

In any embodiments, the robotic control system 4000 can include a fifth joint 4022 at a distal end of the fourth arm segment 4016d, wherein the drive table 4002 can be coupled to the fifth joint 4022 and the fifth joint 4022 can be configured to rotate the drive table 4002 in vertical plane about the fifth joint 4022, as described above. In any embodiments, one or more of the joints can have a selectable brake element (not shown) that can be actuated to lock a joint in a fixed position, wherein the brake can be actuated manually or electronically.

In some embodiments, each of the joints 4020 can have an encoder configured to provide position data that can be used by the controller to determine a position of the respective joint 4020 and a position of the drive table 4002.

While a hub adapter 4012a that is maintained in a fixed position relative to the table 4002 (e.g., by being fixedly coupled thereto), is described with respect to various foregoing embodiments, in some embodiments, the hub adapter 4012a may be configured to independently move along the table (e.g., using a linear actuator system). In such embodiments, the hub adapter 4012a may be moved along the table 4002 for certain procedural steps. For example, the hub adapter 4012a may be moved proximally along with the hub adapters 4012b-d during an initial setup step so that the interventional devices coupled to the hub adapters 4012*a-d* are maintained within the sterile field during setup. In such embodiments, the control system 4000 can maintain the hub adapter 4012*a* at a fixed position relative to the table 4002 (for example, at a distal most position along the table 4002) during other procedural steps so that the hub adapter 4012*a* moves with the table 4002.

An alternative embodiment of a portion of a robotic control system 5000 having a telescoping drive table 5002 is shown in FIGS. 22A-D. As shown, the telescoping drive table 5002 can include a first table segment 5002*a* and a second table segment 5002*b* configured to telescope relative to one another. The second table segment 5002*b* may move axially (e.g., distally and proximally) relative to the first table segment 5002*a* (e.g., via a linear actuator, such as a rack and pinion linear actuator). For example, the second table segment 5002*b* can move distally from a fully nested configuration shown in FIG. 22A to an extended configuration shown in FIGS. 22C-22D. In some embodiments, the second table segment 5002*b* can be referred to as an arm, an extension, an extending member, a telescoping member, or an actuating beam.

One or more hub adapters 5012 (which can be any of the hub adapters described herein) may be configured to move along both the first table segment 5002*a* and the second table segment 5002*b*. For example, a first linear actuator 5026*a* (e.g., a rack and pinion linear actuator) can be configured to move the hub adapter 5012 linearly along the first table segment 5002*a*. The hub adapter 5012 can include or be coupled to a first set of wheels 5024*a* configured to move within a channel 5020*a* of the first table segment 5002*a* when the hub adapter 5012 moves along the first table segment 5002*a*. The channel 5020*a* and wheels 5024*a* may guide or constrain the movement of the hub adapter 5012 to axial movement (e.g., distal and proximal movement).

A second linear actuator 5026*b* (e.g., a rack and pinion linear actuator) can be configured to move the hub adapter 5012 linearly along the second table segment 5002*b*. The hub adapter 5012 can include or be coupled to a second set of wheels 5024*b* configured to move within a channel 5020*b* of the second table segment 5002*b* when the hub adapter 5012 moves along the second table segment 5002*b*. The channel 5020*b* and wheels 5024*b* may guide or constrain the movement of the hub adapter 5012 to axial movement (e.g., distal and proximal movement).

Figure 22A:
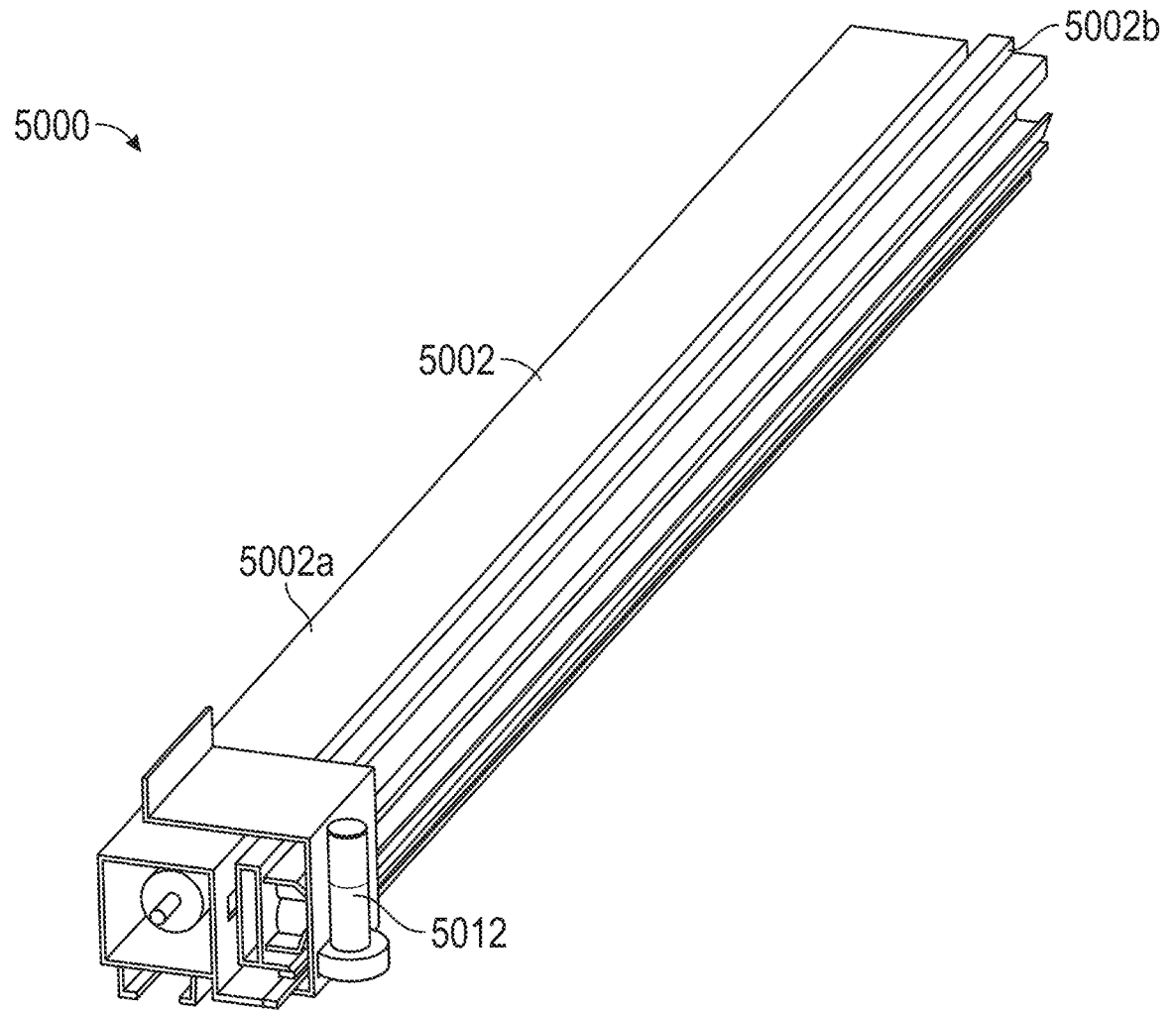
FIGS. 22A-22D show a portion of another embodiment of a robotic control system.
Figure 22B:
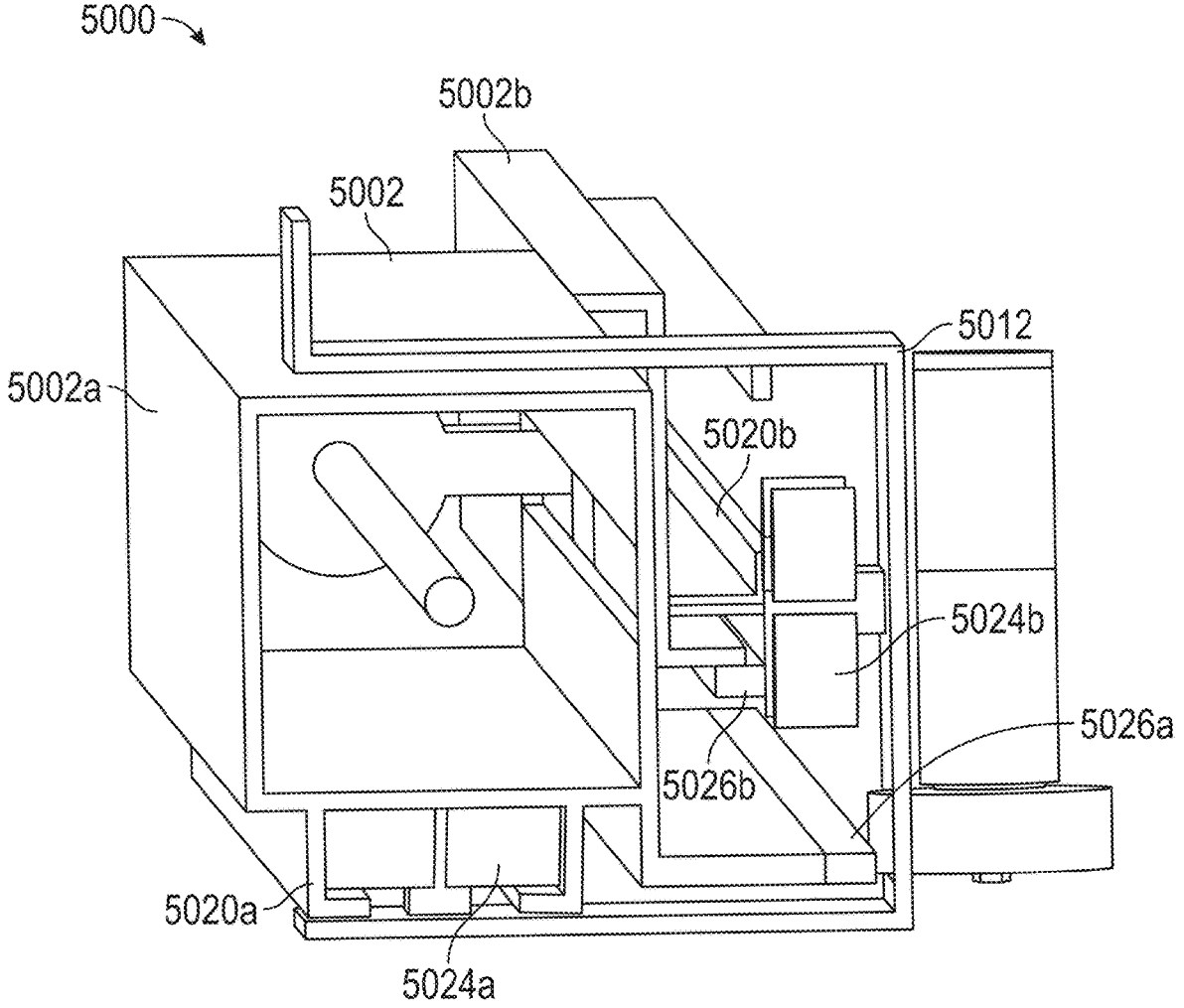
Figure 22C:
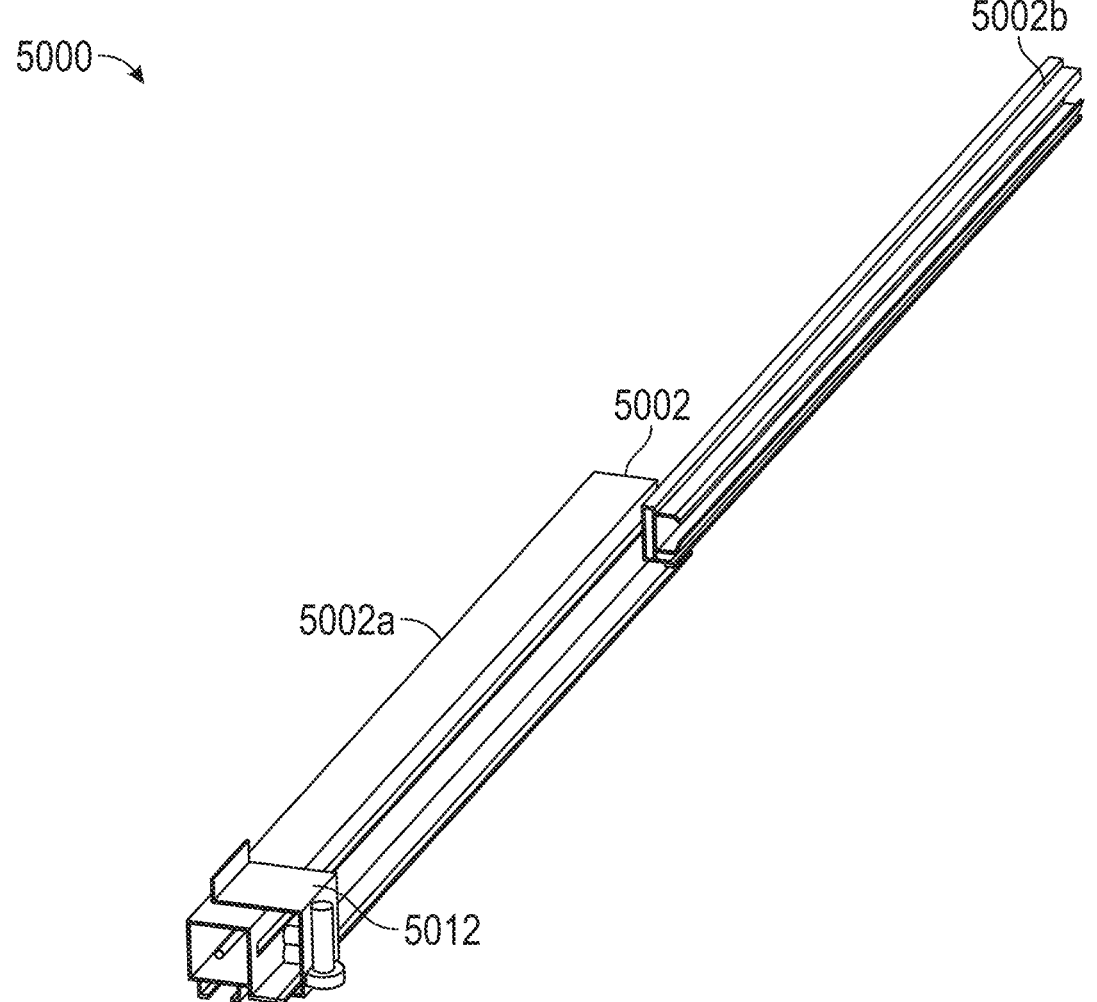
Figure 22D:
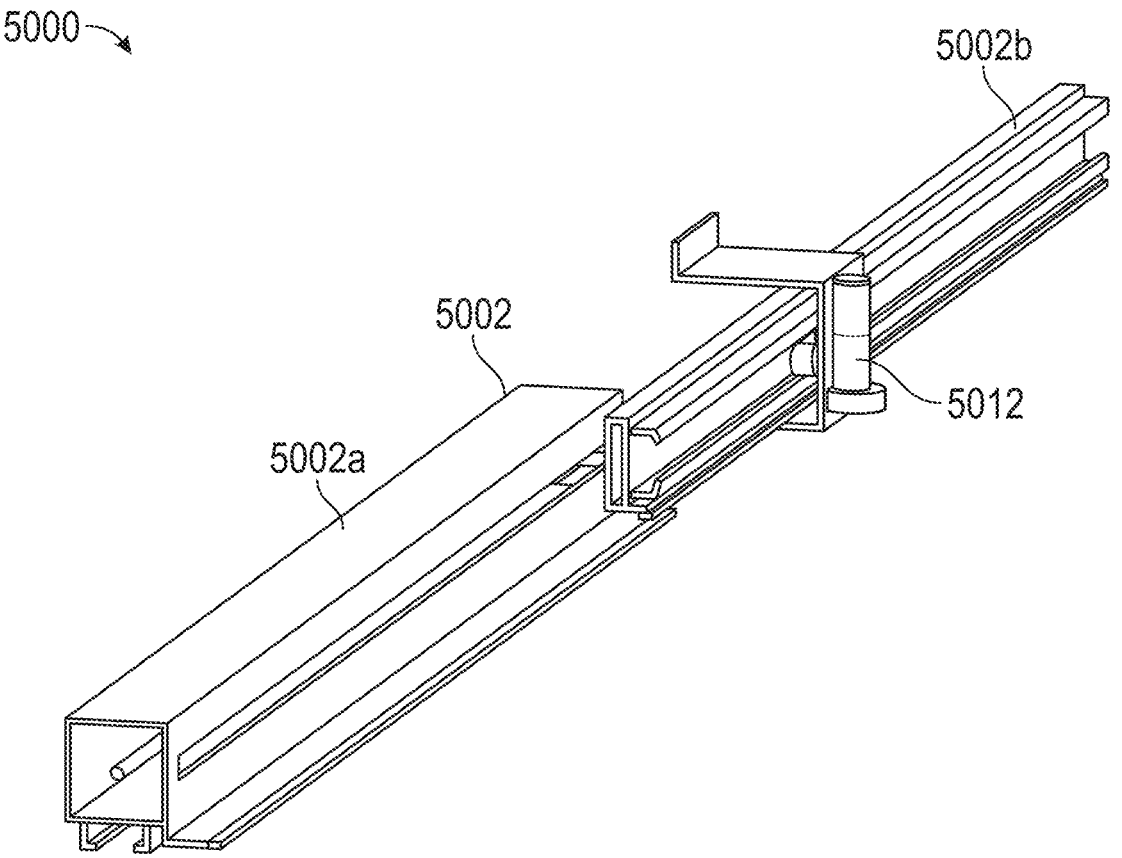

In use, when the second table segment 5002*b* is in the extended position shown in FIGS. 22C-22D relative to the first table segment 5002*a*, the hub adapter 5012 can move distally along the first table segment 5002*a* via the first linear actuator 5026*a* while the first set of wheels 5024*a* engages the first channel 5020*a*. When the hub adapter 5012 reaches a proximal end of the second table segment 5002*b*, the second linear actuator 5026*b* can engage the hub adapter 5012 to move hub adapter 5012 further distally along second table segment 5002*b*. In some embodiments, when the second linear actuator 5026*b* engages the hub adapter 5012, the first linear actuator 5026*a* may disengage from the hub adapter 5012. In some embodiments, when the hub adapter 5012 reaches a proximal end of the second table segment 5002*b*, the second set of wheels 5024*b* may engage the channel 5020*b*. If the hub adapter 5012 is moved distally beyond a distal end of the first table segment 5002*a*, the wheels 5024*a* can disengage from the channel 5020*a* (e.g., by extending distally beyond a distal end of the channel 5020*a*).

Similarly, if the hub adapter 5012 is moved proximally from the second table segment 5002*b* and reaches a proximal end of the first table segment 5002*a*, the hub adapter 5012 may disengage from the second table segment 5002*b* and engage the first table segment 5002*a*.

While one hub adapter 5012 is shown in FIG. 22B, one of skill in the art would understand that the table can include a plurality of hub adapters 5012 coupled to various hubs and/or interventional devices (e.g., the hubs and interventional devices of interventional device assembly 2900) may move along the drive table 5002. In other embodiments, a plurality of drive tables 5002 may be provided, which may each facilitate movement of different interventional devices.

In certain embodiments, a robotic control system, such as robotic control system 4000, can be used to move a drive table into and out of position before and after a treatment procedure. For example, the robotic control system 4000 may move a drive table into and out of position using the arm 4006. The drive table can be a telescoping drive table that moves axially during a treatment procedure (e.g., drive table 4002, drive table 5002) or a drive table that is stationary during a treatment procedure (e.g., drive table 20). A drive table that is stationary during a treatment procedure may have a greater length. For example, such a drive table may have a length of between about 200 cm and about 260 cm, between about 210 cm and about 250 cm, between about 220 cm and about 240 cm, about 200 cm, about 210 cm, about 220 cm, about 230 cm, about 240 cm, about 250 cm, about 260 cm, or any other suitable length.

FIGS. 24A-24G illustrate an embodiment of a telescoping drive table 6000.

Figure 24A:
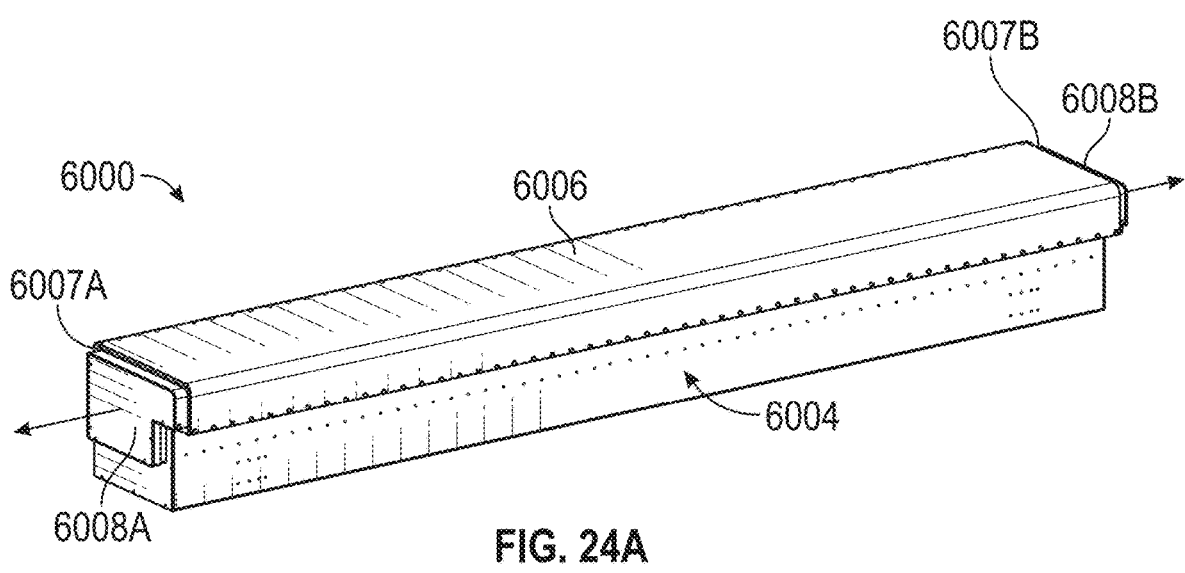
FIG. 24A illustrates a front perspective view of a telescoping drive table.

FIG. 24A illustrates a front perspective view of a telescoping drive table 6000. As shown in FIG. 24A, the telescoping drive table 6000 can include a main body 6004 and one or more telescoping members 6008A, 6008B. The telescoping members 6008A, 6008B may also be referred to as arms, extensions, extending members, extendable members, table segments, or actuating beams. The main body 6004 can further include a support surface 6006 and one or more openings 6007A, 6007B. In some embodiments, the support surface 6006 may be a sterile barrier or form at least a portion of a sterile barrier. In some embodiments, the telescoping drive table 6000 may further include a separate sterile barrier.

The telescoping drive table 6000 can be the same or similar to any of the drive tables described herein. For example, the telescoping drive table 6000 may have any of the same or similar features and/or functions as the support table 20 or the drive table 4002 described above. The telescoping drive table 6000 can transition between two or more lengths. In some embodiments, the one or more telescoping members 6008A, 6008B may extend from the main body 6004 (e.g., in a proximal and/or distal direction). The extension of the one or more telescoping members 6008A, 6008B from the main body 6004 may increase the longitudinal length of the telescoping drive table 6000 from a first length to a second length. The second length may include the length of the main body 6004 and at least a portion of the one or more telescoping members 6008A, 6008B. In some embodiments, the second length may include the sum of the length of the main body 6004 and the lengths of the one or more telescoping members 6008A, 6008B.

In some embodiments, the telescoping member(s) 6008A, 6008B can extend from a fully retracted position within the main body 6004 to a fully extended position in less than 5 seconds, less than 4 seconds, less than 3 seconds, or less than 2 seconds. This may reduce the time required to perform a procedure or setup the drive table 6000 for performing a procedure.

The main body 6004 can form an outer shell or housing of the telescoping drive table 6000 for housing internal components. For example, the main body 6004 may include one or more actuators, such as linear actuator assemblies. The main body 6004 can be defined by one or more exterior walls defining an interior cavity. The main body 6004 can have a longitudinal length. The longitudinal length of the main body 6004 can be fixed. The longitudinal length of the main body 6004 can be between 3 feet and 5 feet. For example, in some embodiments, the main body 6004 may have a longitudinal length of 4 feet. The main body 6004 can have a first end and a second end. In some embodiments, the first end may be positioned at a first longitudinal end of the main body 6004 and the second end may be positioned at a second longitudinal end of the main body 6004 opposite the first end.

The support surface 6006 can be a surface configured to support one or more hubs and/or interventional devices. In some embodiments, the support surface 6006 may be the superior or upper surface of the main body 6004.

The one or more openings 6007A, 6007B can provide access to an internal cavity of the main body 6004. The internal cavity can be defined by the main body 6004. In some embodiments, the one or more openings 6007A, 6007B may be sized to receive at the one or more telescoping members 6008A, 6008B. For example, in certain embodiments, the main body 6004 may include a single opening 6007A or 6007B configured to receive a single telescoping member 6008A or 6008B. In other embodiments, the main body can include a first opening 6007A configured to receive a first telescoping member 6008A and a second opening 6007B configured to receive a second telescoping member 6008B. In some embodiments, the one or more openings 6007A, 6007B may be positioned on lateral ends of the main body 6004. In some embodiments, the one or more openings 6007A, 6007B may be shaped to correspond to the profile of the one or more telescoping members 6008A, 6008B.

The one or more telescoping members 6008A, 6008B can transition between a collapsed state and a deployed state. The transition of the one or more telescoping members 6008A, 6008B between the collapsed state and the deployed state can adjust the overall length of the telescoping drive table 6000. Each of the one or more telescoping members 6008A, 6008B can be sized relative to the main body 6004. In some embodiments, each of the one or more telescoping members 6008A, 6008B may be sized to fit within the main body 6004. In some embodiments, the one or more telescoping members 6008A, 6008B may have the same structure or can share one or more of the same dimensions. For example, each of the one or more telescoping members 6008A, 6008B may have the same longitudinal length. In some embodiments, the one or more telescoping members 6008A, 6008B may have a longitudinal length up to half the length of the main body 6004. In some embodiments, the telescoping drive table 6000 may include two telescoping members 6008A, 6008B. In some embodiments, the one or more telescoping members 6008A, 6008B may have a first telescoping member 6008A and a second telescoping member 6008B. In some embodiments, the first telescoping member 6008A may extend from a first end of the main body 6004 and the second telescoping member 6008B may extend from a second end of the main body 6004.

The main body 6004 can slidably receive the one or more telescoping members 6008A, 6008B through the one or more openings 6007A, 6007B, respectively. Each of the one or more telescoping members 6008A, 6008B can be coupled to a corresponding linear actuator assembly housed within the main body 6004 as described in greater detail below. The one or more telescoping members 6008A, 6008B may be configured to extend linearly along an axis between a collapsed state and deployed state. In the collapsed state, the one or more telescoping members 6008A, 6008B can be contained entirely within the main body 6004 such that the overall length of the telescoping drive table 6000 can be the length of the main body 6004. In other embodiments, the one or more telescoping members 6008A, 6008B can be partially contained within the main body in the collapsed state. For example, as shown in FIG. 24A, the one or more telescoping members 6008A, 6008B can be substantially contained within the main body 6004. In the deployed state, the one or more telescoping members 6008A, 6008B can extend linearly away from the main body 6004. In some embodiments, the one or more telescoping members 6008A, 6008B may be simultaneously controlled such that the effective length (e.g., the length of the one or more telescoping members 6008A, 6008B extending outside of the main body 6004) of each of the one or more telescoping members 6008A, 6008B is the same. In some embodiments, the one or more telescoping members 6008A, 6008B may be independently controlled such that the effective length of one of the one or more telescoping members 6008A, 6008B is independent of the effective length of the other one or more telescoping members 6008A, 6008B.

In some embodiments, the collapsed state may be used for storing the telescoping drive table 6000. In some embodiments, the deployed state may be used during an operation to provide a greater length to drive one or more hubs and/or interventional devices.

In some embodiments, a sterile barrier may be positioned along or form a top surface (e.g., support surface 6006) of the telescoping drive table 6000. The sterile barrier may be configured to prevent contamination of a surgical area. The sterile barrier may be a deployable or extendable (e.g., telescoping) sterile barrier. In some embodiments, the sterile barrier may be configured to extend with the one or more telescoping members 6008A, 6008B. In a collapsed state, the sterile barrier may have a length of the main body 6004. In a deployed state, the sterile barrier may have a length corresponding to the sum of the length of the main body 6004 and the deployed length of the one or more telescoping members 6008A, 6008B. Accordingly, the sterile barrier may extend along the combined length of the telescoping drive table 6000. The sterile barrier may advantageously allow a hub to transition from a position on the main body 6004 to a position on one of the one or more telescoping members 6008A, 6008B and vice versa.

The telescoping drive table 6000 can be controlled either manually or automatically via a control system. In some embodiments, the telescoping drive table 6000 may be in a collapsed position until activated prior to a medical procedure. For example, the telescoping drive table 6000 may transition from the collapsed state to the deployed state before a patient enters the operating room. Alternatively, the telescoping drive table 6000 may transition from the collapsed state to the deployed state after a patient is prepped for surgery and positioned on an operating table. The telescoping drive table 6000 may thus advantageously conserve space within an operating room when not in use and advantageously expand when needed during a medical procedure.

Figure 24B:
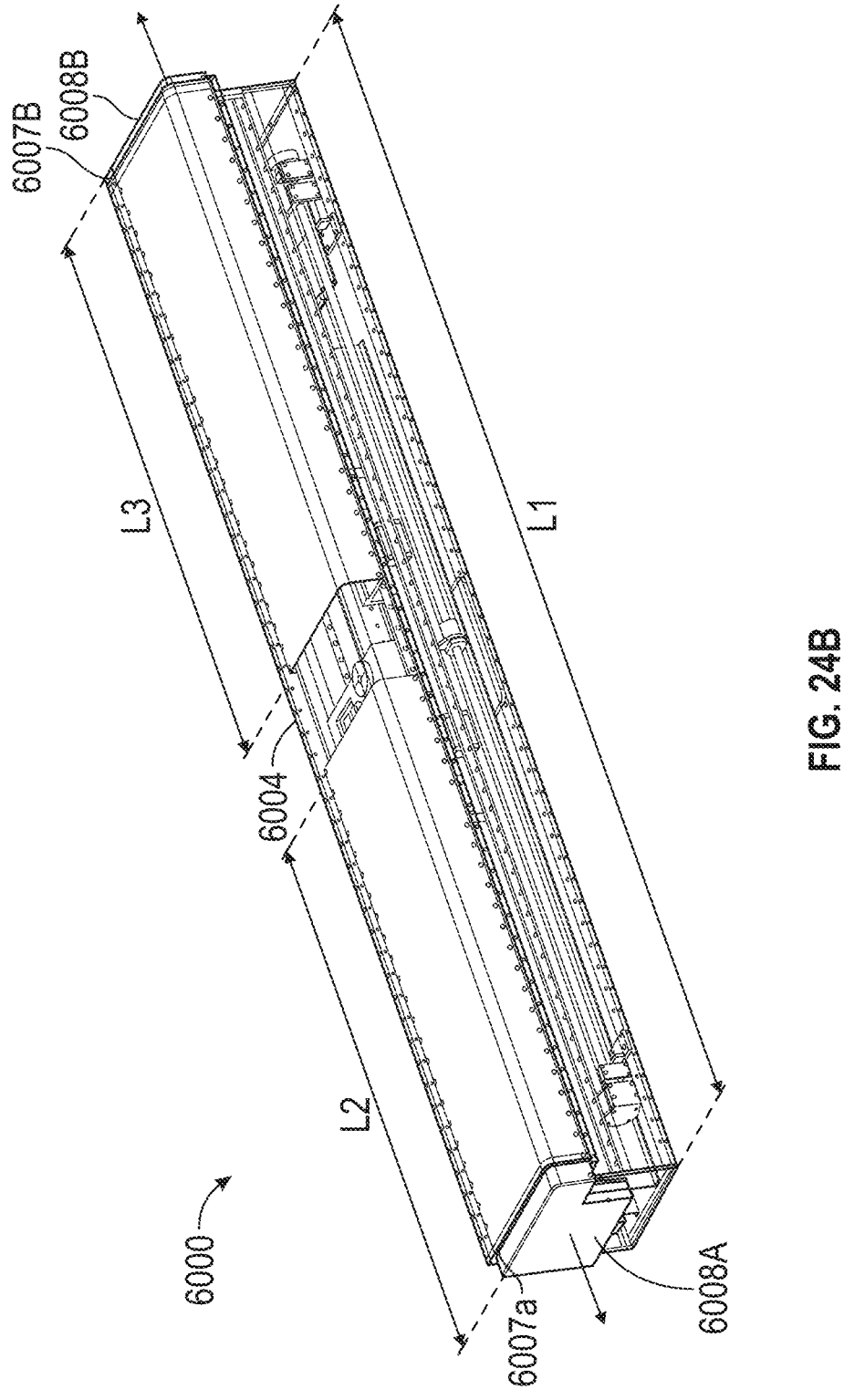
FIG. 24B illustrates a front perspective view of a telescoping drive table.

FIG. 24B illustrates a front perspective view of the interior components of the telescoping drive table 6000 in a collapsed state. The telescoping drive table 6000 can be the same as the telescoping drive table 6000 shown and described above with respect to FIG. 24A.

As further illustrated in FIG. 24B, the main body 6004 can have a longitudinal length shown in FIG. 24B as a first length L1. In some embodiments, the first length L1 of the main body 6004 may be between 3 feet and 5 feet. For example, the first length L1 may be 4 feet.

As further illustrated in FIG. 24B, the one or more telescoping members 6008A, 6008B can each have a longitudinal length represented by a second length L2 and a third length L3, respectively. In some embodiments, the second length L2 and the third length L3 may be half as long as the first length L1. For example, the second length L2 and the third length L3 may be 2 feet when the first length L1 is 4 feet. In some such embodiments, the one or more telescoping members 6008A, 6008B may be completely contained within the main body 6004 in the collapsed state. Additionally, the one or more telescoping members 6008A, 6008B can double the overall length of the telescoping drive table 6000 in the deployed state. In some embodiments, the second length L2 of the one or more telescoping members 6008 is less than half of the first length L1 of the main body 6004 (e.g., ⅓ of the length L1, ¼ of the length L1, or any other suitable length). In some embodiments, a total length of the table 6000 when the telescoping members 6008A and 6008B are fully extended can be between 1 meter and 2.7 meters.

Figure 24C:
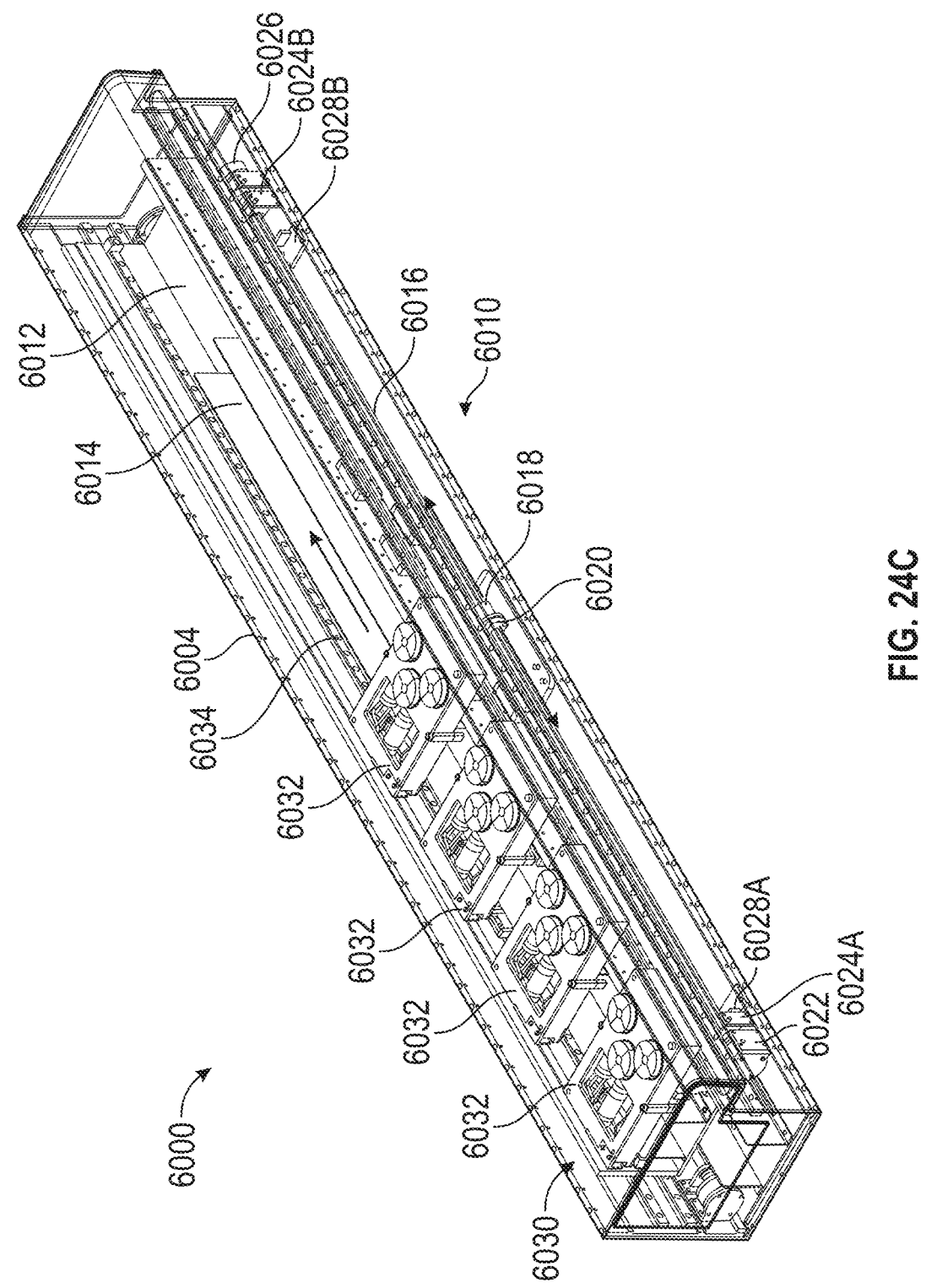
FIG. 24C illustrates a front perspective view of the internal components of the telescoping drive table of FIG. 24B.
Figure 24D:
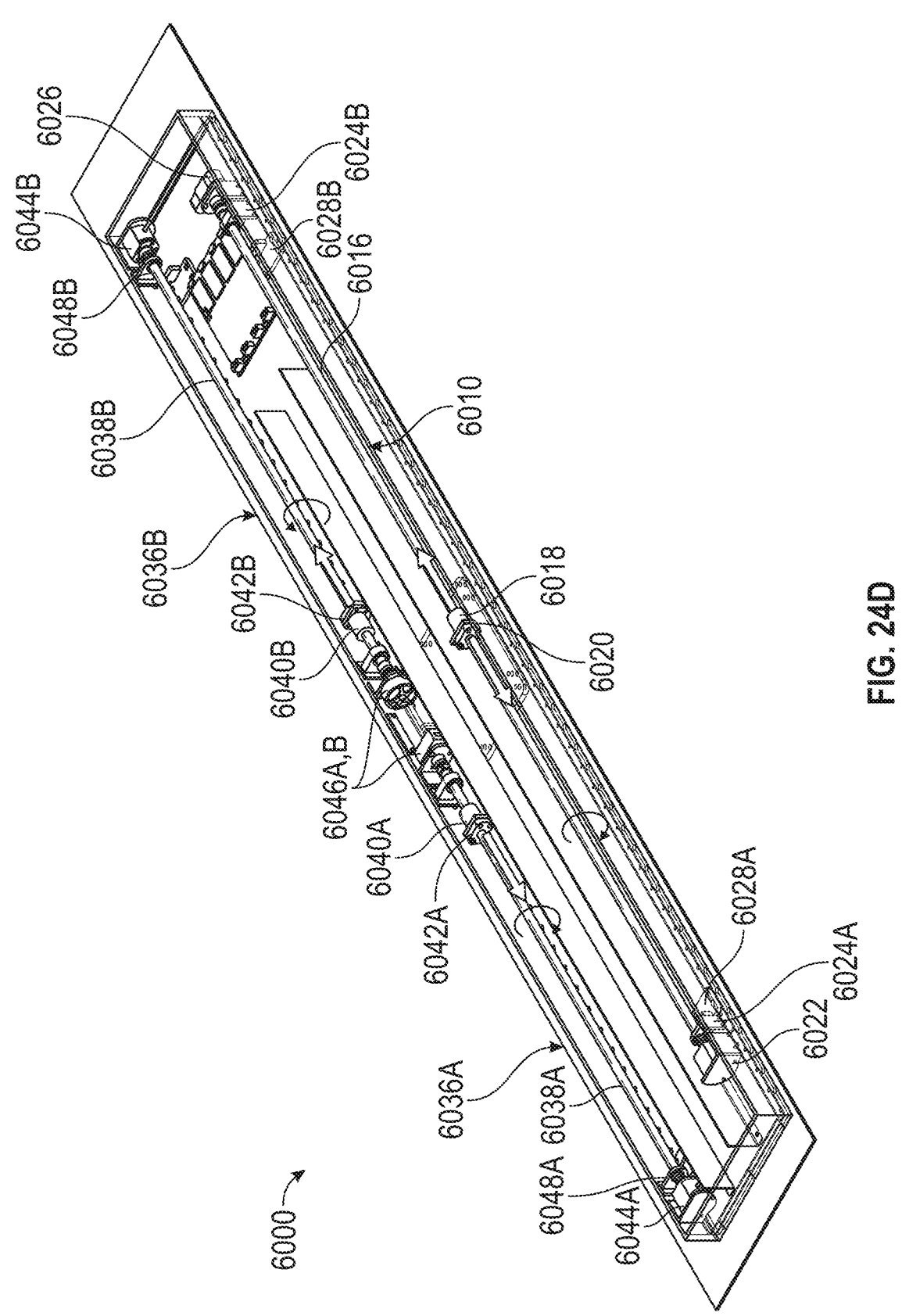
FIG. 24D illustrates a cross-sectional view of the internal components of the telescoping drive table of FIG. 24C.
Figure 24E:
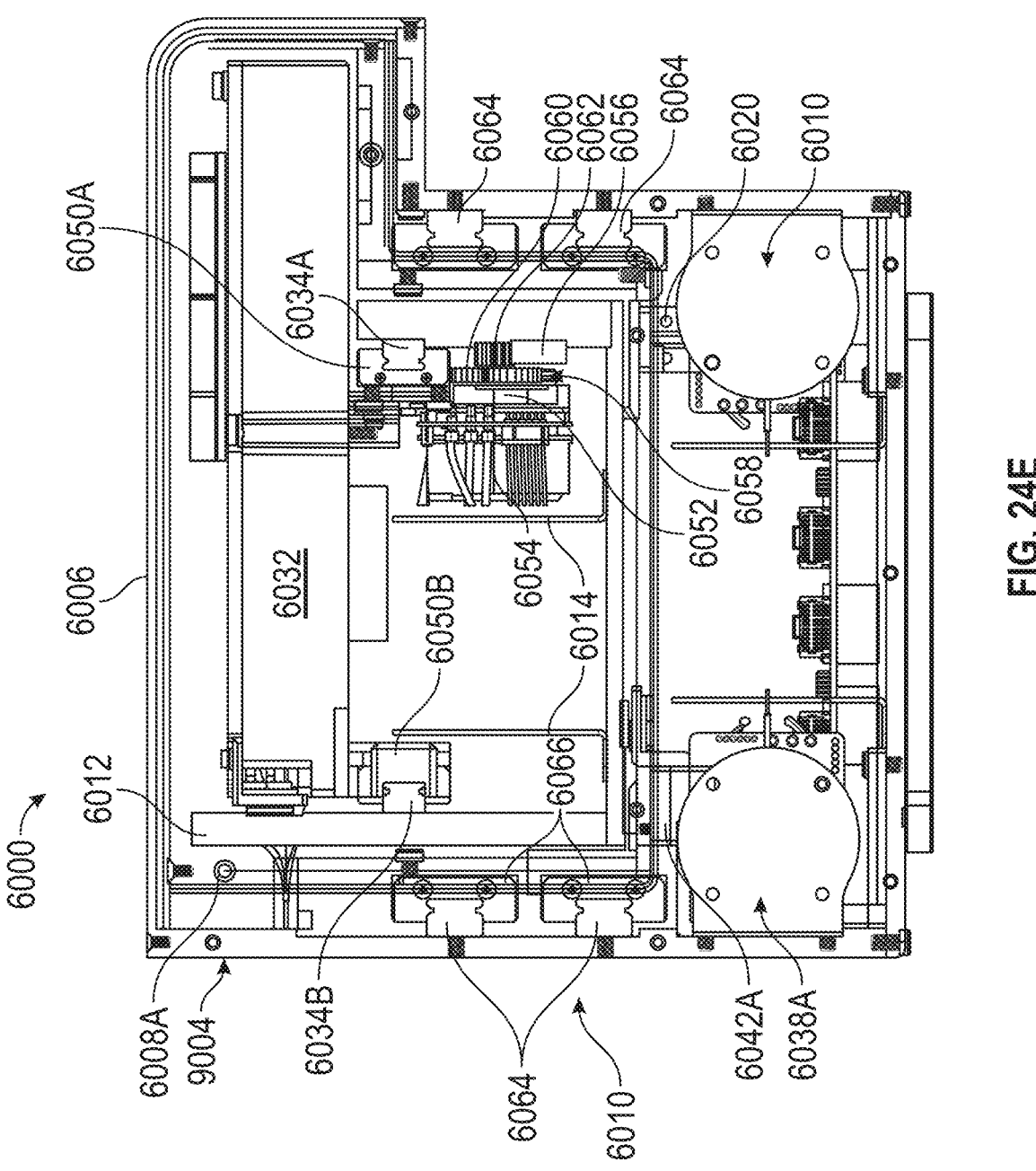
FIG. 24E illustrates a side view of the internal components of the telescoping drive table of FIG. 24B.

FIGS. 24C-24E illustrate exemplary internal components of the telescoping drive table 6000. The internal components of the telescoping drive table 6000 can include a plurality of linear actuator assemblies. The plurality of linear actuator assemblies can include a first linear actuator assembly 6010, a second linear actuator assembly 6030, and one or more third linear actuator assemblies 6036A, 6036B. The plurality of linear actuator assemblies 6010, 6030, 6036A, 6036B can be controlled independently.

The first linear actuator assembly 6010 can translate along the longitudinal length of the drive table 6000. In some embodiments, the first linear actuator assembly 6010 may translate within main body 6004 and/or the one or more telescoping members 6008A, 6008B to provide general positioning of internal components within the telescoping drive table 6000. Accordingly, the first linear actuator assembly 6010 may advantageously provide access to other internal components to the full length of the telescoping drive table 6000. For example, the first linear actuator assembly 6010 may translate a shuttle 6012 described in greater detail herein between two ends of the telescoping drive table 600. As described in further detail herein, one or more hub adapters 6032 can be coupled to and/or translate along the shuttle 6012. Accordingly, the first linear actuator assembly 6010 may translate the shuttle 6012 to change a position of one or more of the hub adapters 6032 coupled to the shuttle 6012 and/or allow for movement of the one or more hub adapters 6032 within extended portions of the telescoping drive table 6000 (e.g., within the telescoping members 6008A, 6008B) and/or along the full length of the drive table 6000.

In some embodiments, the one or more hub adapters 6032 may translate along the shuttle at speeds greater than 80 mm/second, 100 mm/second, or 120 mm/second. In some embodiments, the one or more hub adapters 6032 may translate along the shuttle at speeds up to between 100 mm/second and 160 mm/second or between 120 and 140 mm/second. In some embodiments, the one or more hub adapters 6032 may translate along the shuttle at speeds up to 80 mm/second, 100 mm/second, 110 mm/second, 120 mm/second, 130 mm/second, 140 mm/second, 150 mm/second, or 160 mm/second.

The second linear actuator assembly 6030 can translate along and relative to the first linear actuator assembly 6010 and/or along the shuttle 6012. In some embodiments, the second linear actuator assembly 6030 may provide local and/or precision positioning within the telescoping drive table 6000. For example, the second linear actuator assembly 6030 may translate one or more hub adapters 6032 along the shuttle 6012 as described in greater detail herein. As described herein, movement of the one or more hub adapters 6032 may cause movement of one or more corresponding hubs along a drive surface or support surface of the drive table 6000. Accordingly, the one or more hubs can be translated relative to the first linear actuator assembly 6010 (e.g., via movement of the one or more hub adapters along the shuttle 6012).

The one or more third linear actuator assemblies 6036A, 6036B can translate the one or more telescoping members 6008A, 6008B between the collapsed state and the deployed state described above. For example, each of the third linear actuator assemblies 6036A, 6036B can control one of the one or more telescoping members 6008A, 6008B. In some embodiments, each of the one or more third linear actuator assemblies 6036A, 6036B may be controlled together. In some embodiments, each of the one or more third linear actuator assemblies 6036A, 6036B may be controlled separately.

In some embodiments, the one or more telescoping members 6008A and 6008B can be configured to be deployed to extend from the main body 6004 at the time of setup of the drive table 6000 for a medical procedure (in response to one or more user inputs). In some embodiments, telescoping member 6008A can be configured to deploy to allow further distal movement of the shuttle 6012. For example, if distal movement of the shuttle 6012 beyond a distal end of the main body 6004 is instructed (e.g., to facilitate distal movement of one or more interventional devices coupled to the hub adapters 6032A-D beyond a distal end of the main body 6004), the telescoping member 6008A can extend distally from the main body 6008A. In some embodiments, telescoping member 6008B can be configured to deploy to allow further proximal movement of the shuttle 6012. For example, if proximal movement of the shuttle 6012 beyond a proximal end of the main body 6004 is instructed (e.g., to facilitate proximal movement of one or more interventional devices coupled to the hub adapters 6032A-D beyond a proximal end of the main body 6004), the telescoping member 6008B can extend proximally from the main body 6008A.

FIG. 24C illustrates a front perspective view of additional interior components of the telescoping drive table 6000. In particular, FIG. 24C illustrates the first linear actuator assembly 6010 and the second linear assembly 6030 contained within the main body 6004. The configuration of the interior components as shown in FIG. 24C may be the configuration of the interior components in a collapsed state. In some embodiments, in the collapsed state, the first linear actuator assembly 6010 and the second linear actuator assembly 6030 can be positioned within and/or behind the one or more telescoping members 6008A, 6008B (not shown). The telescoping drive table 6000 can be the same as the telescoping drive table 6000 shown and described above with respect to FIGS. 24A and 24B.

The first linear actuator assembly 6010 can include a shuttle 6012, a cable management system 6014, a first screw 6016, a flanged nut 6018, a shuttle bracket 6020, a motor 6022, one or more end points 6024A, 6024B, an encoder 6026, and one or more stoppers 6028A, 6028B. The shuttle 6012 can be driven by the flanged nut 6018 and the shuttle bracket 6020 along the length of the first screw 6016. The shuttle bracket 6020 can be coupled the center of the shuttle 6012. In some embodiments, the shuttle 6012 may be configured to extend beyond the longitudinal length of the main body 6004. In some embodiments, the shuttle 6012 may be configured to extend within the one or more telescoping members in a deployed state.

The shuttle 6012 can be a base support for the first linear actuator assembly 6010. In some embodiments, the shuttle 6012 may be generally "U" shaped, having two side walls extending from a horizontal base.

The cable management system 6014 can further include two walls. The cable management system 6014 can be configured to prevent cables from engaging with moving parts within the telescoping drive table 6000.

The first screw 6016 can be a feed screw (e.g., a high-efficiency feed screw) with helical threads extending along the length of the first screw 6016. The first screw 6016 can include a ball configured to make a rolling motion between the screw axis and a corresponding nut. In some embodiments, the first screw 6016 may be a linear screw. The first screw 6016 can be configured to be rotated about its longitudinal axis.

The flanged nut 6018 can be a body with a lumen extending through a longitudinal axis of the body. The flanged nut 6018 can include helical grooves extending along the length of the lumen. The helical grooves of the flanged nut 6018 can the helical threads of the first screw 6016. The flanged nut 6018 can further include one or more mounting surfaces. The one or more mounting surfaces can further define one or more openings. In some embodiments, the flanged nut 6018 may be configured to traverse along the longitudinal length of the first screw 6016.

The shuttle bracket 6020 can be a body including two or more mounting surfaces. In some embodiments, the two or more mounting surfaces may define one or more openings. In some embodiments, the shuttle bracket 6020 may be "L" shaped wherein a first mounting surface is orthogonal to a second mounting surface.

The motor 6022 can be an electric motor. The motor 6022 can include an output shaft. The output shaft can be configured to rotate in response to an electric current through the motor 6022.

The one or more end points 6024A, 6024B can include a support and a bearing. The support may define an opening configured to couple to the bearing. In some embodiments, the one or more end points 6024A, 6024B may be two end points 6024A, 6024B.

The encoder 6026 can be any device configured to track positions. In some embodiments, the encoder 6026 can be a rotary encoder configured to track the rotation of the first screw 6016. By tracking the rotation of the first screw 6016, the linear position of the flanged nut 6018 may be determined.

The one or more stoppers 6028A, 6028B may be blocks defining a mounting surface. The one or more stoppers 6028A, 6028B may be formed of a stiff material configured to prevent the flanged nut 6018 from passing the one or more stoppers 6028A, 6028B. In some embodiments, the one or more stoppers 6028A, 6028B may include two stoppers 6028A, 6028B.

The first screw 6016 can be supported by the one or more end points 6024A, 6024B. In some embodiments, the ends of the first screw 6016 may extend through the bearings of corresponding one or more end points 6024A, 6024B. Accordingly, the first screw 6016 can extend between two end points 6024A, 6024B. In some embodiments, first screw 6016 can couple to the one or more end points 6024A, 6024B before being coupled to the motor 6022. In such embodiments, the motor 6022 can be positioned laterally from the one or more end points 6024A, 6024B.

The flanged nut 6018 can be movably coupled to the first screw 6016. The grooves of the flanged nut 6018 can engage with the threads of the first screw 6016. The flanged nut 6018 can be configured to be linearly displaced along the first screw 6016 as the first screw 6016 is rotated. The rotational motion of the first screw 6016 can be converted into a linear motion of the flanged nut 6018. In some embodiments, the flanged nut 6018 can be placed on the first screw 6016 before the first screw 6016 engages at least one of the one or more end points 6024A, 6024B.

The shuttle bracket 6020 can couple to the flanged nut 6018. In some embodiments, a first mounting surface of the shuttle bracket 6020 may be coupled to the mounting surface of the flanged nut 6018. In some embodiments, the first mounting surface of the shuttle bracket 6020 may extend vertically from the flanged nut 6018 and the second mounting surface of the shuttle bracket 6020 may extend orthogonally from the first mounting surface of the shuttle bracket 6020.

The motor 6022 can be operatively coupled to the first screw 6016. In some embodiments, a coupler may couple the output shaft of the motor 6022 to an end of the first screw 6016. The output shaft of the motor 6022 can be coaxial with the first screw 6016. The first screw 6016 can be configured to be rotated with the rotation of the output shaft of the motor 6022.

The one or more end points 6024A, 6024B can be further coupled to surface of the telescoping drive table 6000. In some embodiments, the one or more end points 6024A, 6024B may couple to the base of the telescoping drive table 6000. Accordingly, the one or more end points 6024A, 6024B can provide a foundation for the first linear actuation assembly 6010.

The encoder 6026 can be coupled to the first screw 6016. In some embodiments, the encoder 6026 may be coupled to an end of the first screw 6016 opposite the motor 6022. The encoder 6026 can be configured to track the rotation of the first screw 6016 to determine the linear position of the flanged nut 6018. The tracking of the flanged nut 6018 can be used to control the position of the shuttle 6012 within the telescoping drive table 6000. In some embodiments, the tracking of the flanged nut 6018 may be used as feedback to a control system.

The one or more stoppers 6028A, 6028B can be configured to stop the flanged nut 6018 from extending beyond a predetermined point. The one or more stoppers 6028A, 6028B can be coupled to the telescoping drive table 6000. In some embodiments, the one or more stoppers 6028A, 6028B can be positioned interior relative to the end points 6024A, 6024B. Accordingly, the one or more stoppers 6028A, 6028B can prevent the flanged nut 6018 from contacting the one or more end points 6024A, 6024B.

The cable management system 6014 can be coupled to the base of the shuttle 6012. The two walls of the cable management system 6014 can extend vertically from the base of the shuttle 6012.

In some embodiments, the shuttle bracket 6020 may be operatively coupled to the base of the shuttle 6012. For example, the second mounting surface of the shuttle bracket 6020 can couple to the base of the shuttle 6012. Accordingly, the shuttle 6012 of the first linear actuator assembly 6010 can be actuated as the shuttle bracket 6020 is linearly actuated along the first screw 6016.

The first linear actuator assembly 6010 can be oriented longitudinally along the telescoping drive table 6000. In some embodiments, as shown in FIGS. 24C-24E, a portion of the first linear actuator assembly 6010 may be positioned along the base of the telescoping drive table 6000 and adjacent to a side wall of the telescoping drive table 6000.

The second linear actuator assembly 6030 can include one or more hub adapters 6032 and one or more rails 6034. The second linear actuator assembly 6030 can actuate the one or more hub adapters 6032 along the longitudinal length of the shuttle 6012. Accordingly, the second linear actuator assembly 6030 can actuate the one or more hub adapters 6032 relative to the actuation of the first linear actuator assembly 6010. Accordingly, in some embodiments, actuation of either or both of the first linear actuator assembly and the second linear actuator assembly can cause movement of the one or more hub adapters. The second linear actuator assembly 6030 can provide precise local positioning of the one or more hub adapters within the telescoping drive table 6000.

The one or more hub adapters 6032 may have any of the same or similar features and/or functions as hub adapters 4012 described above.

The one or more rails 6034 can each be a horizontally oriented beam. In some embodiments, the one or more rails 6034 may each include a groove along the top and bottom surfaces of the one or more rails 6034. The one or more rails 6034 can extend along the length of the shuttle 6012.

The second linear actuator assembly 6030 can be configured to linearly actuate the one or more hub adapters 6032. The one or more rails 6034 can be each mounted to a side wall of the shuttle 6012. In some embodiments, the one or more rails 6034 may be mounted on opposing side walls of the shuttle 6012. For example, a first rail of the one or more rails 6034 can be mounted on a first wall and a second rail of the one or more rails 6034 may be mounted on a second wall opposite the first wall. In some embodiments, the one or more rails 6034 share the same elevation along the shuttle 6012. The one or more hub adapters 6032 can be actuated to translate along the length of the one or more rails 6034. Accordingly, the one or more hub adapters 6032 can translate between a first end and a second end of the shuttle 6012. In some embodiments, the one or more hub adapters 6032 may be limited to a position between the first end and the second end of the shuttle 6012.

FIG. 24D illustrates a cross-sectional view of FIG. 24C to show additional interior components of the telescoping drive table 6000. The configuration of the interior components as shown in FIG. 24C may be the configuration of the interior components in a collapsed state. In particular, FIG. 24D illustrates the first linear actuator assembly 6010 and the one or more third linear assemblies 6036A, 6036B. In some embodiments, in the collapsed state, the first linear actuator assembly 6010 and the third linear actuator assemblies 6036A, 6036B can be contained within and/or behind the one or more telescoping members 6008A, 6008B, and shuttle 6012 (not shown). The telescoping drive table 6000 can be the same as the telescoping drive table 6000 shown and described above with respect to FIGS. 24A-24C.

The first linear actuator assembly 6010 can include the first screw 6016, the flanged nut 6018, the shuttle bracket 6020, the motor 6022, the one or more end points 6024A, 6024B, the encoder 6026, and the one or more stoppers 6028A, 6028B described above. As further shown in FIG. 24D, the first screw 6016 can rotate along its longitudinal axis to drive the flanged nut 6018 along the longitudinal length of the first screw 6016.

The one or more third linear actuator assemblies 6036A, 6036B can each include a second screw 6038A, 6038B, a flanged nut 6040A, 6040B, a bracket 6042A, 6042B, a motor 6044A, 6044B, an encoder 6046A, 6046B, and stoppers 6048A, 6048B. The one or more telescoping members 6008A, 6008B can be driven by the flanged nut 6040A, 6040B along the length of the second screw 6038A, 6038B. The bracket 6042A, 6042B can be coupled to an interior edge of one of the one or more telescoping members 6008A, 6008B.

The second screw 6038A, 6038B, the flanged nut 6040A, 6040B, the bracket 6042A, 6042B, the motor 6044A, 6044B, the encoder 6046A, 6046B, and the stoppers 6048A, 6048B can be the same as or similar to the first screw 6016, the flanged nut 6018, the shuttle bracket 6020, the motor 6022, the encoder 6026, and the stoppers 6028A, 6028B described above, respectively. In some embodiments, the second screw 6038A, 6038B may be shorter than the first screw 6016. For example, the second screw 6038A, 6038B may be half the length of the first screw 6016. In some embodiments, the second screw 6038A, 6038B can be less than half the length of the first screw 6016.

The one or more third linear actuator assemblies 6036A, 6036B can be configured to linearly actuate the one or more telescoping members 6008A, 6008B of the telescoping drive table 6000 to translate the one or more telescoping members 6008A, 600B relative to the main body 6004 of the telescoping drive table 6000. In some embodiments, the one or more third linear actuator assemblies 6036A, 6036B may include two third linear actuator assemblies 6036A, 6036B, as shown in FIG. 24D. The two third linear actuator assemblies 6036A, 6036B may mirror one another. For example, the two third linear actuator assemblies 6036A, 6036B may be operated simultaneously to actuate the corresponding flanged nuts 6040A, 6040B along the corresponding second screw 6038A, 6038B in opposite directions. In some embodiments, the two third linear actuator assemblies 6036A, 6036B may be colinear.

FIG. 24E illustrates a cross-sectional view of the telescoping drive table 6000 to show additional interior components of the telescoping drive table 6000. In particular, FIG. 24E illustrates the first linear actuator assembly 6010, the second linear actuator assembly 6030, and one of the one or more third linear actuator assemblies 6036A, 6036B. The telescoping drive table 6000 can be the same as the telescoping drive table 6000 shown and described above with respect to FIGS. 24A-24D.

As shown in FIG. 24E, the second linear actuator assembly 6030 may further include one or more linear slides 6050A, 6050B, a motor mount 6052, one or more motors 6054, a rack 6056, one or more gear trains 6058, an input gear 6060, and an output gear 6062. The one or more linear slides 6050A, 6050B, the motor mount 6052, the one or more motors 6054, the rack 6056, the one or more gear trains 6058, the input gear 6060, and the output gear 6062 can be used to actuate the second linear actuator assembly 6030. The one or more motors 6054 can be individually activated to individually control translation of the one or more hub adapters 6032 along the longitudinal length of the shuttle 6012.

The one or more linear slides 6050A, 6050B can engage with at least one of the one or more rails 6034 to guide the one or more hub adapters 6032. The one or more linear slides 6050A, 6050B may be blocks. The one or more linear slides 6050A, 6050B can include a lumen with interior protrusions. In some embodiments, the lumen may be open on one side forming a groove. In some embodiments, the geometry of the lumen may correspond to and/or match the exterior geometry of the one or more rails 6034A, 6034B. In such embodiments, the interior protrusions of the one or more linear slides 6050A, 6050B may fit within grooves of the one or more rails 6034A, 6034B. In some embodiments, the second linear actuator assembly 6030 may include the same number of linear slides 3050A, 3050B as the number of hub adapters 6032. In some embodiments, the second linear actuator assembly 6030 may include a plurality of linear slides 6050A, 6050B for each of the one or more hub adapters 6032. For example, there may be a 2:1 ratio of linear slides 6050A, 6050B to hub adapters 6032.

The motor mount 6052 can secure a distinct motor to each of the one or more hub adapters 6032. The motor mount 6052 can be a plate defining a plurality of openings. In some embodiments, the second linear actuator assembly 6030 may include the same number of motor mounts 6052 as the number of motors 6054. In some embodiments, the second linear actuator assembly 6030 can include the same number of motor mounts 6052 as the number of hub adapters 6032.

The one or more motors 6054 can provide actuation power to each of the one or more hub adapters 6032. The one or more motors 6054 can be actuated to independently control translation of the one or more hub adapters 6032. The one or more motors 6054 may have any of the same or similar features and/or functions as one or more motors 4030 described above. In some embodiments, the second linear actuator assembly 6030 may include the same number of motors 6054 as the number of hub adapters 6032.

The rack 6056 can provide structure for the one or more hub adapters 6032 to traverse along the shuttle 6012. The rack 6056 can have any of the same or similar features and/or functions as the rack 4032 described above.

The one or more gear trains 6058 can each drive a distinct hub adapter along the longitudinal length of the shuttle 6012. The one or more gear trains 6058 can each transfer an input motion from one of the one or more motors 6054 to the output gear 6062. In some embodiments, the second linear actuator assembly 6030 may include the same number of gear trains 6058 as the number of hub adapters 6032.

The input gear 6060 of the one or more gear trains 6058 can include an opening defined by an inner diameter. The opening may correspond to the outer diameter of an output shaft of a corresponding motor 6054.

The output gear 6062 of the one or more gear trains 6058 may have any of the same or similar features and/or functions as the pinion gear 4038 described above.

The one or more linear slides 6050A, 6050B can be operatively coupled to the one or more rails 6034A, 6034B. In some embodiments, the one or more linear slides 6050A, 6050B may be linearly disposed along the one or more rails 6034A, 6034B. In some embodiments, a first set of linear slides 6050A may be slidably coupled along a first rail 6034A. In some embodiments, a second set of linear slides 6050B may be slidably coupled along a second rail 6034B.

The one or more motor mounts 6052 can be coupled to corresponding linear slides 6050A, 6050B. In some embodiments, the one or more motor mounts 6052 may couple to linear slides 6050A belonging to the first set. In some embodiments, each of the one or more motor mounts 6052 may be coupled to a plurality of linear slides 6050A, 6050B. For example, each of the one or more motor mounts 6052 may be coupled to two linear slides 6050.

The one or more motors 6054 can be coupled to a corresponding motor mount 6052. In some embodiments, the output shafts of the one or more motors 6054 may extend through an opening in the corresponding motor mounts 6052. Accordingly, the one or more motors 6054 may be supported by the linear rail 6034A, 6034B.

The rack 6056 can be coupled to a side wall of the shuttle 6012. In some embodiments, the rack 6056 may be mounted to the first side wall of the shuttle 6012 at a position below the rail 6034A. Accordingly, motion along the rack 6056 may be relative to the shuttle 6012.

The one or more gear trains 6058 can be operatively coupled to the output shafts of a corresponding motor 6054 and the rack 6056. In some embodiments, the input gear 6060 may be operatively coupled to the output shaft of the corresponding motor 6054 and the output gear 6062 may be operatively coupled to the rack 6056. In some embodiments, the output gear 6062 may be bonded to the input gear 6060. Thus, the one or more gear trains 6058 may transfer an output motion of the corresponding motor 6054 to a motion along the rack 6056. The corresponding motion may be relative to the shuttle 6012.

The one or more hub adapters 6032 can be coupled to a corresponding motor mount 6052. In some embodiments, the base of the one or more hub adapters 6032 may be operatively coupled to the corresponding motor mount 6052. Additionally and/or alternatively, the one or more hub adapters 6032 may be further coupled to the second set of linear slides 6050B. Accordingly, the hub adapters 6032 may be supported by all of the one or more rails 6034A, 6034B.

The second linear actuator assembly 6030 can provide motion within the shuttle 6012. The shuttle 6012 of the first linear actuator assembly can extend through the main body 6004 and the one or more telescoping members 6008 of the telescoping drive table 6000. Accordingly, the second linear actuator assembly 6030 may be supported by the one or more rails 6034A, 6034B and configured to be linearly displaced along the length of the rails 6034A, 6034B via actuation of the one or more motors 6045. As described above, in some embodiments, the one or more hub adapters 6032 may be actuated independently.

The one or more third linear actuator assemblies 6036A, 6036B can further include a plurality of rails 6064 and plurality of linear slides 6066. The plurality of rails 6064 and the plurality of linear slides 6066 can be used for driving the one or more telescoping members 6008A, 6008B laterally between a collapsed state and a deployed state.

The plurality of rails 6064 can provide structural support for the one or more telescoping members 6008A, 6008B as the one or more telescoping members 6008A, 6008B transition between the collapsed state and the deployed state. Additionally, the plurality of rails 6064 can provide a guide or path for the one or more telescoping members 6008A, 6008B to traverse. The plurality of rails 6064 may be the same or substantially similar to the rails 6034A, 6034B described above. The plurality of rails 6064 can be horizontally oriented. In some embodiments, the plurality of rails 6064 may extend along the longitudinal axis of the telescoping drive table. In some embodiments, the plurality of rails 6064 may be mounted to the main body 6004. In some embodiments, the plurality of rails 6064 extend between the first end of the main body 6004 and the second end of the main body 6004. In some embodiments, the plurality of rails 6064 can be positioned on a front wall and a rear wall of the main body 6004. In some embodiments, the front wall and the rear wall may include one or more rails 6064.

The plurality of linear slides 6066 can couple the one or more telescoping members 6008A, 6008B to the plurality of rails 6064. The plurality of linear slides 6066 may the same as or substantially similar to the linear slides 6050A, 6050B described above. The plurality of linear slides 6066 may be coupled on one side to at least one of the one or more telescoping members 6008A, 6008B. The plurality of slides 6066 may be coupled on another side to at least one of the plurality of rails. In some embodiments, each of the one or more telescoping members 6008A, 6008B may be operatively coupled to a plurality of rails 6064 via the plurality of linear slides 6066.

The one or more third linear actuator assemblies 6036A, 6036B may be operatively coupled to the one or more telescoping members 6008A, 6008B of the telescoping drive table 6000. In some embodiments, the brackets 6042A, 6042B may be operatively coupled to the base of a corresponding telescoping member 6008A, 6008B. Accordingly, the one or more telescoping members 6008A, 6008B can actuated as a corresponding bracket 6042A, 6042B is linearly actuated along the corresponding second screw 6038A, 6038B.

The first linear actuator assembly 6010, the second linear actuator assembly 6030, and the one or more third linear actuator assemblies 6036A, 6036B may be oriented longitudinally along the telescoping drive table 6000. In some embodiments, as shown in FIGS. 24C-24E, the one or more third linear actuator assemblies 6036A, 6036B may be positioned along the base of the telescoping drive table 6000 and adjacent to a side wall of the telescoping drive table 6000 opposite the first linear actuator assembly. Additionally, the one or more third linear actuator assemblies 6036A, 6036B may be positioned below the first and second linear actuator assemblies 6010, 6030.

Figure 24F:
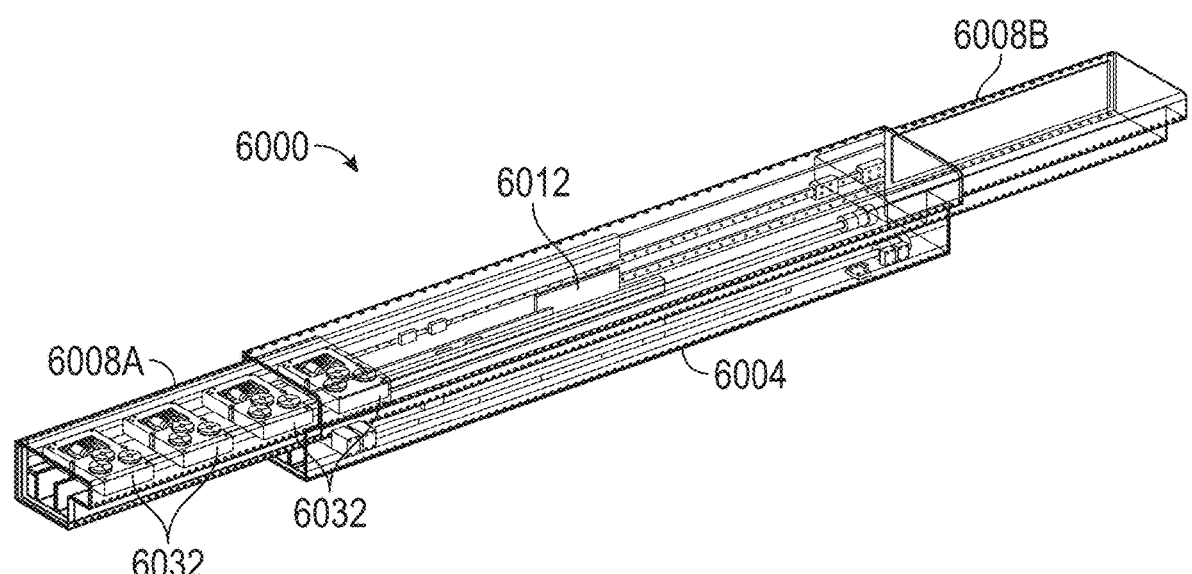
FIG. 24F illustrates a front perspective view of a telescoping drive table in a deployed position.
Figure 24G:
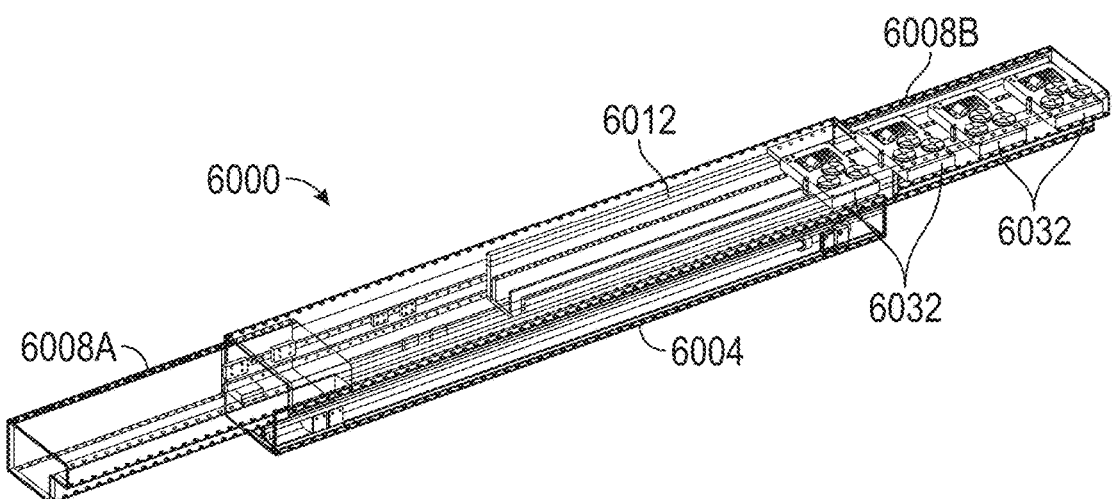
FIG. 24G illustrates a front perspective view of a telescoping drive table in a deployed position.

FIGS. 24F-24G illustrate the telescoping drive table 6000 in a deployed configuration in which the telescoping members 6008A and 6008B are extended out of the main body 6004. The one or more hub adapters 6032 can include a first hub adapter 6032A, a second hub adapter 6032B, a third hub adapter 6032C, and a fourth hub adapter 6032D. The one or more hub adapters 6032 can be sequentially placed along the shuttle 6012. In some embodiments, the first hub adapter 6032A can be positioned at a distal end of the shuttle 6012 and the fourth hub adapter 6032D can be positioned at a proximal end, or vice versa.

As described herein, the shuttle 6012 can move axially along the length of the telescoping drive table 6000 (e.g., by the first linear actuator assembly 6010). The shuttle 6012 can translate between the ends of the one or more telescoping members 6008A, 6008B. As shown in FIG. 24F, the shuttle 6012 can translate to be positioned at least partially in the first telescoping member 6008A. As shown in FIG. 24G, the shuttle 6012 can translated to be positioned at least partially in the second telescoping member 6008B.

In some embodiments, the length of the shuttle 6012 may be limited to the length of the main body 6004. The shuttle 6012 may be configured to extend along a full length of the telescoping drive table 6000 when one or more the telescoping members 6008A and 6008B are fully extended (e.g., the combined length of the main body 6004 and one or more of the telescoping members 6008A, 6008B).

In some embodiments, the shuttle 6012 can be translated within the main body 6004 and/or one or more telescoping members 6008A and 6008B to advantageously provide a full range of motion for the one or more hub adapters 6032 along the combined length of the main body 6004 and the one or more telescoping members 6008A, 6008B. In some embodiments, the shuttle 6012 can position the hub adapters 6032 in a general position.

As described above, the one or more hub adapters 6032 can translate along the length of the shuttle 6012 (e.g., by the second linear actuator assembly 6030). In some embodiments, each of the one or more hub adapters 6032 can translate along the shuttle 6012 to local position. Accordingly, each of the one or more hub adapters 6032 can be precisely positioned within the general position provided by the shuttle 6012. As shown in FIG. 24F, at least some of the hub adapters 6032 are positioned within the telescoping member 6008A at positions distal to a distal end of the main body 6004. As shown in FIG. 24G, at least some of the hub adapters 6032 are positioned within the telescoping member 6008B at positions proximal to a proximal end of the main body 6004.

The shuttle 6012 may function similar to the drive table 4002, described above. In some embodiments, the shuttle 6012 may move to a general position along the length of the telescoping drive table 6000 before the one or more hub adapters 6032 move to a local position along the length of the shuttle 6012. Additionally and/or alternatively, the one or more hub adapters 6032 can move relative to the shuttle 6012 simultaneously with the shuttle 6012, as the shuttle 6032 translates along the length of the telescoping drive table 6000. In some embodiments, the shuttle 6012 can move to adjust an axial position of at least one of the hub adapters 6032 to a desired axial position (for example, to adjust the position of a coupled interventional device to a desired axial position), either while the at least one of the hub adapters 6032 is maintained at a fixed position along the shuttle 6012 or while the at least one of the hub adapters 6032 moves along the shuttle 6012. Additionally and/or alternatively, the one or more hub adapters 6032 can move relative to the shuttle 6012 before the shuttle 6012 translates along the length of the telescoping drive table 6000.

In certain embodiments, the telescoping drive table 6000 can be configured to maintain at least one of the one or more hub adapters 6032 in a fixed position relative to a reference point when the shuttle 6012 is moved in a first axial direction relative to the reference point by moving the at least one of the one or more hub adapters 6032 in a second axial direction relative to the shuttle 6012 that is opposite to the first axial direction as the shuttle 6012 is moved in the first axial direction. The reference point can be a position along the main body 6004 and/or a designated location on the patient (e.g., a femoral access point). Similarly, the telescoping drive table 6000 can be configured to maintain additional hub adapters 6032 in a fixed position relative to a reference point when the shuttle 6012 is moved. For example, as the shuttle 6012 is moved, such as to move the first hub adapter 6032A (and corresponding interventional device), the position of the second hub adapter 6032B (and corresponding interventional device) relative to a reference point can be maintained or fixed by moving the second hub adapter 6032B along the shuttle 6012 by an equal magnitude or speed as compared to a movement of the shuttle 6012 in an opposite direction (e.g., if movement of the shuttle 6012 is not intended to cause axial movement of the interventional device coupled to the hub adapter 6032B). The third hub adapter 6032C and/or the fourth hub adapter 6032D (and/or any other additional hub adapters) can similarly be maintained in a fixed position relative to a patient reference point when the shuttle 6012 is moved relative to the reference point (e.g., if movement of the shuttle 6012 is not intended to cause axial movement of the interventional devices coupled to the hub adapters 6032C and/or 6032D).

In some embodiments, in response to user operation of controls to move the one or more hub adapters 6032, the telescoping drive table 6000 can cause the one or more hub adapters 6032 to adjust their positions relative to one another to correspond to the positions they would be in if each of the one or more hub adapters 6032 were independently movable along an entirety of the length of the telescoping drive table 6000 in the absence of a shuttle 6012. For example, in response to a user control operation (e.g., manipulation of a first control) to move the interventional device coupled to the first hub adapter 6032A in a distal direction by moving the shuttle 6012 in the distal direction, the telescoping drive table 6000 can adjust the positions of the remaining hub adapters 6032 (e.g., the second hub adapter 6032B, the third hub adapter 6032C, and/or the fourth hub adapter 6032D) so that they move along the shuttle 6012 in the in the proximal direction by an equal magnitude or speed.

In response to control operations to axially move the first hub adapter 6032A (via movement of the shuttle 6012) and also axially move one or more of the other hub adapters 6032, the telescoping drive table 6000 can move the other hub adapters 6032 to the same position relative to a reference point or relative to the first hub adapter 6032A that they would be moved to in the absence of movement of the shuttle 6012. For example, if a user performs a control operation to move the first hub adapter 6032A and the second hub adapter 6032B distally by 5 mm, the telescoping drive table 6000 may move the shuttle 6012 distally by 5 mm without moving the second hub adapter 6032B relative to the shuttle 6012. If a user performs a control operation to move the first hub adapter 6032A distally by 5 mm and the second hub adapter 6032B distally by 6 mm, the telescoping drive table 6000 may move the shuttle 6012 distally by 5 mm and move the second hub adapter 6032B distally along the shuttle 6012 by 1 mm so that the second hub adapter 6032B has moved a total of 6 mm distally relative to the reference point. Alternatively, the telescoping drive table 6000 may move the shuttle 6012 by 4 mm, move the first hub adapter 6032A by 1 mm and the second hub adapter 6032B by 2 mm, or any other suitable combination of shuttle 6012 movement and hub adapter movement to translate the hub adapters 6032A and 6032B to the appropriate positions.

In certain embodiments, the telescoping drive table 6000 can be configured to adjust the positions of the hub adapters 6032 along the shuttle 6012 to maintain desired relative positions of interventional devices coupled to the hub adapters 6032 while the shuttle 6012 translates axially. For example, if the shuttle 6012 is translated in a first direction to cause a desired axial translation of an interventional device coupled to the hub adapter 6032A in the first direction relative to the interventional devices coupled to the hub adapters 6032B-D, the hub adapters 6032B-D may translate along the shuttle 6012 in a second direction opposite of the first direction to maintain the desired relative positioning of the interventional devices coupled to the hub adapters 6032B-D relative to the interventional device coupled to the hub adapter 6032A.

In certain embodiments, movement of two or more interventional devices, two or more hubs, and/or two or more hub adapters may be linked when controlled movements of one or more of the interventional devices, hubs, and/or hub adapters would result in relative positions between the interventional devices, interventional device hubs, and/or hub adapters at distances greater than a total available separation distance (e.g., due to the length of the drive surface of the drive table or due to a length of a shuttle along which hub adapters translate).

In some embodiments, linked interventional devices, hubs, and/or hub adapters can include a primary device, hub, and/or hub adapter and one or more secondary devices, hubs, and/or hub adapters. Movement of the primary device, hub, and/or hub adapter can cause movement of the secondary device, hub, and/or hub adapter in the same direction by the same magnitude and/or velocity. Movement of a control to move the secondary device, hub, and/or hub adapter, but not the primary device, hub, and/or hub adapter may not cause the primary device to move. In some embodiments, movement of a control to move the secondary device, hub, and/or hub adapter, but not the primary device, hub and/or hub adapter, in a direction that would increase a separation distance between the primary device, hub, and/or hub adapter and the secondary device, hub, and/or hub adapter may result in no movement of either the primary device, hub, and/or hub adapter or the secondary device, hub, and/or hub adapter. In some embodiments, movement of a control to move the secondary device, hub, and/or hub adapter, but not the primary device, hub, and/or hub adapter, in a direction that would decrease the separation distance between the primary device, hub, and/or hub adapter and the secondary device, hub, and/or hub adapter may cause the secondary device to move without movement of the primary device, hub, and/or hub adapter and/or may unlink the secondary device, hub, and/or hub adapter from the primary device, hub, and/or hub adapter.

During some procedures, a user may perform a control operation intended to cause the distal most interventional device (e.g., a guide catheter) coupled with the first hub adapter 6032A to move distally relative to the proximal most interventional device (e.g., a guidewire) (e.g., coupled to the fourth hub adapter 6032D) by a distance that would result in a distance between the first hub adapter 6032A and the fourth hub adapter 6032D greater than the total length of the shuttle 6012. As described above, if a user performs a control operation to move the shuttle 6012 and the first hub adapter 6032A distally, the telescoping drive table 6000 may adjust the position of the fourth hub adapter 6032D by moving the fourth hub adapter 6032D in the proximal direction, preferably by an equal magnitude or speed. In some procedures, the shuttle 6012 may be able to move in a distal direction by a greater magnitude than the fourth hub adapter 6032D can move proximally. In other words, while adjusting in response to movement of the shuttle 6012, the fourth hub adapter 6032D may reach a proximal most position along the shuttle 6012 and be prevented from further movement while the shuttle 6012 continues to move in the distal direction. In response, the telescoping drive table 6000 may compensate by temporarily linking the movement of the fourth hub adapter 6032D with the movement of the first hub adapter 6032A so that the fourth hub adapter 6032D moves in unison with the first hub adapter 6032A.

For example, when linked, if the first hub adapter 6032A is moved distally by way of the shuttle 6012 moving distally, the fourth hub adapter 6032D can move distally by the same magnitude and/or at the same speed. In this situation, the fourth hub adapter 6032D can move distally by the same magnitude and/or at the same speed as the first hub adapter 6032A by maintaining its position on the shuttle 6012 while the shuttle 6012 moves distally. Similarly, if the first hub adapter 6032A is moved proximally by way of the shuttle 6012 moving proximally, the fourth hub adapter 6032D can move proximally by the same magnitude and/or at the same speed. In this situation, the fourth hub adapter 6032D can move proximally by the same magnitude and/or at the same speed as the first hub adapter 6032A by maintaining its position on the shuttle 6012 while the shuttle 6012 moves proximally.

In some embodiments, the fourth hub adapter 6032D can be unlinked from the first hub adapter 6032A (e.g., such that it adjusts in response to movements of the first hub adapter 6032A) in response to user manipulation of a control for the fourth hub adapter 6032D causing it to move independently or in response to another user input. In certain embodiments, while the first hub adapter 6032A and fourth hub adapter 6032D are linked, the telescoping drive table 6000 can track the desired relative position of the fourth hub adapter 6032D relative to the first hub adapter 6032A and/or relative to a reference point and adjust the fourth hub adapter 6032D to the desired position once sufficient space is available along the shuttle 6012.

Linking of the distal most hub adapter (e.g., the first hub adapter 6032A) and the proximal most hub adapter (e.g., the fourth hub adapter 6032D) may allow for a shorter shuttle 6012. As an example, in certain embodiments, a length of the shuttle 6012 may be about 130 cm long. A distal most interventional device (e.g., a guide catheter) may have a length of about 127 cm. A length of a section of the distal most interventional device that overlaps the drive shuttle 6012 (e.g., when coupled to a hub coupled to the distal most hub adapter (e.g., the first hub adapter 6032A)) may be about 3 cm. A proximal most interventional device (e.g., a guidewire) can have a length of about 265 cm. A section of the proximal most interventional device may extend proximally from a proximal end of a proximal most hub coupled to a proximal most hub adapter (e.g., the fourth hub adapter 6032D) in some embodiments. For example, in certain embodiments, the section of the proximal most interventional device may extend between about 2 cm and about 20 cm, between about 5 cm and about 15 cm, or about 10 cm from the proximal end of the proximal most hub. In some embodiments, the proximal most hub may extend proximally from a proximal end of the shuttle 6012 by about 2.5 cm in its proximal most position. In certain embodiments, a proximal most end of the proximal most interventional device may be positioned proximally from a proximal end of the shuttle 6012 by a distance of between about 4.5 cm and about 22.5 cm, between about 7.5 cm and about 17.5 cm, or about 12.5 cm, when the proximal most hub adapter is in its proximal most position. In an initial configuration a distal most end of the proximal most interventional device may be proximal to a distal most end of the distal most interventional device.

While linking of hub adapters is described herein, one of skill in the art would understand that the corresponding hubs and/or corresponding interventional devices may also be linked. As described herein with respect to the hub adapters, linked hubs and/or linked interventional devices may move in the same direction by the same magnitude and/or speed.

While discussed with respect to the shuttle 6012, linking of hub adapters and/or hubs (e.g., linking of a proximal most hub adapter and a distal most hub adapter and/or linking of a proximal most hub and distal most hub) of the drive table may be performed with any of the embodiments of shuttle 6012 described herein.

As described herein, the telescoping drive table 6000 can be configured such that each of the hub adapters 6032A-D is independently controllable and movable relative to the other hub adapters. For example and without limitation, each of the hub adapters 6032 on the shuttle 6012 can have an independently controllable motor 6054 or other actuator configured to independently move the hub adapter 6032 relative to the shuttle 6012.

Alternatively, in some embodiments, the position of one of the hub adapters (e.g., the first hub adapter 6032A) can be fixed relative to the shuttle 6012. For example, in an embodiment having a first hub adapter 6032A, a second hub adapter 6032B, a third hub adapter 6032C, and a fourth hub adapter 6032D, the first hub adapter 6032A can be fixed to the shuttle 6012 and the second hub adapter 6032B, the third hub adapter 6032C, and the fourth hub adapter 6032D can each have an independently controllable motor 6054 or actuator configured to independently move the second hub adapter 6032B, the third hub adapter 6032C, and the fourth hub adapter 6032D relative to the shuttle 6012 and the first hub adapter 6032A.

As mentioned, in some embodiments, one or more of the first hub adapter 6032A, the second hub adapter 6032B, third hub adapter 6032C, and fourth hub adapter 6032D can each be configured to move in the axial direction relative to the shuttle 6012 in response to an input provided by a user of the telescoping drive table 6000.

In some embodiments, one or more of the first hub adapter 6032A, the second hub adapter 6032B, the third hub adapter 6032C, and the fourth hub adapter 6032D can be configured to move in the axial direction relative to the shuttle 6012 via a linear actuator (e.g., a rack and pinion linear actuator) in response to an input provided by a user of the telescoping drive table 6000. The rack and pinion arrangement can have a rack 6056 (or straight gear) and a pinion gear (e.g., output gear 6062) coupled to a shaft of the motor 6054. For example and without limitations, the second hub adapter 6032B can have a motor 6054B and an output gear 6062B that can engage the rack 6056. The third hub adapter 6032C can have a motor 6054C and an output gear 6062C that can also engage the rack 6056. Similarly, the fourth hub adapter 6032D can have a motor 6054D and an output gear 6062D that can also engage the rack 6056. Each hub adapter 6032 can have its own unique motor 6054 and output gear 6062 to allow for independent movement of each hub adapter 6032.

In certain embodiments, the drive table 6000 may be configured to cause the shuttle 6012 to move in particular situations instead of or in addition to moving one or more of the hub adapters 6032A-D. For example, movement of the shuttle 6012 and the hub adapters 6032A-D may be controlled by a control system (e.g., operating using one or more algorithms to control movement of the shuttle 6012 and the hub adapters 6032A-D). For example, in certain embodiments, the shuttle 6012 may be configured to move distally when the distal most hub adapter 6032A reaches a distal most position along the shuttle 6012 and further distal movement of the hub adapter 6032A is instructed (e.g., to cause further distal movement of the interventional device coupled to the hub adapter 6032A). In some embodiments, the shuttle 6012 may be configured to move proximally when the proximal most hub adapter 6032D reaches a proximal most position along the shuttle 6012 and further proximal movement of the hub adapter 6032D is instructed (e.g., to cause further proximal movement of the interventional device coupled to the hub adapter 6032D). In some embodiments, as described herein, the shuttle 6012 may not move proximally in response to the proximal most hub adapter 6032D reaching the proximal most position along the shuttle 6012 when further proximal movement of the hub adapter 6032D is instructed if such proximal movement of the shuttle 6012 would cause an undesired proximal movement of the distal most hub adapter 6032A (e.g., if the distal most hub adapter 6032A is at the distal most position along the shuttle 6012). Instead, the proximal most hub adapter 6032D may be temporarily linked with the distal most hub adapter 6032A as described herein.

In some embodiments, the shuttle 6012 may configured to move in a particular direction in response to an instruction (e.g., a control signal) instructing a plurality or a majority of the hub adapters 6032A-D coupled to the shuttle 6012 to move in the particular direction.

In certain embodiments, as shown in FIGS. 24F-24G, a top surface of the one or more telescoping members 6008A, 6008B can be vertically offset from a top surface of the main body 6004. A sterile barrier can extend from the top surface of the main body 6004 to the ends of the one or more telescoping members 6008A, 6008B. The sterile barrier may form the support surface 6006.

In some embodiments, the sterile barrier may provide a transition between the one or more telescoping members 6008A, 6008B and the main body 6004 to provide a continuous surface for one or more hubs magnetically coupled to the hub adapters to translate along. The sterile barrier can prevent the one or more driven hubs from being stuck on the one or more telescoping members 6008A, 6008B or being dislodged or displaced. In some embodiments, ends of the sterile barrier may be coupled respective ends of the telescoping members 6008A, 6008B. In such embodiments, the sterile barrier may be extended as the telescoping members 6008A, 6008B are deployed. In some embodiments, the sterile barrier may be coupled to the ends of the telescoping members 6008A, 6008B via adhesive strips, double sided tape, magnets, and/or other fastening means. The sterile barrier can be retractable.

Figure 24H:
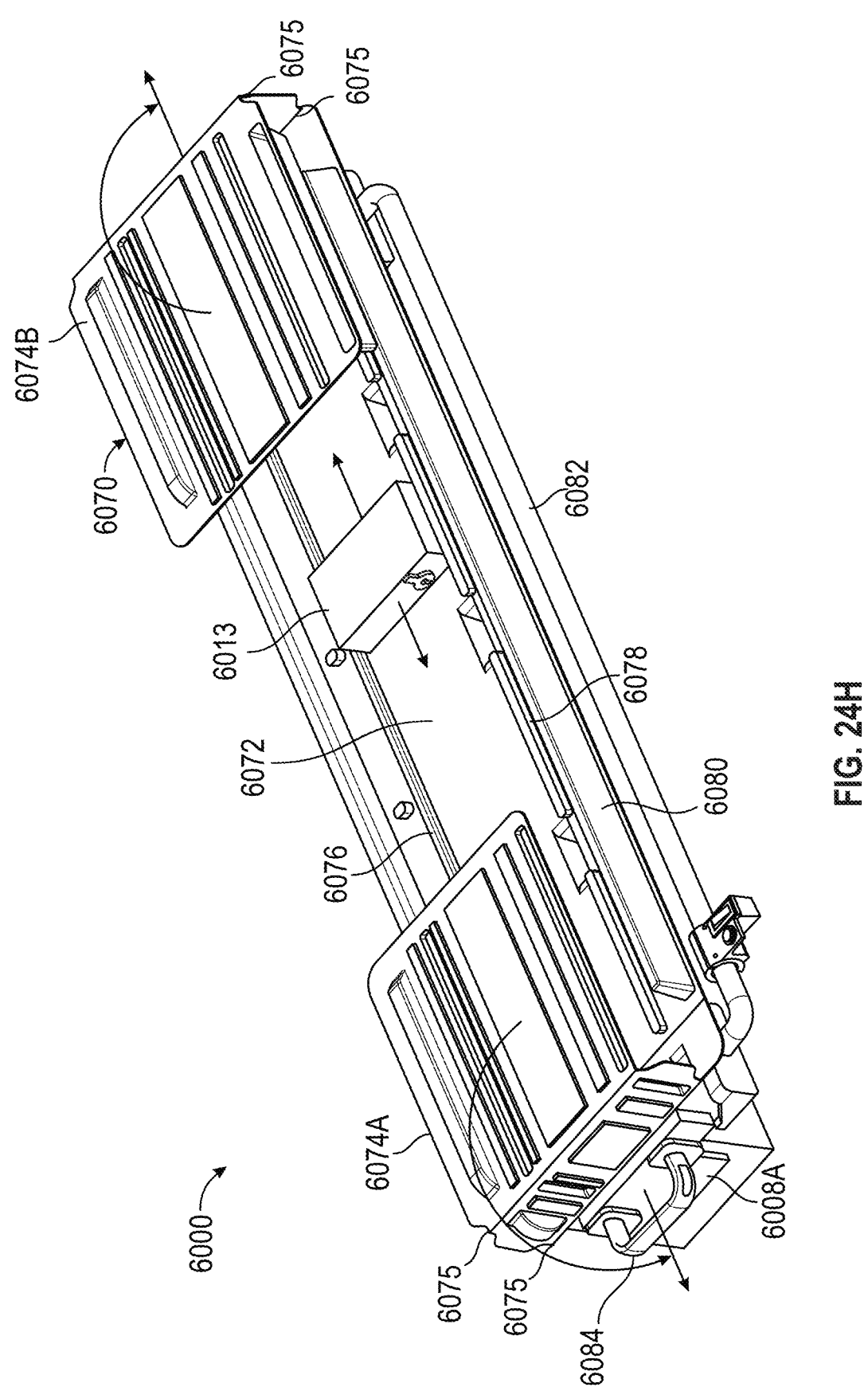
FIG. 24H illustrates a front perspective view of a telescoping drive table with a deployable sterile barrier.

FIG. 24H illustrates an embodiment of a deployable sterile barrier 6070 for a telescoping drive table 6000. The deployable sterile barrier 6070 can include a main section 6072, one or more deployable sections 6074A, 6074B, an upper guide 6076, a lower guide 6078, and a collection wall or gutter wall 6080.

The main section 6072 of the deployable sterile barrier 6070 can extend along the length of the main body 6004 of the telescoping drive table 6000. In some embodiments, the main section 6072 can have a static length. For example, the main section 6072 can have a constant length L1 corresponding to the length of the main body 6004.

The one or more deployable sections 6074A, 6074B of the deployable sterile barrier 6070 can extend distally and proximally, respectively, from the ends of the main section 6072. The one or more deployable sections 6074A, 6074B can have static length. For example, the one or more deployable sections 6074A, 6074B can have a constant length L2, L3 corresponding to the lengths of the one or more telescoping members 6008A, 6008B, respectfully. In some embodiments, the one or more deployable sections 6074A, 6074B may extend from a collapsed state to a deployed state. In the collapsed state, the one or more deployable sections 6074A, 6074B may fold above the main section 6072. For example, the deployable sections 6074A, 6074B can fold about hinges 6075. In the deployed state the one or more deployable sections 6074A, 6074B can unfold (e.g., about hinges 6075) and extend linearly from the ends of the main section 6072.

In some embodiments, the one or more deployable sections 6074A, 6074B may deploy when the one or more telescoping members 6008A, 6008B are in a deployed position such that the one or more deployable sections 6074A, 6074B can extend along a corresponding one of the one or more telescoping members 6008A, 6008B. In the deployed state, the one or more deployable sections 6074A, 6074B may advantageously provide a continuous surface along which one or more driven hubs 6013 can translate. Accordingly, a difference in planar surfaces between the upper surfaces of the one or more telescoping members 6008A, 6008B and the main body 6004 may not prevent the one or more driven hubs 6013 from translating from one end of the telescoping table 6000 to the other in the deployed state.

The upper guide 6076 can be a linear protrusion along the length of the deployable sterile barrier 6070. The upper guide 6076 can be configured to prevent the one or more driven hubs 6013 from rotating or otherwise being unintentionally displaced along the deployable sterile barrier 6070.

The lower guide 6078 can similarly be a linear protrusion extending along the length of the deployable sterile barrier 6070. The lower guide 6078 can be configured to prevent one or more driven hubs 6013 from rotating or otherwise being unintentionally displaced along the deployable sterile barrier 6070. In some embodiments, the upper guide 6076 and the lower guide 6078 can be implemented to define a channel along which the one or more driven hubs 6013 can be driven by a corresponding hub adapter 6032. In other embodiments, a channel may be recessed within the sterile barrier 6070 and/or within the drive table 6000 beneath the sterile barrier 6072.

The gutter wall 6080 can be a linear protrusion extending along the length of the deployable sterile barrier 6070. The gutter wall 6080 can be configured to support interventional devices. In some embodiments, one or more interventional devices may be disconnected from one or more driven hubs. The collection wall 6080 may be configured to support the one or more interventional devices in an inactive state.

The deployable sterile barrier 6070 can be positioned between the upper surface of the drive table 6000 and the one or more driven hubs 6013. Furthermore, the deployable sterile barrier 6070 can be positioned between the one or more hub adapters 6032 and the corresponding one or more driven hubs 6013.

The main section 6072 of the deployable sterile barrier 6070 can be secured to the main body 6004 of the deployable sterile barrier. In some embodiments, the main section 6072 may be fixedly secured to the main body 6004. For example, the main section 6072 can be fixedly secured to the main body 6004 via bonding and/or adhesives (e.g., doubled-sided adhesive tape). Additionally and/or alternatively, the deployable sterile barrier 6070 can be removably secured to the main body 6004 via mechanical fasteners. For example, the main section 6072 can be removably secured to the main body 6004 via magnetic coupling, nuts and bolts, hook and loop fasteners and/or sliding the deployable sterile barrier 6070 into a mating surface of the main section 6072.

As further illustrated in FIG. 24H, the telescoping drive table 6000 may include a first rail 6082 and a second rail 6084. The first rail 6082 can extend along the length of the main body 6004 and the second rail 6082 can extend along the width of the one or more telescoping members 6008A, 6008B. In some embodiments, the first rail 6082 and second rail 6084 can each provide grip surfaces for interacting with the telescoping drive table 6000. In some embodiments, one or both of the first rail 6082 and the second rail 6084 can gripped by a user and manipulated to move the drive table 6000 superiorly, inferiorly, proximally, distally, and/or laterally. For example, in some embodiments, the rail 6082 may be used for vertical movement (e.g., superior and inferior movement). In some embodiments, the second rail 6084 may be used for horizontal movement in a proximal or distal direction. In some embodiments, the rail 6082 may be used for horizontal movement laterally relative to a longitudinal axis (e.g., a proximal to distal axis) of the drive table 6000.

Angled Drive Table:

FIGS. 25-29 illustrate embodiments of an angled drive table 7000 including an angled support surface for supporting one or more hubs.

Figure 25:
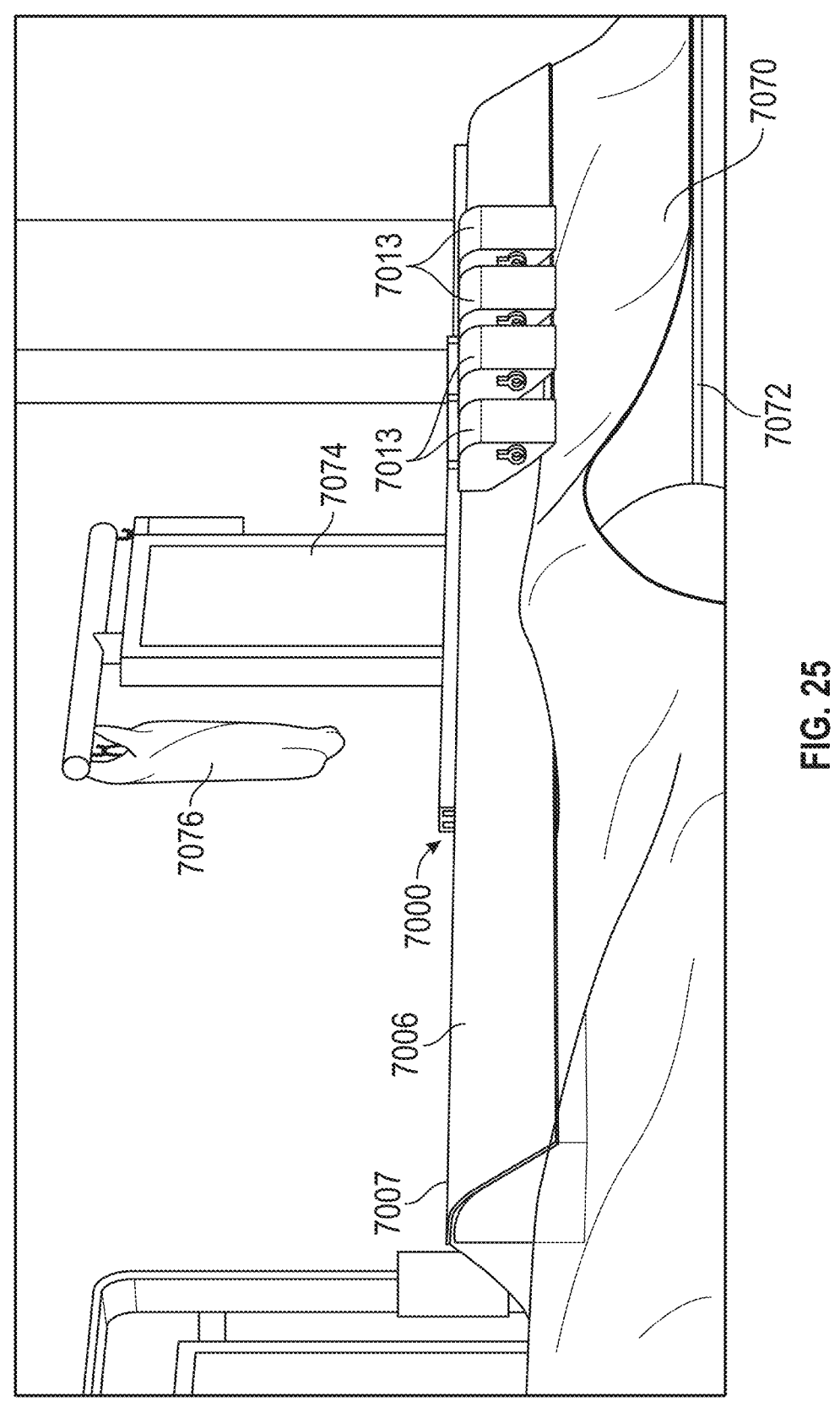
FIG. 25 illustrates an angled drive table in an operating room.

FIG. 25 illustrates an angled drive table 7000 set-up in an operating room with a sterile barrier 7070 and an operating table 7072. As shown in FIG. 25, a robotic surgical system may further include a monitor 7074 and fluids 7076.

The angled drive table 7000 can include an angled support surface 7006 for supporting one or more hubs 7013. The angled support surface 7006 may further include a superior surface 7007.

The angled drive table 7000 can provide a support for driving interventional devices and access systems relative to a patient as described herein. The angled drive table 7000 may include any of the same or similar features and/or functions as any of the drive tables described. For example, the angled drive table 7000 may include any of the same or similar features and/or functions as the drive support table 20 or telescoping drive table 6000 described above. For example, the angled drive table 7000 may include one or more telescoping members, such as telescoping members 6008 as described with respect to the drive table 6000.

The drive table 7000 may include an elongated frame extending between a proximal end and a distal end. At least one support table support may be provided to stabilize the drive table 7000 with respect to the patient (not illustrated). The support may further include one or more legs or preferably an articulating arm configured to allow movement and positioning of the frame over or adjacent to the patient. In some embodiments, the angled drive table 7000 may include any of the same or similar features and/or functions as any of the drive tables described herein with an angled top surface.

In some embodiments, the angled support surface 7006 may include any of the same or similar features and/or functions as the support surface 104 or support surface 6006 described above. The angled support surface 7006 can be configured for supporting the one or more hubs 7013. The one or more hubs 7013 may include any of the same and/or similar features as any of the hubs described herein. For example, in certain embodiments, the one or more hubs 7013 can include a guide catheter hub, a procedure catheter hub, an access catheter hub, and/or a guidewire hub.

In some embodiments, the angled support surface 7006 can be a substantially planar surface. The angled support surface 7006 may be defined by one or more segments. In some embodiments, the angled support surface 7006 may be a single body spanning the length of the angled drive table 7000. In some embodiments, the angled support surface 7006 may be formed by a plurality of telescoping portions. The angled surface 7006 may be oriented along an X-Y-Z plane as described in greater detail below.

The superior surface 7007 can be a horizontally oriented planar surface. The superior surface 7007 may be configured to form at least a portion of the external shell of the angled drive table 7000. In some embodiments, the superior surface

7007 may be part of the angled support surface 7006. In some embodiments, the superior surface 7007 may be coplanar with the support surface 7006 described above.

As described herein, the one or more hubs 7013 may each be coupled to an interventional device, such as a guide catheter, a procedure catheter, an access catheter, and a guide catheter. In certain embodiments, one or more of the hubs 7013 may be configured for providing saline, contrast, and/or aspiration to a patient.

The sterile barrier 7070 may be any draping or other material configured to provide a sterile barrier between the internal, re-useable components of the drive table 7000 and the external, disposable components of the drive table exposed to potential contagions, pathogens, and/or other biomaterials within the operating room. In some embodiments, the sterile barrier 7070 may have any of the same or similar features and/or functions as the sterile barrier 32, sterile barrier 232, or sterile barrier 1632 described above.

The operating table 7072 can be configured to support a patient. The operating table 7072 may be any operating table suitable for supporting a patient during an operation. As shown in FIG. 25, the operating table 7072 may include a substantially horizontal surface.

The monitor 7074 may provide imaging of the patient or the progress of interventional devices within the patient.

The fluids 7076 may be any fluid to be administered to a patient. In some embodiments the fluids 7076 may be saline and/or contrast.

As shown in FIG. 25, the angled support surface 7006 can be positioned above and form at least a portion of the upper surface of the angled drive table 7000. The angled support surface 7006 can support the one or more hubs 7013.

As shown in FIG. 25, the superior surface 7007 may be positioned above and form at least a portion of the upper surface of the angled drive table 7000. The superior surface 7007 can be oriented along the upper most surface of the angled drive table 7000. The superior surface 7007 can extend from the angled support surface 7006 defining a curve between the angled portion and the horizontal portion of the angled support surface 7006. In some embodiments, the drive table 7000 may not include a horizontally oriented planar surface.

As shown in FIG. 25, the one or more hubs 7013 can be supported by the angled support surface 7006 of the angled drive table 7000 and translate along the length of the angled support surface 7006.

The operating table 7072 may be positioned adjacent to the angled drive table 7000. In some embodiments, the angled drive table 7000 is physically coupled to the operating table 7072. In some embodiments, the angled drive table 7000 may be coupled to and/or moved by an arm (e.g., arm 4006), which may be coupled to a base structure (e.g., base structure 4004) or the operating table 7072.

The monitor 7074 may be positioned adjacent to the angled drive table 7000. In some embodiments, the monitor 7074 may be electrically connected to the angled drive table 7000.

As shown in FIG. 25, the fluids 7076 can be coupled to a support structure. The fluids 7076 may be in fluid communication with the angled drive table 7000.

The angled drive table 7000 may advantageously allow for a reduction in the dead length of interventional devices, extending between the one or more hubs 7013 to a patient laying on the operating table 7072. Interventional devices extending from hubs coupled to a drive table may have a dead length spanning between the patient and the hub including the height of the hubs relative to an access point into the anatomy (e.g., a femoral access point). For example, drive tables without an angled support surface (e.g., the embodiment of the drive support table 20 shown in FIG. 1 and described above) may drive one or more hubs 7013 along a flat or horizontal surface (e.g., a planar surface parallel with the floor or parallel with the operating table) of the drive support table. Such a horizontal surface may need to be positioned to accommodate the anatomy of the patient (e.g., raised above the anatomy of the patient, such as the patient's feet). In such embodiments, dead length spanning between the patient and the hub can including the height of the horizontal surface of the drive table above the access point. In contrast, an angled drive table may allow for a lower height of a hub relative to the access point, thereby providing a smaller dead length in comparison to a drive table having a horizontal support surface. For example, the angled support surface 7006 is sloped thereby providing a range of possible heights from which an interventional device may extend. In some embodiments, the possible heights can range from an inferior edge of the angled support surface 7006 to a superior edge of the angled support surface 7006. In other embodiments, as described in further detail herein, a hub may extend from the inferior edge of the support surface 7006 so that the height of the hub at the portion from which an interventional device extends is positioned inferior to the inferior edge of the support surface 7006. Similarly, in some embodiments, the hub may extend above a superior edge of the angled support surface 7006. In some embodiments, the hub may be positioned at heights ranging from the base of the angled drive table 7000 to the superior surface 7007 of the angled drive table 7000.

Additionally, the angled drive table 7000 may advantageously provide a better approach angle for an interventional device to engage with a patient (e.g., enter an access point). For example, interventional devices extending from drive tables without an angled support surface 7006 (e.g., the embodiment of the drive support table 20 shown in FIG. 1 and described above) may have a steep approach angle due to the distance between the superior surface and the access point on the patient (e.g., femoral access point). By comparison, interventional devices, such as catheters, extending from drive tables with an angled support surface 7006 may have a shallow approach angle due to the relatively short distance between the bottom of the angled support surface 7006 and the access point on the patient (e.g., femoral access point).

Figure 26:
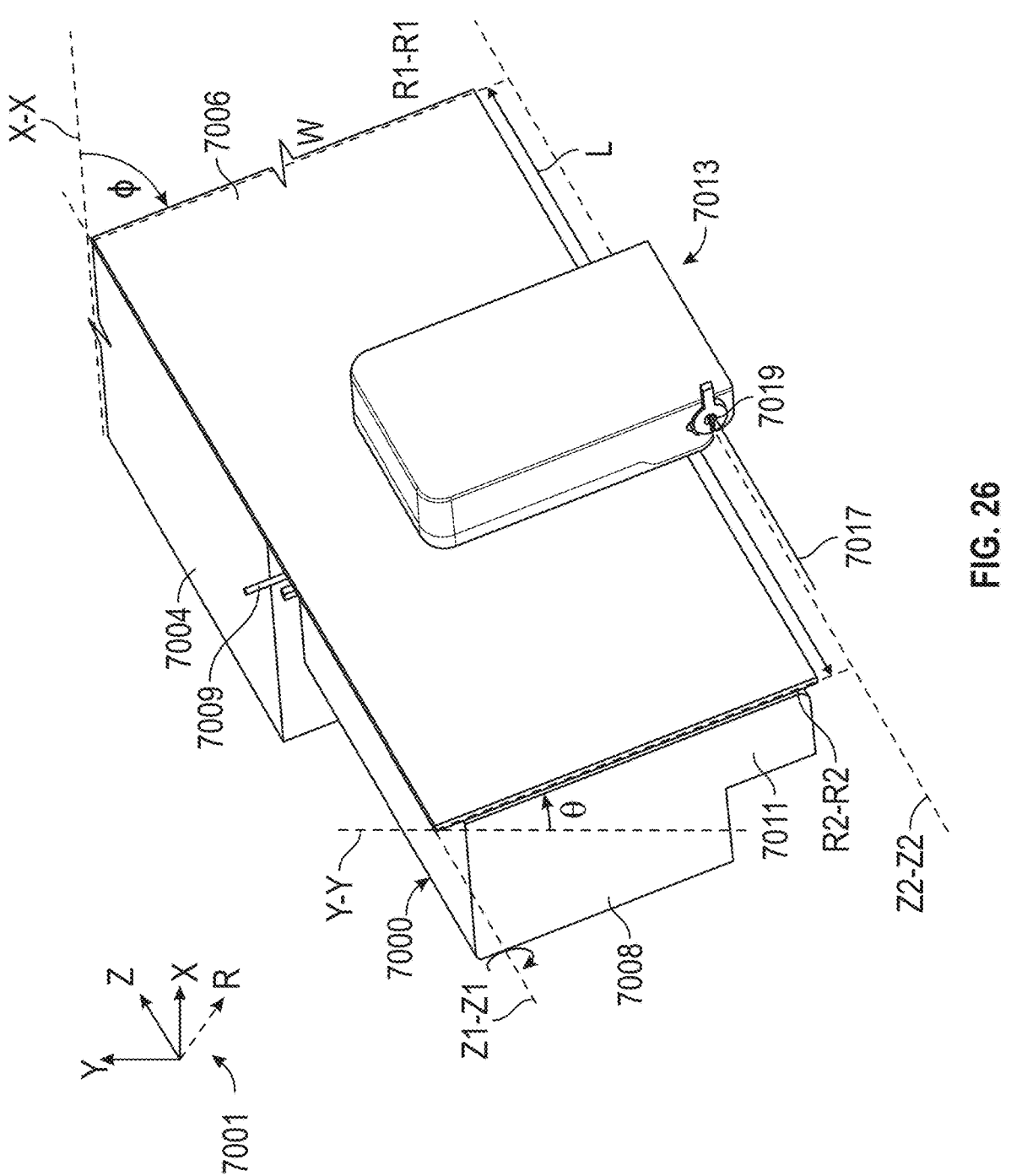
FIG. 26 illustrates a front perspective view of an angled drive table.

FIG. 26 illustrates a portion of an angled drive table 7000 positioned in three-dimensional space represented by a cartesian coordinate frame 7001. As shown in FIG. 26, the drive table 7000 includes an angled support surface 7006. The drive table can further include a main body 7004 and a secondary body and/or telescoping member 7008.

The main body 7004 and the telescoping member 7008 may further include internal mechanisms and systems, such as the internal components described above with respect to the drive table 6000. The telescoping member 7008 further includes an inferior support 7011. In some embodiments, the drive table 7000 can include two telescoping members 7008 that may telescope as described with respect to the telescoping members 6008.

FIG. 26 depicts an example of a hub 7013 positioned on the angled drive table 7000. The hub 7013 may further include an interventional device 7017. As described herein, a drive table, such as drive table 7000 may support a plurality of hubs.

The cartesian coordinate frame 7001 includes an ordered triplet of lines X, Y, Z illustrating directional orientation of three-dimensional space. The directional orientation of the cartesian coordinate frame 7001 includes an X direction, a Y direction, and a Z direction corresponding to the ordered triplet of lines X, Y, Z respectively. The X direction, Y direction, and Z direction are mutually orthogonal. As shown in FIG. 26, the X direction corresponds to a width in a horizontal orientation, the Y direction corresponds to a height in a vertical orientation, and the Z direction corresponds to a length in a horizontal orientation. In some embodiments, the cartesian coordinate frame 7001 includes a line R illustrating a directional orientation within the three-dimensional space defined by lines X, Y, Z. As shown in FIG. 26, the R direction corresponds to an orientation of the drive table within three-dimensional space relative to the X direction and the Y direction.

The angled support surface 7006 can be a substantially planar surface and configured for supporting the hub 7013. For example, the angled support surface 7006 may be the angled support surface described above. The length L of the angled support surface 7006 may be at least about 100 centimeters and within the range of from about 100 centimeters to about 2.7 meters. The length L of the angled support surface 7006 may extend between two edges in the Z direction. In some embodiments, two or more angled support surfaces 7006 may be used instead of a single angled support surface 7006. The two or more angled support surfaces 7006 may have a combined length L between 100 centimeters to about 2.7 meters. In some embodiments, the two or more angled support surfaces 7006 can be coplanar. The width W of the angled support surface 7006 may be between about 30 to about 80 centimeters. The width W of the angled support surface 7006 may correspond to a length of the angled support surface 7006 along an R-R axis. In some embodiments, the angled support surface 7006 may be defined by a sterile barrier extending between the lateral ends of the telescoping drive table 7000. The sterile barrier may be a deployable sterile barrier as described herein.

The main body 7004 may be defined by one or more exterior walls defining an interior cavity. The main body 7004 may provide a protective shell for internal components and protect the internal components from external forces applied to the drive table 7000. In some embodiments, the main body 7004 may include five sides. The five sides may form a five-sided cuboid shape. In some embodiments, the first housing may define one or more openings for receiving one or more inputs 7009.

The telescoping member 7008 may be defined by one or more exterior walls defining an interior cavity. The telescoping member 7008 may provide a protective shell for internal components and protect the internal components from external forces applied to the drive table 7000. As shown in FIG. 26, the telescoping member 7008 may be smaller than the main body 7004. In some embodiments, the telescoping member 7008 may include a main portion and an inferior support 7011. In some embodiments, the telescoping member 7008 may include seven sides. The telescoping member 7008 may define one or more openings for receiving one or more inputs 7009.

In some embodiments, the main body 7004 and the telescoping member 7008 may include one or more linear actuation assemblies and one or more hub adapters as described herein. The one or more linear actuator assemblies may be oriented along the length L of the drive table 7000 within the main body 7004 and the telescoping member 7008. The one or more hub adapters may move along the linear actuator assemblies.

The one or more inputs 7009 include bodies for transporting fluids, electrical power, electrical signals, and/or data. In some embodiments, the one or more inputs 7009 may include interventional devices, such as catheters, and/or cables. For example, the one or more inputs 7009 may introduce saline and/or contrast, aspirate bodily fluids, and/or provide electrical power.

The inferior support 7011 may be part of the telescoping member 7008. The inferior support 7011 may provide two or more of the walls of the telescoping member 7008. The inferior support 7011 may be configured to protect the driven hub 7013 from external forces applied to the drive table 7000. In some embodiments, the inferior support 7011 may extend along the length of the drive table 7000.

The one or more driven hubs 7013 may be the same or similar to the one or more hubs 6013 described above. As described herein, the one or more driven hubs 7013 may each be coupled to an interventional device, such as a guide catheter, a procedure catheter, an access catheter, and a guide catheter. In certain embodiments, one or more of the driven hubs 7013 may be configured for providing saline, contrast, and/or aspiration to a patient.

The driven hub 7013 can include an interventional device lumen 7019. An interventional device may be received partially within the lumen 7019 and secured therein to couple the interventional device to the hub. As shown in FIG. 26, an interventional device 7017 is coupled to the driven hub 7013. In some embodiments, a more proximal interventional device may be advanced through the lumen 7019 and through the interventional device 7017, as described herein.

In some embodiments, the telescoping table 7000 can further include a first ridge or guide (e.g., guide 6076) positioned above the one or more driven hubs 7013 and/or a second ridge or guide (e.g., guide 6078) below the one or more driven hubs 7013. The first and/or second ridges may form a channel through which the one or more hubs 7013 extend along the telescoping table 7000. The first and/or second ridges may advantageously prevent the one or more driven hubs 7013 from twisting or otherwise being unintentionally displaced along the drive table.

The X-X axis extends along the X direction. The X-X axis corresponds to a horizontal surface of a non-angled drive table. For example, the X-X axis may correspond to the horizontal orientation of embodiments of the drive support table 20, the drive table 6000, or the superior surface 7007 described above. The Y-Y axis extends along the Y direction corresponding to a vertical orientation. The Z-Z axes extend along the Z direction.

The Z1-Z1 axis extends along a superior edge of the support surface 7006. The Z1-Z1 axis may intersect the X-X axis corresponding to the horizontal plane of a non-angled drive table and/or the superior surface 7007 described above. The Z2-Z2 axis may extend through the interventional device lumen 7019 defined by the hub 7013. As shown in FIG. 26, the Z2-Z2 axis is coaxial with the interventional device lumen 7019. The Z2-Z2 axis may be coaxial with a longitudinal axis of the interventional device 7017 when the interventional device is in a straight configuration.

The R-R axes correspond to lateral edges of the angled support surface 7006. In some embodiments, the R-R axes correspond to the width W of the angled support surface 7006. In some embodiments, the R1-R1 axis corresponds to a distal side of the angled support surface 7006 and the R2-R2 axis corresponds to a proximal side of the angled support surface 7006. The R1-R1 and R2-R2 axes may be separated by the length L of the angled support surface 7006.

The R-R axes may be aligned along parallel X-Y planes. Accordingly, the relationship of the orientation of the R-R axes with respect to the X-X and Y-Y axes is a function of the angle of R-R about a Z-Z axis from either the X-X and/or Y-Y axes. As shown in FIG. 26, the R-R axes are offset from the X-X axis by an angle $\Phi$ about the Z1-Z1 axis. Similarly, the R-R axes are offset from the Y-Y axis by an angle $\theta$ about the Z1-Z1 axis.

As shown in FIG. 26, the angled support surface 7006 is supported by the main body 7004 and the telescoping member 7008. The angled support surface 7006 may be coupled to the rest of the drive table 7000 as described above. In some embodiments, the angled support surface 7006 may define the upper surface of the main body 7004 and/or telescoping member 7008.

As described herein, a hub adapter within the main body 7004 or the telescoping member 7008 may magnetically engage with the hub 7013 through the angled support surface 7006. Movement of the hub adapter may drive the hubs 7013 along the surface of the angled support surface 7006.

As described herein, axial movement of the hub 7013 can result in axial movement of the interventional device 7017 coupled thereto.

The angled drive table 7000 is positioned in a three-dimensional space having X, Y, and Z coordinates represented by the cartesian coordinate frame 7001. Non-angled or flat drive tables, as described herein, may have a support surface (e.g., an upper surface) for supporting one or more hubs that is coplanar with an X-Z plane. By comparison, as shown in FIG. 26, the angled drive table 7000 is oriented along an X-Y-Z plane. In some embodiments, the angled drive table 7000 may be achieved by orienting the drive table about a Z-Z axis. As shown in FIG. 26, the drive table is shown to be oriented about the Z1-Z1 axis at an angle $\Phi$, $\theta$. The angled drive table 7000 may be oriented relative to the horizontal X-X axis or horizontal plane and/or relative to the vertical Y-Y axis or vertical plane. Accordingly, the angled support surface 7006 may be offset from an axis X-X, Y-Y, from a horizontal plane, and/or from a vertical plane. In some embodiments, the angled support surface can be offset from an axis X-X, Y-Y, from a horizontal plane, or from a vertical plane by between 10 and 80 degrees. In some embodiments, the angled support surface can be offset from an axis X-X, Y-Y, from a horizontal plane, or from a vertical plane by between 20 and 70 degrees. In some embodiments, the angled support surface can be offset from an axis X-X, Y-Y, from a horizontal plane, or from a vertical plane by between 30 and 60 degrees.

For example, in some embodiments, the angled support surface can be oriented between 10 and 80 degrees from the horizontal plane, between 20 and 70 degrees from the horizontal plane, between 30 and 60 degrees from the horizontal plane, between 40 and 70 degrees from the horizontal plane, between 50 and 60 degrees from the horizontal plane. For example, the angled drive table 7000 may be oriented such that angled support surface 7006 is oriented 55 degrees from the horizontal X-X axis or horizontal plane. In some embodiments, the angled drive table 7000 can be oriented at least 10 degrees from the horizontal plane, at least 20 degrees from the horizontal plane, at least 30 degrees from the horizontal plane, at least 40 degrees from the horizontal plane, at least 50 degrees from the horizontal plane, at least 60 degrees from the horizontal plane, at least 70 degrees from the horizontal plane, or at least 80 degrees from the horizontal plane. In some embodiments, the angled drive table 7000 can be oriented no more than 10 degrees from the horizontal plane, no more than 20 degrees from the horizontal plane, no more than 30 degrees from the horizontal plane, no more than 40 degrees from the horizontal plane, no more than 50 degrees from the horizontal plane, no more than 60 degrees from the horizontal plane, no more than 70 degrees from the horizontal plane, or no more than 80 degrees from the horizontal plane. In some embodiments, the angled drive table 7000 can be oriented about 10 degrees from the horizontal plane, about 20 degrees from the horizontal plane, about 30 degrees from the horizontal plane, about 40 degrees from the horizontal plane, about 50 degrees from the horizontal plane, about 60 degrees from the horizontal plane, about 70 degrees from the horizontal plane, about 80 degrees from the horizontal plane, or about 90 degrees from the horizontal plane. In some embodiments, the angled support surface can be oriented between 10 and 80 degrees from the vertical plane, between 20 and 70 degrees from the vertical plane, between 30 and 60 degrees from the vertical plane, between 40 and 70 degrees from the vertical plane, between 50 and 60 degrees from the vertical plane. For example, the angled drive table 7000 may be oriented such that angled support surface 7006 is oriented 35 degrees from the vertical Y-Y axis or vertical plane. In some embodiments, the angled drive table 7000 can be oriented at least 10 degrees from the vertical plane, at least 20 degrees from the vertical plane, at least 30 degrees from the vertical plane, at least 40 degrees from the vertical plane, at least 50 degrees from the vertical plane, at least 60 degrees from the vertical plane, at least 70 degrees from the vertical plane, or at least 80 degrees from the vertical plane. In some embodiments, the angled drive table 7000 can be oriented no more than 10 degrees from the vertical plane, no more than 20 degrees from the vertical plane, no more than 30 degrees from the vertical plane, no more than 40 degrees from the vertical plane, no more than 50 degrees from the vertical plane, no more than 60 degrees from the vertical plane, no more than 70 degrees from the vertical plane, or no more than 80 degrees from the vertical plane. In some embodiments, the angled drive table 7000 can be oriented about 10 degrees from the vertical plane, about 20 degrees from the vertical plane, about 30 degrees from the vertical plane, about 40 degrees from the vertical plane, about 50 degrees from the vertical plane, about 60 degrees from the vertical plane, about 70 degrees from the vertical plane, or about 80 degrees from the vertical plane.

Figure 27:
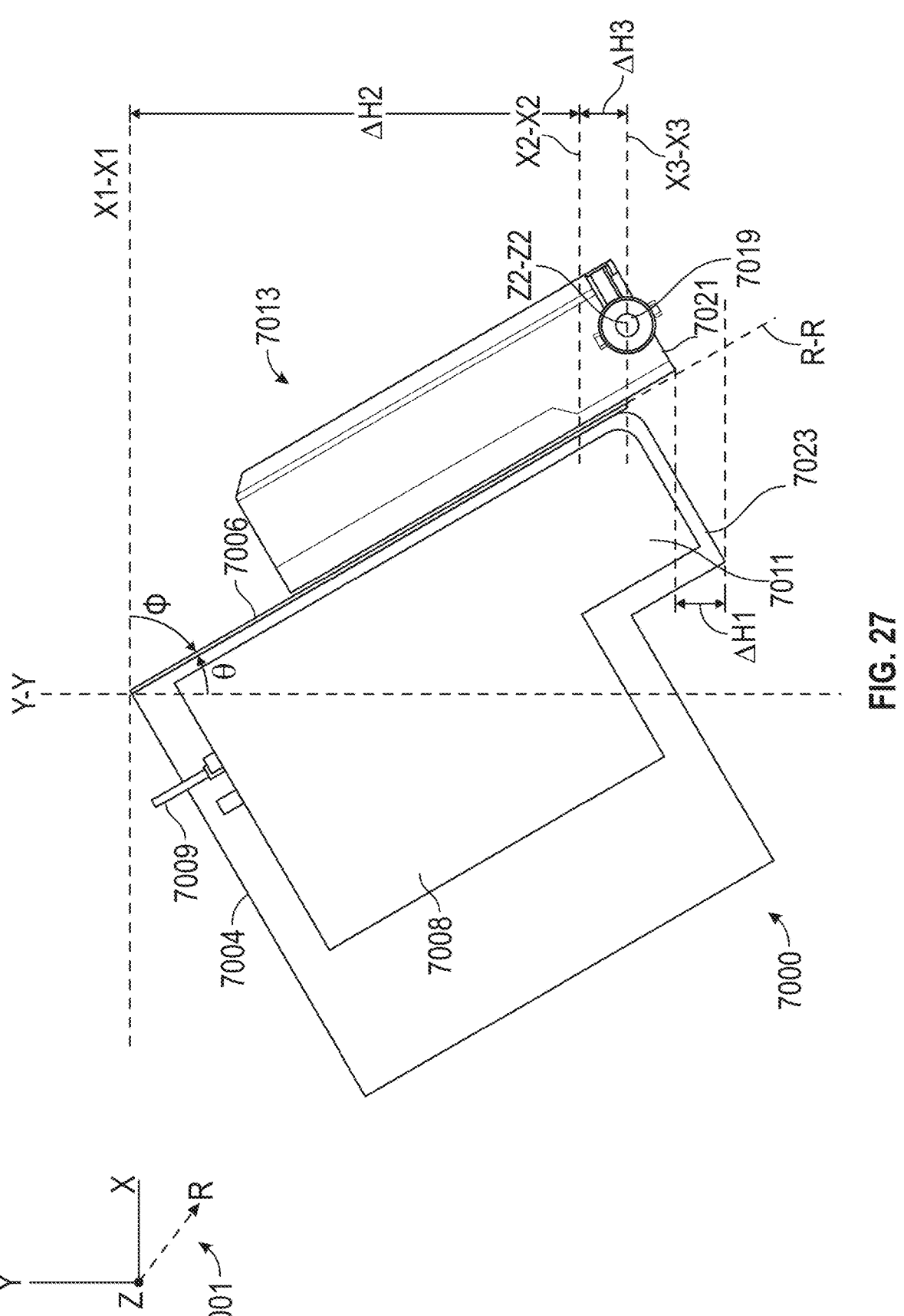
FIG. 27 illustrates a side view of the angled drive table of FIG. 26.

FIG. 27 shows a side view of the angled drive table 7000 of FIG. 26. As shown in FIG. 27, the sum of the angles Φ, θ is 90 degrees.

In some embodiments, the angle Φ can be between 10 and 80 degrees, between 20 and 70 degrees, between 30 and 60 degrees, between 40 and 70 degrees, or between 50 and 60 degrees. For example, the angle Φ may be 55 degrees. In some embodiments, the angle Φ can be at least 10 degrees, at least 20 degrees, at least 30 degrees, at least 40 degrees, at least 50 degrees, at least 60 degrees, at least 70 degrees, or at least 80 degrees. In some embodiments, the angle Φ can be no more than 10 degrees, no more than 20 degrees, no more than 30 degrees, no more than 40 degrees, no more than 50 degrees, no more than 60 degrees, no more than 70 degrees, or no more than 80 degrees. In some embodiments, the angle Φ can be about 10 degrees, about 20 degrees, about 30 degrees, about 40 degrees, about 50 degrees, about 60 degrees, about 70 degrees, about 80 degrees, or about 90 degrees.

In some embodiments, the angle θ can be between 10 and 80 degrees, between 20 and 70 degrees, between 30 and 60 degrees, between 40 and 70 degrees, or between 50 and 60 degrees. For example, the angle θ may be 35 degrees. In some embodiments, the angle θ can be at least 10 degrees, at least 20 degrees, at least 30 degrees, at least 40 degrees, at least 50 degrees, at least 60 degrees, at least 70 degrees, or at least 80 degrees. In some embodiments, the angle θ can be no more than 10 degrees, no more than 20 degrees, no more than 30 degrees, no more than 40 degrees, no more than 50 degrees, no more than 60 degrees, no more than 70 degrees, or no more than 80 degrees. In some embodiments, the angle θ can be about 10 degrees, about 20 degrees, about 30 degrees, about 40 degrees, about 50 degrees, about 60 degrees, about 70 degrees, about 80 degrees, or about 90 degrees.

Additionally, FIG. 27 shows the inferior support 7011 positioned along the bottom edge of the one or more hubs 7013. In certain embodiments, the inferior support 7011 is positioned below (e.g., along the Y-Y axis) the bottom most edge of the one or more hubs 7013. As shown in FIG. 27, the bottom surface 7023 of the inferior support 7011 can be positioned below the bottom surface 7021 of the one or more hubs 7013 by a first distance ΔH1. The inferior support 7011 may advantageously protect the one or more hubs 7013 from external forces coming from below the drive table 7000. For example, the inferior support 7011 may protect the one or more hubs 7013 from a force applied by a patient below the drive table 7000.

The second distance ΔH2 can extend between a first horizontal axis X1-X1 and a second horizontal axis X2-X2. The first horizontal axis X1-X1 may represent an upper surface of a non-angled drive table. The second horizontal axis X2-X2 may represent a horizontal axis intersecting an interventional lumen 7019 of the hub 7013 when a bottom surface 7021 of the hub 7013 is aligned with a bottom surface 7023 of the inferior support 7011. Accordingly, the angled drive table 7000 may advantageously reduce the dead length of the catheter. For example, the dead length may be reduced by at least the second distance ΔH2 between a superior surface of a non-angled drive table represented by axis X1-X1 and a corresponding position of an interventional lumen 7019 or interventional device longitudinal axis at a position where the hub 7013 is supported by the inferior support 7011 represented by axis X2-X2 such that the bottom surface 7021 of the hub 7013 is aligned with the bottoms surface 7023 of the inferior support 7011.

In some embodiments, as shown in FIG. 27, the one or more hubs 7013 may extend (e.g., laterally and/or inferiorly) beyond the angled drive table 7000. As shown in FIG. 27, the bottom surface 7021 of the one or more hubs 7013 can extend beyond the bottom surface 7023 of the angled support surface 7006. Positioning the one or more hubs 7013 at an inferior position along the angled support surface 7006 may advantageously further reduce the dead length of the interventional device 7017 by lowering the interventional device lumen 7019 and/or interventional device longitudinal axis (e.g., by an additional third distance ΔH3). Accordingly, the angled support surface 7006 may advantageously further minimize the dead length of the interventional device 7017 between the drive table 7000 and the patient.

Figure 28:
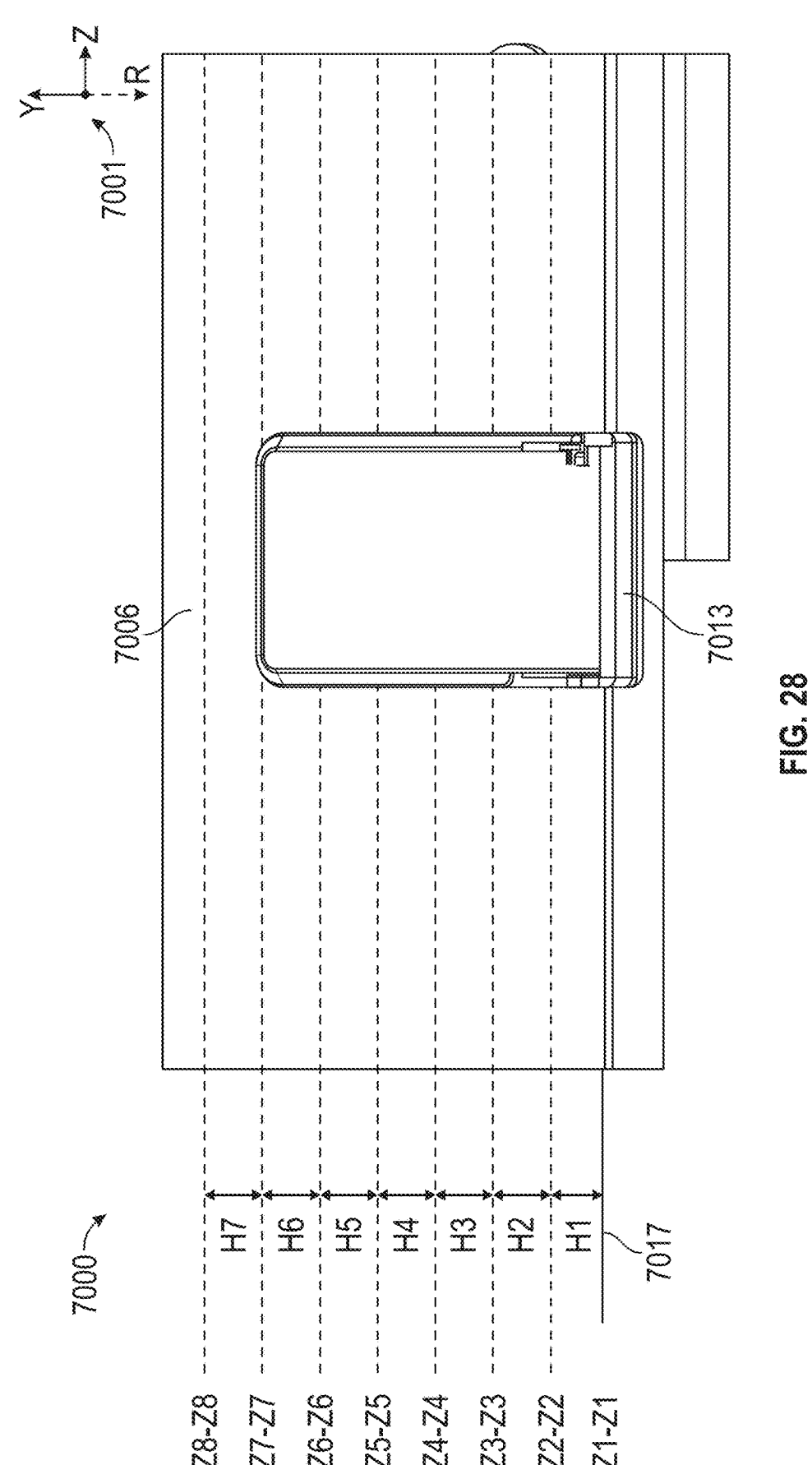
FIG. 28 illustrates a front view of the angled drive table of FIG. 26.

FIG. 28 shows a front view of the angled drive table 7000 of FIGS. 26 and 27. As shown in FIG. 28, the angled support surface 7006 may have a plurality of heights aligned along a plurality of Z-Z axes. In some embodiments, the one or more hubs 7013 may be aligned along a first axis Z1-Z1. The first axis Z1-Z1 may be a bottom most position of the one or more hubs 7013 along the angled support surface 7006. In some embodiments, the one or more hubs 7013 may be aligned along a second axis Z8-Z8. The second axis Z8-Z8 may be an upper most position of the one or more hubs 7013. There may be a plurality of possible heights between the first axis Z1-Z1 and the second axis Z2-Z2.

The one or more hubs 7013 may be positioned along the angled support surface 7006 at a height along a Y-Y axis corresponding to one of the Z-Z axes. As shown in FIG. 28, in some embodiments, the higher the one or more hubs 7013 are positioned along the angled support surface 7006, the greater the dead length of the interventional device 7017 and a corresponding steep approach angle. By comparison, in some embodiments, the lower the one or more hubs 7013 are positioned along the angled support surface 7006, the lesser the dead length of the interventional device 7017 and a corresponding shallow approach angle.

Figure 29:
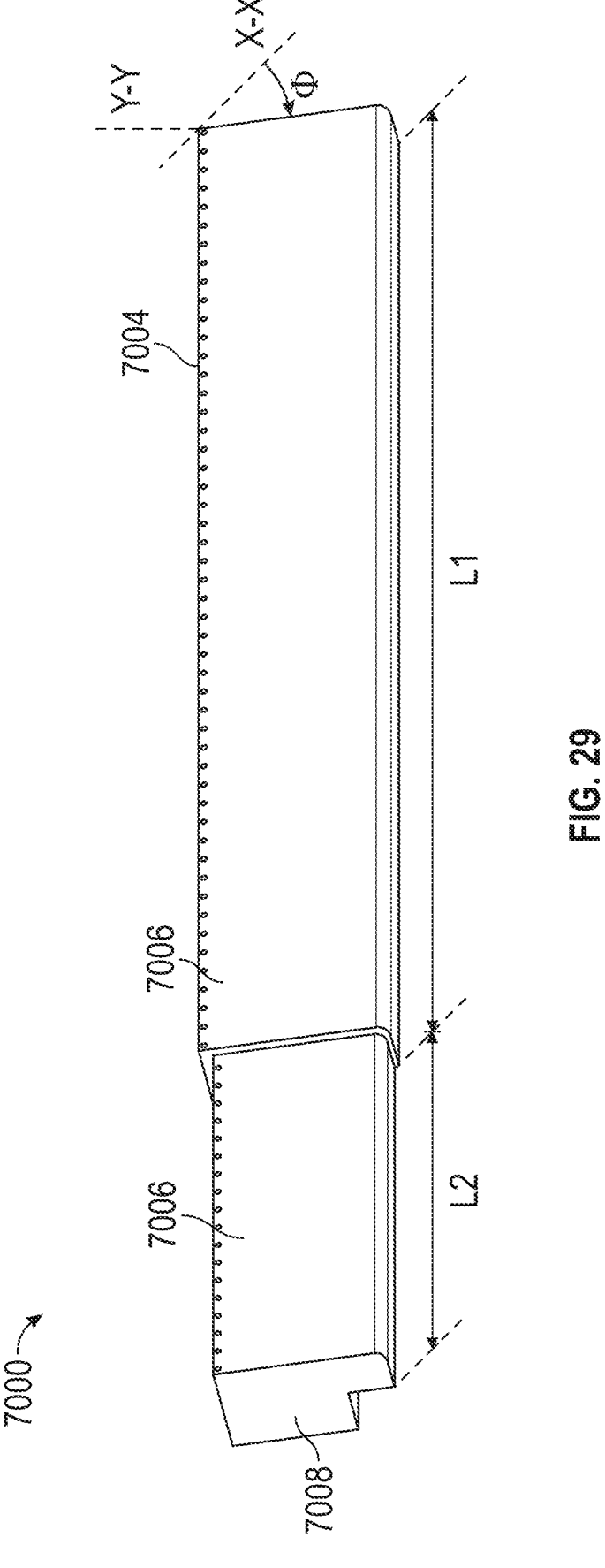
FIG. 29 illustrates a front perspective view of an angled telescoping drive table.

FIG. 29 illustrates an embodiment of an angled telescoping drive table 7000. In some embodiments, the angled telescoping drive table 7000 may include any of the same or similar features and/or functions as the drive table 7000 discussed with respect to FIGS. 26 and 27. The telescoping drive table 7000 may include any of the same and/or similar telescoping features and/or functions as the telescoping drive table 6000. For example, the angled telescoping drive table 7000 may include one or more telescoping members 7008.

In some embodiments, an angled support surface 7006 may not be part of the drive table, but may be a separate component positioned relative to the drive table (e.g., coupled to the drive table, positioned on a superior surface of the drive table, etc.) so that hubs may be driven along the angled support surface 7006. For example, in some embodiments, the drive table 7000 may be a flat or horizontal top surface, and an angled support surface 7006 can be positioned relative thereto to facilitate movement of the hubs and interventional devices along the support surface 7006.

The foregoing represents example embodiments of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

Figure 30:
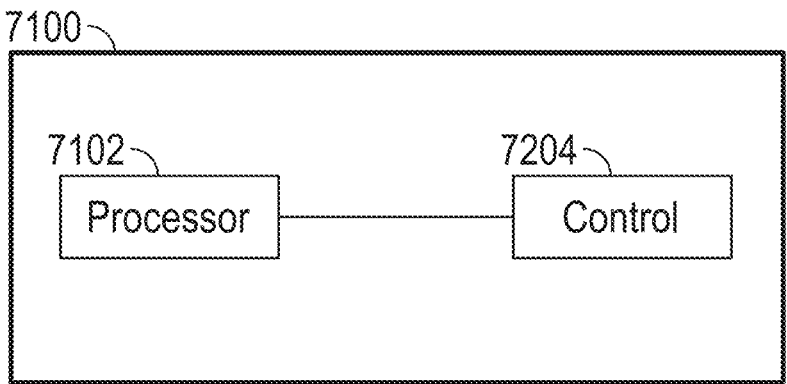
FIG. 30 illustrates a schematic diagram of a control system.

Control System:

FIG. 30 illustrates a schematic view of an example of a control system 7100 that may be used to electronically control the systems and components described herein and/or perform the methods described herein. The control system 7100 may be configured to automatically adjust various motors, hub adapters, hubs, shuttles, linear actuators, interventional devices, fluidics components (e.g., valves, pumps, etc.), and/or any other components described herein in response to commands input by an operator such as a physician. In response to command inputs by an operator, the control system 7100 may cause a series of responsive events to automatically occur.

In certain embodiments, the control system 7100 can include one or more processors 7102 (e.g., hardware processors). The one or more processors 7102 can be configured to automatically adjust the various system components described herein in response to commands input by an operator, for example, using one or more controls 7104 of the control system 7100. A single control 7104 is shown in FIG. 30. However, any suitable number of controls may be provided to correspond to various functions of the systems described herein. For example, in certain embodiments, each interventional device may have its own unique control 7104 or set of controls 7104 that can control various functions of the interventional device (e.g., axial movement, rotational movement, supply of fluids (e.g., saline, contrast, etc.), aspiration, etc.).

In certain embodiments, one or more controls 7104 may be operated to control movement of one or more telescoping or extendable members or movement of a drive table. In certain embodiments, one or more controls 7104 may be operated to control movement of one or more interventional devices. For example, one or more controls 7104 may be operated to control movement of a shuttle and/or one or more hub adapters.

The processor 4002 may receive signals from the one or more controls 4004 and in response, initiate corresponding actions in the components of the systems described herein. For example, the processor 4002 may be configured to generate output signals that cause responsive actions to be performed by the components of the described herein.

Various systems and methods are described herein primarily in the context of a neurovascular access or procedure. However, the inventors contemplate applicability of the disclosed catheters, systems, and methods to any of a wide variety of alternative applications, including within the coronary vascular or peripheral vascular systems as well as other hollow organs or tubular structures in the body.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

While certain arrangements of the inventions have been described, these arrangements have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, arrangement, or example are to be understood to be applicable to any other aspect, arrangement or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing arrangements. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some arrangements, the actual steps taken in the processes illustrated and/or disclosed may differ from those shown in the figures. Depending on the arrangement, certain of the steps described above may be removed, others may be added. Furthermore, the features and attributes of the specific arrangements disclosed above may be combined in different ways to form additional arrangements, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular arrangement. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain arrangements include, while other arrangements do not include, certain features, elements, and/or steps. Thus, such conditional language is not generally intended to imply that features, elements, and/or steps are in any way required for one or more arrangements or that one or more arrangements necessarily include logic for deciding, with or without user input or prompting, whether these features, elements, and/or steps are included or are to be performed in any particular arrangement.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain arrangements require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain arrangements, the terms "generally parallel" and "substantially parallel" refer to a value, amount, or characteristic that departs from exactly parallel by less than or equal to 15°, 10°, 5°, 3°, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred arrangements in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of driving an interventional device assembly, comprising:

axially advancing an extendable member from a proximal end or a distal end of a main body of a drive table; and axially advancing a hub adapter from a first axial position within the main body to a second axial position within the extendable member beyond the proximal end or the distal end of the main body, the hub adapter being configured to couple to a corresponding hub so that axial movement of the hub adapter drives axial movement of the corresponding hub.

2. The method of claim 1, wherein the hub adapter is configured to drive movement of the hub from a first axial position on a drive surface of the main body to a second axial position on a drive surface of the extendable member.

3. The method of claim 1, wherein the hub is a guide catheter hub.

4. The method of claim 3, wherein the hub adapter is a first hub adapter, the method further comprising:

axially advancing a second hub adapter configured to couple to an access catheter; and axially advancing a third hub adapter configured to couple to a procedure catheter.

5. The method of claim 4, further comprising axially advancing a fourth hub adapter configured to couple to a guidewire hub.

6. The method of claim 3, wherein the extendable member is extendable from the distal end of the main body.

7. The method of claim 1, wherein the hub is a guidewire hub.

8. The method of claim 7, wherein the extendable member is extendable from the proximal end of the main body.

9. The method of claim 1, further comprising a shuttle configured to move axially within the main body and the extendable member, wherein the hub adapter is configured to move axially along the shuttle.

10. The method of claim 9, wherein the drive table comprises:

a first linear actuator assembly configured to control axial movement of the shuttle within the main body and the extendable member;

a second linear actuator assembly configured to control axial movement of the hub adapter relative to the shuttle; and a third linear actuator assembly configured to control axial movement of the extendable member.

11. The method of claim 9, wherein the drive table further comprises a cable management system configured to position one or more cables within an interior section of the shuttle.

12. The method of claim 11, wherein the drive table further comprises a motor configured to drive the hub adapter axially along the shuttle, wherein the cable management system is configured to prevent engagement of the one or more cables with the motor.

13. The method of claim 1, wherein the extendable member is a first extendable member, the first extendable member being extendable from the distal end of the main body, the method further comprising axially advancing a second extendable member from the proximal end of the main body of the drive table.

14. The method of claim 13, wherein each of the first extendable member and the second extendable member has a length of about half of a length of the main body.

15. The method of claim 13, wherein the hub adapter comprises a first hub adapter, the method further comprising axially advancing a second hub adapter to a first axial position within the main body to a second axial position within the second extendable member beyond the proximal end of the main body.

16. The method of claim 1, further comprising moving the drive table relative to a base structure in an axial direction and/or in a vertical direction by an arm coupled with the base structure.

17. The method of claim 1, wherein the drive table comprises a drive surface oriented at an angle relative to horizontal plane.

* * * * *